(12) United States Patent
Chen et al.

(10) Patent No.: US 12,065,697 B2
(45) Date of Patent: Aug. 20, 2024

(54) B-FAMILY DNA POLYMERASE VARIANT AND KIT COMPRISING THE SAME

(71) Applicant: Cheng-Yao Chen, Hsinchu (TW)

(72) Inventors: Cheng-Yao Chen, Hsinchu (TW); Yi-Wen Cheng, Hsinchu (TW); Yu Ting Hung, Hsinchu (TW); Wen-Ting Chen, Hsinchu (TW)

(73) Assignee: Cheng-Yao Chen, Hsinchu (TW)

( * ) Notice: Subject to any disclaimer, the term of this patent is extended or adjusted under 35 U.S.C. 154(b) by 0 days.

(21) Appl. No.: 17/852,008

(22) Filed: Jun. 28, 2022

(65) Prior Publication Data

US 2023/0107606 A1 Apr. 6, 2023

Related U.S. Application Data

(60) Provisional application No. 63/249,813, filed on Sep. 29, 2021.

(51) Int. Cl.
*C12Q 1/6874* (2018.01)
*C12N 9/12* (2006.01)

(52) U.S. Cl.
CPC ......... *C12Q 1/6874* (2013.01); *C12N 9/1252* (2013.01); *C12Y 207/07007* (2013.01)

(58) Field of Classification Search
None
See application file for complete search history.

(56) References Cited

U.S. PATENT DOCUMENTS

2016/0032377 A1* 2/2016 Chen .................... C12N 9/1252
506/26

OTHER PUBLICATIONS

Chica et al. Curr Opin Biotechnol. Aug. 2005;16(4):378-84. (Year: 2005).*
Singh et al. Curr Protein Pept Sci. 2017, 18, 1-11 (Year: 2017).*
Bornscheuer et al. Curr Protoc Protein Sci. Nov. 2011;Chapter 26:Unit26.7 (Year: 2011).*
Yoshikuni et al. Curr Opin Chem Biol. Apr. 2007;11(2):233-9. (Year: 2007).*
Accession A0A5C0XMA4. Nov. 13, 2019 (Year: 2019).*

* cited by examiner

*Primary Examiner* — Christian L Fronda
(74) *Attorney, Agent, or Firm* — MUNCY, GEISSLER, OLDS & LOWE, P.C.

(57) ABSTRACT

Disclosed herein is a specific B-family DNA polymerase variants that exhibit an improved incorporation of nucleotide analogues for synthesizing polynucleotides and sequencing the associated nucleic acid template. More particularly, the DNA sequencing-by-synthesis method can be efficiently performed by said B-family DNA polymerase variants with a normal nucleic acid template and reversible dye-terminator nucleotides to precisely determine the sequence of associated nucleic acid template.

18 Claims, 21 Drawing Sheets

Specification includes a Sequence Listing.

B-FAMILY DNA POLYMERASE VARIANT AND KIT COMPRISING THE SAME

CROSS REFERENCE

This application claims priority to, and the benefit of, U.S. Provisional Application No. U.S. 63/249,813, filed on Sep. 29, 2021, the content thereof is incorporated by reference herein.

FIELD OF THE INVENTION

The present invention relates to, among other things, B-family DNA polymerase variants and kits comprising the same for use particularly in the context of nucleic acid sequencing by synthesis.

SEQUENCE LISTING

The present application is being filed along with a Sequence Listing in electronic format. The Sequence Listing is provided as a file entitled P222285US-sequence listing.TXT, created on Jun. 8, 2022, which is 127 kb in size. The information in the electronic format of Sequence Listing is incorporated herein by reference in its entirety.

BACKGROUND OF THE INVENTION

Next-generation sequencing (NGS) technologies have revolutionized modern biological and biomedical research. The engines responsible for this innovation are DNA polymerases, which catalyze the biochemical reaction for deriving template sequence information. As one of the widely adopted NGS platforms, the DNA sequencing-by-synthesis (SBS) technique is a unique, polymerase-dependent approach for that the consecutive sequencing reaction thereof concurrently generates a newly synthesized DNA strand as a result.

The general SBS approach involves (i) incorporation of nucleotide analogues bearing fluorescent reporters, (ii) identification of the incorporated nucleotide by its fluorescent emissions, and (iii) cleavage of the fluorophore, along with the reinitiation of the polymerase reaction for stepwise sequence determination. In contrast to conventional Sanger sequencing, the fluorescently labeled DNA fragments of different sizes are generated in a single reaction and, thus, required DNA separation by electrophoresis followed with a fluorescent detection. The SBS approach is more robust than Sanger's dideoxy-sequencing method because individual DNA fragments, or clusters, for sequence determination are immobilized on a high-density array. Hence, the SBS fluorescent signals from each DNA fragments or clusters can be directly detected without the need for prior DNA separations. Furthermore, by using massive parallel microarray chip, the SBS approach can easily be scaled up to increase overall sequencing output and greatly reduces the cost of DNA sequencing.

Nevertheless, the nucleotides used in the SBS approach are variedly modified. These nucleotide analogues carry either a larger chemical blocking group at the 3'-hydroxyl (3'-OH) position of deoxyribose or a bulky fluorescent molecule on the nucleobase. These large, chemical modifications on the nucleotide are not well-tolerated by naturally occurring nucleic acid polymerase. The active-site pocket of nucleic acid polymerase is pre-arranged in a proper geometry for accommodating a correct and matched canonical nucleotide having a normal 3'—OH group and a nucleobase. The elimination, or any substitution, of the 3'—OH group with a bulky, chemical group on the nucleotide, such as 2', 3'-dideoxycleotide (ddNTP) and 3'-O-azidomethyl-dNTP, respectively, significantly alters the nucleotide configuration within the active-site pocket of nucleic acid polymerase and reduces the nucleotide binding affinity and overall DNA synthesis efficiency of nucleic acid polymerase. Likewise, any modifications on the nucleobase or 5'-triphosphate group of the nucleotide, disrupts the interactions between the nucleotide and active-site residues of nucleic acid polymerase and leads to a poor utilization of these modified nucleotides for nucleic acid synthesis by the polymerase.

In view of that a series of nucleotide modifications are constantly created for rapidly changing DNA polymerase-based sequencing technologies, it is crucial to look for, design or evolve compatible enzymes for ever-changing DNA sequencing chemistries, such as U.S. Ser. No. 11/104,888B2 disclosed a variant of archaeal 9° N DNA polymerase (a B-family Pol), which has been found to incorporate reversible dye-terminator nucleotides well.

SUMMARY OF THE INVENTION

Owing to the diverse properties of modified nucleotide analogues, the naturally occurring nucleic acid polymerases cannot readily utilize these nucleotide analogues as a substrate for the template-directed nucleic acid synthesis. Thus, the tailor-made, modified nucleic acid polymerase is a prerequisite for exerting the utilities of these non-canonical nucleotides for a variety of nucleic acid sequencing-by-synthesis applications.

The inventor has discovered the novel positions/regions in the amino acid sequences of B-family DNA polymerases that play crucial parts in enhancing the substrate affinity of said polymerases for modified nucleotides, thereby improving the nucleotide-incorporation efficiency in the DNA sequencing-by-synthesis method.

Accordingly, in one aspect, the invention provides a B-family DNA polymerase variant comprising: a motif Exo I, a motif Exo II, a motif Exo III, a motif A, a motif B, and a motif C corresponding respectively to positions 349 to 364, 450 to 476, 590 to 608, 706 to 730, 843 to 855, and 940 to 956 of a consensus sequence (SEQ ID NO:1); at least one amino acid substitution at a position residing in a motif selected from the group consisting of the motif Exo I, the motif Exo II, and the motif Exo III; and at least one amino acid substitution at a positions residing in a motif selected from the group consisting of the motif A, the motif B, and the motif C.

In one embodiment, the B-family DNA polymerase variant is modified from a wild-type B-family DNA polymerase having an amino acid sequence selected from the group consisting of SEQ ID NO: 2, 3, 4, 5, 6, 7, 8, 9, 10, 11, 12, 13, 14, 15, 16 and 17.

In one embodiment, the wild-type B-family DNA polymerase is *Thermococcus gorgonarius* DNA polymerase (Tgo), *Thermococcus kodakarensis* DNA polymerase (Kod1), *Thermococcus* sp. (strain 9° N-7) DNA polymerase (9° N), *Pyrococcus furiosus* DNA polymerase (Pfu), *Thermococcus litoralis* DNA polymerase (Vent), *Methanococcus maripaludis* DNA polymerase (Mma), *Methanosarcina acetivorans* DNA polymerase (Mac), human DNA polymerase delta catalytic p125 subunit (hPOLD), *Saccharomyces cerevisiae* DNA polymerase delta catalytic subunit (ScePOLD), *Pyrobaculum islandicum* DNA polymerase, (Pis) *Sulfolobus solfataricus* DNA polymerase (Sso), *Pseudomonas aeruginosa* DNA polymerase II (Pae), *Escherichia coli* DNA polymerase II (Eco), Bacteriophage (*Escherichia* phage) RB69 DNA polymerase (RB69), Bacteriophage (*Escherichia* phage) T4 DNA polymerase (T4), or Bacteriophage (*Bacillus* phage) Phi29 DNA polymerase (Phi29).

In one embodiment, the amino acid of corresponding to position 354 of SEQ ID NO: 1 is any amino acid other than D; the amino acid corresponding to position 355 of SEQ ID NO:1 is any amino acid other than I; the amino acid corresponding to position 356 of SEQ ID NO:1 is any amino acid other than E; the amino acid corresponding to position 715 of SEQ ID NO:1 is any amino acid other than L; the amino acid corresponding to position 716 of SEQ ID NO: 1 is any amino acid other than Y; and the amino acid of corresponding to position 717 of SEQ ID NO:1 is any amino acid other than P.

In one embodiment, the amino acid corresponding to position 354 of SEQ ID NO:1 is any amino acid other than D; the amino acid corresponding to position 355 of SEQ ID NO:1 is any amino acid other than I; the amino acid corresponding to position 356 of SEQ ID NO:1 is any amino acid other than E; the amino acid corresponding to position 715 of SEQ ID NO:1 is any amino acid other than L; the amino acid corresponding to position 716 of SEQ ID NO:1 is any amino acid other than Y; the amino acid corresponding to position 717 of SEQ ID NO: 1 is any amino acid other than P; and the amino acid corresponding to position 854 of SEQ ID NO:1 is any amino acid other than A.

In one embodiment, the B-family DNA polymerase variant is derived from *Thermococcus kodakarensis* DNA polymerase (Kod1) having a wild-type amino acid sequence of SEQ ID NO:3; and wherein: D141 of SEQ ID NO:3 corresponding to position 354 of SEQ ID NO:1 is substituted with A; E143 of SEQ ID NO:3 corresponding to position 356 of SEQ ID NO:1 is substituted with A; L408 of SEQ ID NO:3 corresponding to position 715 of SEQ ID NO:1 is substituted with A, F, I, M, Q, S, H or Y; Y409 of SEQ ID NO:3 corresponding to position 716 of SEQ ID NO:1 is substituted with A, C, D, F, G, H or I; and P410 of SEQ ID NO:3 corresponding to position 717 of SEQ ID NO:1 is substituted with A, C, F, G, S or T.

In one embodiment, the B-family DNA polymerase variant is derived from *Thermococcus* sp. (strain 9° N-7) DNA polymerase (9° N) having a wild-type amino acid sequence of SEQ ID NO:4; and wherein: D141 of SEQ ID NO:4 corresponding to position 354 of SEQ ID NO:1 is substituted with A; E143 of SEQ ID NO:4 corresponding to position 356 of SEQ ID NO:1 is substituted with A; L408 of SEQ ID NO:4 corresponding to position 715 of SEQ ID NO:1 is substituted with A, F, I, M, Q, S, H or Y; Y409 of SEQ ID NO:4 corresponding to position 716 of SEQ ID NO:1 is substituted with A, C, D, F, G, H or I; and P410 of SEQ ID NO:4 corresponding to position 717 of SEQ ID NO: 1 is substituted with A, C, F, G, S or T.

In one embodiment, the B-family DNA polymerase variant is derived from *Pyrococcus furiosus* DNA polymerase (Pfu) having a wild-type amino acid sequence of SEQ ID NO:5; and wherein: D141 of SEQ ID NO:5 corresponding to position 354 of SEQ ID NO:1 is substituted with A; E143 of SEQ ID NO:5 corresponding to position 356 of SEQ ID NO:1 is substituted with A; L409 of SEQ ID NO:5 corresponding to position 715 of SEQ ID NO: 1 is substituted with A, F, I, M, Q, S, H or Y; Y410 of SEQ ID NO:5 corresponding to position 716 of SEQ ID NO:1 is substituted with A, C, D, F, G, H or I; and P411 of SEQ ID NO:5 corresponding to position 717 of SEQ ID NO:1 is substituted with A, C, F, G, S or T.

In one embodiment, the B-family DNA polymerase variant is derived from *Thermococcus litoralis* DNA polymerase (Vent) having a wild-type amino acid sequence of SEQ ID NO:6; and wherein: D141 of SEQ ID NO:6 corresponding to position 354 of SEQ ID NO:1 is substituted with A; E143 of SEQ ID NO:6 corresponding to position 356 of SEQ ID NO:1 is substituted with A; L411 of SEQ ID NO:6 corresponding to position 715 of SEQ ID NO: 1 is substituted with A, F, I, M, Q, S, H or Y; Y412 of SEQ ID NO:6 corresponding to position 716 of SEQ ID NO:1 is substituted with A, C, D, F, G, H or I; and P413 of SEQ ID NO:6 corresponding to position 717 of SEQ ID NO: 1 is substituted with A, C, F, G, S or T.

In one embodiment, the B-family DNA polymerase variant is derived from *Methanosarcina acetivorans* DNA polymerase (Mac) having a wild-type amino acid sequence of SEQ ID NO:8; and wherein: D198 of SEQ ID NO:8 corresponding to position 354 of SEQ ID NO:1 is substituted with A; E200 of SEQ ID NO:8 corresponding to position 356 of SEQ ID NO:1 is substituted with A; L485 of SEQ ID NO:8 corresponding to position 715 of SEQ ID NO: 1 is substituted with A, F, I, M, Q, S, H or Y; Y486 of SEQ ID NO:8 corresponding to position 716 of SEQ ID NO:1 is substituted with A, C, D, F, G, H or I; and P487 of SEQ ID NO:8 corresponding to position 717 of SEQ ID NO: 1 is substituted with A, C, F, G, S or T.

In one embodiment, the B-family DNA polymerase variant is derived from *Pyrobaculum islandicum* DNA polymerase (Pis) having a wild-type amino acid sequence of SEQ ID NO:11; and wherein: D171 of SEQ ID NO:11 corresponding to position 354 of SEQ ID NO: 1 is substituted with A; E173 of SEQ ID NO:11 corresponding to position 356 of SEQ ID NO:1 is substituted with A; M426 of SEQ ID NO:11 corresponding to position 715 of SEQ ID NO: 1 is substituted with A, F, I, Q, S, H or Y; Y427 of SEQ ID NO:11 corresponding to position 716 of SEQ ID NO:1 is substituted with A, C, D, F, G, H or I; and P428 of SEQ ID NO:11 corresponding to position 717 of SEQ ID NO:1 is substituted with A, C, F, G, S or T.

In one embodiment, the B-family DNA polymerase variant is derived from *Sulfolobus solfataricus* DNA polymerase (Sso) having a wild-type amino acid sequence of SEQ ID NO: 12; and wherein: D231 of SEQ ID NO: 12 corresponding to position 354 of SEQ ID NO:1 is substituted with A; E233 of SEQ ID NO:12 corresponding to position 356 of SEQ ID NO:1 is substituted with A; L518 of SEQ ID NO:12 corresponding to position 715 of SEQ ID NO: 1 is substituted with A, F, I, M, Q, S, H or Y; Y519 of SEQ ID NO: 12 corresponding to position 716 of SEQ ID NO: 1 is substituted with A, C, D, F, G, H or I; an P520 of SEQ ID NO:12 corresponding to position 717 of SEQ ID NO:1 is substituted with A, C, F, G, S or T.

In one embodiment, the B-family DNA polymerase variant is derived from *Thermococcus kodakarensis* DNA polymerase (Kod1) having a wild-type amino acid sequence of SEQ ID NO:3; and wherein: D141 of SEQ ID NO:3 corresponding to position 354 of SEQ ID NO:1 is substituted with A; E143 of SEQ ID NO:3 corresponding to position 356 of SEQ ID NO:1 is substituted with A; L408 of SEQ ID NO:3 corresponding to position 715 of SEQ ID NO: 1 is substituted with A, F, I, M, Q, S, H or Y; Y409 of SEQ ID NO:3 corresponding to position 716 of SEQ ID NO:1 is substituted with A, C, D, F, G, H or I; P410 of SEQ ID NO:3 corresponding to position 717 of SEQ ID NO:1 is substituted with A, C, F, G, S or T; and A485 of SEQ ID NO:3 corresponding to position 854 of SEQ ID NO: 1 is substituted with C, D, E, F, or L.

In one embodiment, the B-family DNA polymerase variant is derived from *Thermococcus* sp. (strain 9° N-7) DNA polymerase (9° N) having a wild-type amino acid sequence of SEQ ID NO:4; and wherein: D141 of SEQ ID NO:4 corresponding to position 354 of SEQ ID NO:1 is substituted with A; E143 of SEQ ID NO:4 corresponding to position 356 of SEQ ID NO:1 is substituted with A; L408 of SEQ ID NO:4 corresponding to position 715 of SEQ ID NO:1 is substituted with A, F, I, M, Q, S, H or Y; Y409 of SEQ ID NO:4 corresponding to position 716 of SEQ ID NO:1 is substituted with A, C, D, F, G, H or I; P410 of SEQ ID NO:4 corresponding to position 717 of SEQ ID NO:1 is substituted with A, C, F, G, S or T; and A485 of SEQ ID NO:4 corresponding to position 854 of SEQ ID NO: 1 is substituted with C, D, E, F, or L.

In one embodiment, the B-family DNA polymerase variant is derived from *Pyrococcus furiosus* DNA polymerase (Pfu) having a wild-type amino acid sequence of SEQ ID NO:5; and wherein: D141 of SEQ ID NO:5 corresponding to position 354 of SEQ ID NO:1 is substituted with A; E143 of SEQ ID NO:5 corresponding to position 356 of SEQ ID NO:1 is substituted with A; L409 of SEQ ID NO:5 corresponding to position 715 of SEQ ID NO: 1 is substituted with A, F, I, M, Q, S, H or Y; Y410 of SEQ ID NO:5 corresponding to position 716 of SEQ ID NO:1 is substituted with A, C, D, F, G, H or I; P411 of SEQ ID NO:5 corresponding to position 717 of SEQ ID NO:1 is substituted with A, C, F, G, S or T; and A486 of SEQ ID NO:5 corresponding to position 854 of SEQ ID NO: 1 is substituted with C, D, E, F, or L.

In one embodiment, the B-family DNA polymerase variant is derived from *Thermococcus litoralis* DNA polymerase (Vent) having a wild-type amino acid sequence of SEQ ID NO:6; and wherein: D141 of SEQ ID NO:6 corresponding to position 354 of SEQ ID NO:1 is substituted with A; E143 of SEQ ID NO:6 corresponding to position 356 of SEQ ID NO:1 is substituted with A; L411 of SEQ ID NO:6 corresponding to position 715 of SEQ ID NO:1 is substituted with A, F, I, M, Q, S, H or Y; Y412 of SEQ ID NO:6 corresponding to position 716 of SEQ ID NO: 1 is substituted with A, C, D, F, G, H or I; P413 of SEQ ID NO:6 corresponding to position 717 of SEQ ID NO:1 is substituted with A, C, F, G, S or T; and A488 of SEQ ID NO:6 corresponding to position 854 of SEQ ID NO: 1 is substituted with C, D, E, F, or L.

In one embodiment, the B-family DNA polymerase variant is derived from *Methanosarcina acetivorans* DNA polymerase (Mac) having a wild-type amino acid sequence of SEQ ID NO:8; and wherein: D198 of SEQ ID NO:8 corresponding to position 354 of SEQ ID NO:1 is substituted with A; E200 of SEQ ID NO:8 corresponding to position 356 of SEQ ID NO:1 is substituted with A; L485 of SEQ ID NO:8 corresponding to position 715 of SEQ ID NO: 1 is substituted with A, F, I, M, Q, S, H or Y; Y486 of SEQ ID NO:8 corresponding to position 716 of SEQ ID NO:1 is substituted with A, C, D, F, G, H or I; P487 of SEQ ID NO:8 corresponding to position 717 of SEQ ID NO:1 is substituted with A, C, F, G, S or T; and A565 of SEQ ID NO:8 corresponding to position 854 of SEQ ID NO:1 is substituted with C, D, E, F, or L.

In one embodiment, the B-family DNA polymerase variant is derived from *Pyrobaculum islandicum* DNA polymerase (Pis) having a wild-type amino acid sequence of SEQ ID NO:11; and wherein: D171 of SEQ ID NO:11 corresponding to position 354 of SEQ ID NO: 1 is substituted with A; E173 of SEQ ID NO:11 corresponding to position 356 of SEQ ID NO:1 is substituted with A; M426 of SEQ ID NO:11 corresponding to position 715 of SEQ ID NO: 1 is substituted with A, F, I, Q, S, H or Y; Y427 of SEQ ID NO:11 corresponding to position 716 of SEQ ID NO: 1 is substituted with A, C, D, F, G, H or I; P428 of SEQ ID NO:11 corresponding to position 717 of SEQ ID NO:1 is substituted with A, C, F, G, S or T; and A508 of SEQ ID NO:11 corresponding to position 854 of SEQ ID NO: 1 is substituted with C, D, E, F, or L.

In one embodiment, the B-family DNA polymerase variant is derived from *Sulfolobus solfataricus* DNA polymerase (Sso) having a wild-type amino acid sequence of SEQ ID NO: 12; and wherein: D231 of SEQ ID NO:12 corresponding to position 354 of SEQ ID NO: 1 is substituted with A; E233 of SEQ ID NO: 12 corresponding to position 356 of SEQ ID NO:1 is substituted with A; L518 of SEQ ID NO:12 corresponding to position 715 of SEQ ID NO:1 is substituted with A, F, I, M, Q, S, H or Y; Y519 of SEQ ID NO:12 corresponding to position 716 of SEQ ID NO: 1 is substituted with A, C, D, F, G, H or I; P520 of SEQ ID NO:12 corresponding to position 717 of SEQ ID NO:1 is substituted with A, C, F, G, S or T; and A601 of SEQ ID NO:12 corresponding to position 854 of SEQ ID NO: 1 is substituted with C, D, E, F, or L.

The present invention further provides a kit for performing a sequencing-by-synthesis reaction, comprising: a B-family DNA polymerase variant as described above, a primer, and nucleotide analogues under conditions suitable for incorporation into the primer, thereby determining the nucleobase complementary to the nucleotide analogues incorporated in the primer.

Accordingly, the present invention relates to the specific B-family DNA polymerase variants that exhibit an improved incorporation of nucleotide analogues for synthesizing polynucleotides and sequencing the associated nucleic acid template. More particularly, the DNA sequencing-by-synthesis method can be efficiently performed by said B-family DNA polymerase variants with a normal nucleic acid template and reversible dye-terminator nucleotides to precisely determine the sequence of associated nucleic acid template.

BRIEF DESCRIPTION OF THE DRAWINGS

In order to make the above and other objects, features, advantages and embodiments of the present invention more obvious and understandable, the drawings are described as follows.

DETAILED DESCRIPTION OF THE INVENTION

Terminology

Figure 1:
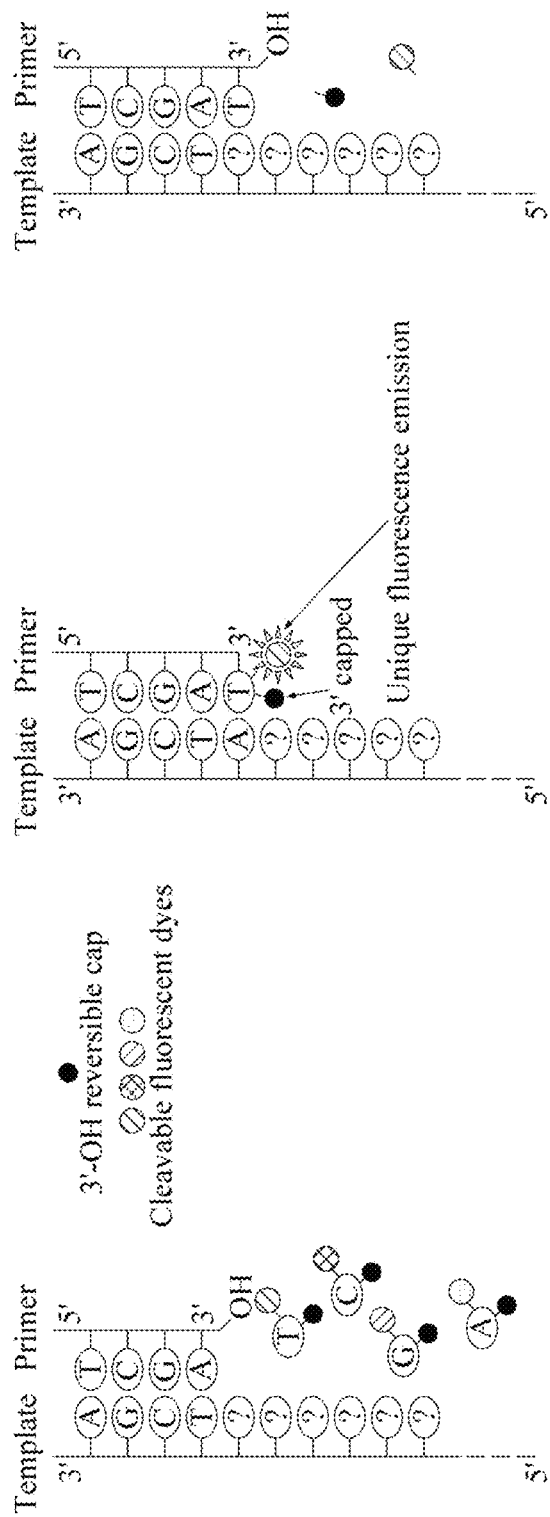
FIG. 1 illustrates a schematic diagram of a general SBS approach.

The terms used in this specification are generally within the scope of the present invention and the specific context of each term has its usual meaning in related fields. The specific terms used to describe the present invention in this specification will be described below or elsewhere in this specification, so as to help people in the industry understand the relevant description of the present invention. The same term has the same scope and meaning in the same context. In addition, there is more than one way to express the same thing; therefore, the terms discussed in this article may be replaced by alternative terms and synonyms, and whether a term is specified or discussed in this article does not have any special meaning. This article provides synonyms for certain terms, but the use of one or more synonyms does not mean that other synonyms are excluded.

As used herein, unless the context clearly indicates otherwise, "a" and "the" can also be interpreted as plural. Furthermore, titles and subtitles may be attached to the description for easy reading, but these titles do not affect the scope of the present invention.

As used herein, an "amino acid" refers to any monomer unit that can be incorporated into a peptide, polypeptide, or protein. As used herein, the term "amino acid" includes the following twenty natural or genetically encoded alpha-amino acids: alanine (Ala or A), arginine (Arg or R), asparagine (Asn or N), aspartic acid (Asp or D), cysteine (CyS or C), glutamine (Gln or Q), glutamic acid (Glu or E), glycine (Gly or G), histidine (His or H), isoleucine (Ile or I), leucine (Leu or L), lysine (Lys or K), methionine (Met or M), phenylalanine (Phe or F), proline (Pro or P), serine (Ser or S), threonine (Thr or T), tryptophan (Trp or W), tyrosine (Tyr or Y), and valine (Val or V). In cases where "X" residues are undefined, these should be defined as "any amino acid".

As used herein, the term "nucleic acid" or "polynucleotide" refers to a polymer that can be corresponded to a ribose nucleic acid (RNA) or deoxyribose nucleic acid (DNA) polymer, or an analog thereof. This includes polymers of nucleotides such as RNA and DNA, as well as synthetic forms, modified (e.g., chemically or biochemically modified) forms thereof, and mixed polymers (e.g., including both RNA and DNA subunits). Exemplary modifications include methylation, substitution of one or more of the naturally occurring nucleotides with an analog, internucleotide modifications such as uncharged linkages (e.g., methyl phosphonates, phosphotriesters, phosphoamidates, carbamates, and the like), pendentmoieties (e.g., polypeptides), intercalators (e.g., acridine, psoralen, and the like), chelators, alkylators, and modified linkages (e.g., alpha anomeric nucleic acids and the like). Also included are synthetic molecules that mimic polynucleotides in their ability to bind to a designated sequence via hydrogen bonding and other chemical interactions. Typically, the nucleotide monomers are linked via phosphodiester bonds, although synthetic forms of nucleic acids can comprise other linkages (e.g., peptide nucleic acids as described in Nielsen et al. (Science 254:1497-1500, 1991). A nucleic acid can be or can include, e.g., a chromosome or chromosomal segment, a vector (e.g., an expression vector), an expression cassette, a naked DNA or RNA polymer, the product of a polymerase chain reaction (PCR), an oligonucleotide, a probe, and a primer. A nucleic acid can be, e.g., single-stranded, double-stranded, or triple-stranded and is not limited to any particular length. Unless otherwise indicated, a particular nucleic acid sequence optionally comprises or encodes complementary sequences, in addition to any sequence explicitly indicated.

As used herein, the term "DNA sequencing by synthesis (SBS)" refers to a polymerase-dependent, next-generation sequencing (NGS) approach. As illustrated in FIG. 1, the SBS approach substantially involves the following processes: (i) incorporation of nucleotide analogues bearing labels (e.g., fluorescent reporters); optionally, the labeled nucleotides include a reversible termination property that terminates further primer extension once a nucleotide has been added to a primer; (ii) identification of the incorporated nucleotide by its labels (e.g., fluorescent emissions); and (iii) cleavage of the labels (e.g., fluorophore and/or the terminator), along with the reinitiation of the polymerase reaction for step-wise sequence determination. Some SBS embodiments include detection of a proton released upon incorporation of a nucleotide into an extension product. For example, sequencing based on detection of released protons can use an electrical detector and associated techniques that are commercially available from Ion Torrent (Guilford, CT, a Life Technologies subsidiary) or sequencing methods and systems described in US Pat. App. Pub. Nos. 2009/0026082 A1; 2009/0127589 A1; 2010/0137143 A1; or 2010/0282617 A1, each of which is incorporated herein by reference.

As used herein, the term "template" is a polynucleotide, or a polynucleotide mimic, that contains the desired or unknown target nucleotide sequence. In some instances, the terms "target sequence", "template polynucleotide", "target nucleic acid", "target polynucleotide", "nucleic acid template", "template sequence", and variations thereof, are used interchangeably. Specifically, the term "template" refers to a strand of nucleic acid on which a complimentary copy is synthesized from nucleotides or nucleotide analogues through the replication of a template-dependent or template-directed nucleic acid polymerase. Within a nucleic acid duplex, the template strand is, by the convention definition, depicted and described as the "bottom" strand. Similarly, the non-template strand is often depicted and described as the "top" strand. The "template" strand may also be referred to as the "sense" or "plus" strand and the non-template strand as the "antisense" or "minus" strand.

As used herein, the term "primer" refers to a short single-stranded oligonucleotide, a polynucleotide, or a modified nucleic acid analogue used by nucleic acid polymerase as an initiator to elongate a nucleic acid chain.

As used herein, the terms "nucleotide incorporation", "analogue incorporation", "incorporating nucleotide" and "incorporating analogue" are known to those skilled in the art and used to describe a process or reaction for nucleic acid synthesis. Thus, as used herein, the term "incorporation" is known to flexibly refer to add one, or more nucleotides, or any specified nucleic acid precursors to the 3'-hydroxyl terminus of a nucleic acid primer. For example, the nucleoside triphosphate, such as deoxyguanosine triphosphate (dGTP), is a substrate, or a precursor, for DNA synthesis by DNA polymerase. Once the dGTP is incorporated into the elongated DNA strand, it becomes a deoxyguanosine monophosphate (dGMP) moiety of the newly synthesized DNA. In other words, when a dGTP nucleotide is converted into a dGMP moiety of DNA, the person skilled in the art may say that one dGTP is incorporated into the DNA.

As used herein, the term "nucleotide analogue" is known to those of skills in the art to describe the chemically modified nucleotides or artificial nucleotides, which are structural mimics of canonical nucleotides. These nucleotide analogues can serve as substrates for nucleic acid polymerases to synthesize nucleic acid. A nucleotide analogue may have one or more altered components of a nucleotide (e.g., the phosphate backbone, pentose sugar, and nucleobase), which changes the structure and configuration of a nucleotide and affects its interactions with other nucleobases and the nucleic acid polymerases. For example, a nucleotide analogue having an altered nucleobase may confer alternative base-pairing and base-stacking properties in the DNA or RNA. Furthermore, by way of example, the modification at the base may generate various nucleosides such as inosine, methyl-5-deoxycytidine, deoxyuridine, dimethylamino-5-deoxyuridine, diamino-2,6-purine or bromo-5-deoxyuridine, and any other analogues which permits hybridization. In other exemplary aspects, modifications may take place at the level of sugar moiety (for example, replacement of a deoxyribose by an analogue), and/or at the level of the phosphate group (for example, boronate, alkylphosphonate, or phosphorothioate derivatives). A nucleotide analogue monomer may have a phosphate group selected from a monophosphate, a diphosphate, a triphosphate, a tetraphosphate, a pentaphosphate, and a hexaphosphate. Other examples of nucleotide analogues also include nucleotides having a removable blocking moiety. Examples of the removable blocking moiety include, but are not limited to, a 3'-O-blocking moiety, a base blocking moiety, and a combination thereof. Examples of the 3'-O-blocking moiety include, but are not limited to, O—$N_3$, O-azidomethyl, O-amino, O-allyl, O-phenoxyacetyl, O-methoxyacetyl, O-acetyl, O-(p-toluene)sulfonate, O-phosphate, O-nitrate, O-[4-methoxy]-tetrahydrothiopyranyl, O-tetrahydrothiopyranyl, O-[5-methyl]-tetrahydrofuranyl, O-[2-methyl, 4-methoxy]-tetrahydropyranyl, O-[5-methyl]-tetrahydropyranyl, and O-tetrahydrothiofuranyl, O-2-nitrobenzyl, O-methyl, and O-acyl. Examples of the base blocking moiety may be a reversible dye-terminator. Examples of the reversible dye-terminator include, but are not limited to, a reversible dye-terminator of Illumina MiSeq, a reversible dye-terminator of Illumina HiSeq, a reversible dye-terminator of Illumina Genome Analyzer IIX, a reversible dye-terminator of Helicos Biosciences Heliscope, and a reversible dye-terminator of LaserGen's Lightning Terminators.

As used herein, "B-family DNA polymerases (PolBs)" refers to the most common template-dependent nucleic acid polymerases or replicases in all domains of life and many DNA viruses. Like most nucleic acid polymerases, natural PolBs require a duplex primer-template DNA with a free 3'-hydroxyl (3'-OH) group at the primer terminus, all four nucleoside triphosphates (dATP, dTTP, dCTP, and dGTP), and catalytic, divalent cations ($Mg^{2+}$ or $Mn^{2+}$, etc.) for catalyzing the nucleotidyl transferase reaction of adding nucleotides to the 3'-OH terminus of a primer. The PolB enzymes, such as bacterial Pol II and archaeal B-family DNA polymerases, are replicative and repair polymerases that inherently contain a catalytic polymerase domain and a 3'→5' exonucleolytic, or proofreading, domain for removing the mis-incorporated nucleotide from the growing primer strand during nucleic acid replication. The term "3'→5' exonucleolytic domain" refers to a region of the amino acid sequence of a polymerase, which exerts the nucleic acid degradation activity from the 3'-terminus of the primer or polynucleotide chain. Coordinately, the term "catalytic polymerase domain" refers to a region of the amino acid sequence of a polymerase, which exerts the catalytic DNA/RNA polymerase activity for adding nucleotides to the 3'-terminus of a primer or polynucleotide chain.

All known structures of PolB catalytic polymerase domain resemble the shape of human right hand, where the key functional regions are characterized as fingers, palm, and thumb subdomains, respectively. The most conserved region is the palm subdomain, which contains the essential residues for catalysis. The protein sequence-alignment among various B-family DNA polymerases from different kingdoms of life and DNA viruses reveals that the PolB polymerases generally harbor six semi-conserved or conserved motifs (I-VI) for their essential exonuclease and polymerase functions. The first three sequence-motifs (Exo I, Exo II, Exo III) are in the 3'→5' exonucleolytic domain, while the other three motifs (designated as Motif A, B, and C, respectively) reside in the polymerase domain (Hopfner et al, Proc. Natl. Acad. Sci. USA 96, 3600-3605, 1999).

As used herein, the term "mutant" in the context of DNA polymerases of the present invention, means a polypeptide, typically recombinant, that comprises one or more amino acid substitutions relative to a corresponding, functional DNA polymerase.

As used herein, in the context of DNA polymerase variants, "corresponding to another sequence" (e.g., regions, fragments, nucleotide or amino acid positions, or the like) is based on the convention of numbering according to nucleotide or amino acid position number and then aligning the sequences in a manner that maximizes the percentage of sequence identity. An amino acid "corresponding to position X of specific sequence" refers to an amino acid in a polypeptide of interest that aligns with the equivalent amino acid of a specified sequence. Generally, as described herein, the amino acid corresponding to a position of a polymerase can be determined using an alignment algorithm such as BLAST. Because not all positions within a given "corresponding region" need to be identical, non-matching positions within a corresponding region may be regarded as "corresponding positions". Accordingly, as used herein, referral to an "amino acid position corresponding to amino acid position X of a specified DNA polymerase" refers to equivalent positions, based on the alignment, in other DNA polymerases and structural homologues and families.

As used herein, the term "semi-conserved" used herein refers to the segment of polymerase that has a similar property of amino acid residue or an identical amino acid residue in the homologous position of different PolBs from various sources. The term "conserved" means the segment of polymerase having the same amino acid residue in the homologous position of different PolBs from various sources.

As used herein, the term "consensus sequence of SEQ ID NO: 1" used herein refers to a reference sequence comprising the conserved amino acids of cross-species B-family DNA polymerase. The consensus sequence of SEQ ID NO: 1 is a virtual sequence and is generated by aligning the following 16 wild type B-family DNA polymerases to obtain the conserved amino acids: *Thermococcus gorgonarius* DNA polymerase (Tgo), *Thermococcus kodakarensis* DNA polymerase (Kod1), *Thermococcus* sp. (strain 9° N-7) DNA polymerase (9° N), *Pyrococcus furiosus* DNA polymerase (Pfu), *Thermococcus litoralis* DNA polymerase (Vent), *Methanococcus maripaludis* DNA polymerase (Mma), *Methanosarcina acetivorans* DNA polymerase (Mac), human DNA polymerase delta catalytic p125 subunit (hPOLD), *Saccharomyces cerevisiae* DNA polymerase delta catalytic subunit (ScePOLD), *Pyrobaculum islandicum*

DNA polymerase (Pis), *Sulfolobus solfataricus* DNA polymerase (Sso), *Pseudomonas aeruginosa* DNA polymerase II (Pae), *Escherichia coli* DNA polymerase II (Eco), Bacteriophage (*Escherichia* phage) RB69 DNA polymerase (RB69), Bacteriophage (*Escherichia* phage) T4 DNA polymerase (T4), and Bacteriophage (*Bacillus* phage) Phi29 DNA polymerase (Phi29). The positions of motifs Exo I, Exo II, Exo III, Motif A, B, and C are defined by the inventor using the consensus sequence of SEQ ID NO: 1 of the present invention; therefore, it shall be noted that the positions of these motifs defined in the present invention are not totally the same as those described in the prior art.

Objectives

In general, to be considered and ultimately applied for a SBS approach, the DNA polymerase should possess the following properties: (i) The polymerase must be a DNA-dependent DNA polymerase; in other words, the polymerase requires a DNA template for replication. (ii) The polymerase should rapidly incorporate nucleotides; DNA polymerases with a faster nucleotide incorporation rate can catalyze DNA synthesis much more efficiently. (iii) The polymerase must have a high replicative fidelity to minimize systematic errors; in other words, the polymerase should be able to accurately read DNA template sequence information and faithfully incorporate the correct, matched nucleotides along the DNA template. (iv) The polymerase should possess a long, intrinsic, and replicative processivity. As used herein, the processivity of DNA polymerase is defined as the number of dNTP or the nucleotide analogue incorporated during complex formation with a primer/template (P/T) DNA. (v) The polymerase should function as a monomer, for that it can be produced and further modified more easily (Chen, C. Y. DNA Polymerases Drive DNA Sequencing-by-Synthesis Technologies: Both Past and Present. *Front. Microbiol.* 2014; 5:305. doi: 10.3389/fmicb.2014.00305).

Therefore, one objective of the subject application is to provide B-family DNA polymerase (PolB) variants based on the above rationale, so that the PolB variants have an improved incorporation efficiency of nucleotide analogues for synthesizing polynucleotides and sequencing the associated nucleic acid template. The aforesaid enzymatic nucleic acid synthesis and sequencing can be efficiently performed by these PolB variants in the presence of a nucleic acid template and nucleotide analogues. More particularly, the aforesaid enzymatic nucleic acid synthesis and sequencing can be efficiently performed by these PolB variants with a normal nucleic acid template and reversible dye-terminator nucleotides to precisely determine the sequence of this associated nucleic acid template. For instance, the PolB variants may depend on a normal, unmodified nucleic acid template to direct synthesis and incorporation of modified nucleotide analogues to the 3'-terminus of primer. The incorporated nucleotide carrying a distinct fluorescent reporter can be used to determine the DNA sequence information of the nucleic acid template.

The inventor has discovered that the PolB variants have a broader substrate specificity, which means the altered PolB variants can utilize not only naturally occurring nucleotides, but also varieties of modified nucleotides for the template-dependent nucleic acid synthesis. Therefore, these PolB variants may improve the nucleotide-incorporation efficiency in the DNA sequencing-by-synthesis method to determine the sequence of nucleic acids.

B-Family DNA Polymerase Variant

Therefore, provided herein are altered polymerase, which is described based on the amino acid sequence of the consensus sequence of SEQ ID NO: 1. An altered polymerase includes substitution mutations at one or more residues when compared to the consensus sequence of SEQ ID NO: 1. A substitution mutation can be at the same position or a functionally equivalent position compared to the consensus sequence of SEQ ID NO: 1. The skilled person will readily appreciate that an altered polymerase described herein is not naturally occurring. Therefore, an altered polymerase described herein is based on the consensus sequence of SEQ ID NO: 1 and further includes substitution mutations at one or more residues. In one embodiment, a substitution mutation is at a position functionally equivalent to an amino acid of the consensus sequence of SEQ ID NO: 1. "Functionally equivalent" means that the altered polymerase has the amino acid substitution at the amino acid position in the consensus sequence of SEQ ID NO: 1 that has the same functional role in both the consensus sequence and the altered polymerase.

In general, functionally equivalent substitution mutations in two or more different polymerases occur at homologous amino acid positions in the amino acid sequences of the polymerases. Hence, "functionally equivalent" also encompasses mutations that are "positionally equivalent" or "homologous" to a given mutation, regardless of whether the particular function of the mutated amino acid is known. It is possible to identify the locations of functionally equivalent and positionally equivalent amino acid residues in the amino acid sequences of two or more different polymerases on the basis of sequence alignment and/or molecular modelling. For instance, the amino acid sequence-alignment of 16 wild-type B-family DNA polymerases to identify positionally equivalent and/or functionally equivalent residues is set forth in FIG. 2. Thus, for the exemplary residue 141 of the Tgo, Kod1, 9° N, Pfu, and Vent DNA polymerases and the residue 198 of the Mac DNA polymerase are functionally equivalent and positionally equivalent. Likewise, for the exemplary residue 143 of the Tgo, Kod1, 9° N, Pfu, and Vent DNA polymerases and the residue 200 of the Mac polymerase are functionally equivalent and positionally equivalent. The skilled person can easily identify functionally equivalent residues in other DNA polymerases.

In accordance with some embodiments of the present invention, the provided B-family DNA polymerase variant comprising: a motif Exo I, a motif Exo II, a motif Exo III, a motif A, a motif B, and a motif C corresponding respectively to positions 349 to 364, 450 to 476, 590 to 608, 706 to 730, 843 to 855, and 940 to 956 of the consensus sequence of SEQ ID NO:1; at least one amino acid substitution (one or more amino acid substitutions, or a combination of amino acid substitutions) at positions residing in the motif Exo I, the motif Exo II, and the motif Exo III; and at least one amino acid substitution (one or more amino acid substitutions, or a combination of amino acid substitutions), at positions residing in the motif A, the motif B, and the motif C.

In accordance with some embodiments of the present invention, the B-family DNA polymerase variant is modified from a wild-type B-family DNA polymerase having an amino acid sequence selected from the group consisting of SEQ ID NO: 2, 3, 4, 5, 6, 7, 8, 9, 10, 11, 12, 13, 14, 15, 16 and 17, which are derived from the wild-type B-family DNA polymerase including *Thermococcus gorgonarius* DNA polymerase (Tgo), *Thermococcus kodakarensis* DNA polymerase (Kod1), *Thermococcus* sp. (strain 9° N-7) DNA polymerase (9° N), *Pyrococcus furiosus* DNA polymerase (Pfu), *Thermococcus litoralis* DNA polymerase (Vent), *Methanococcus maripaludis* DNA polymerase (Mma), *Methanosarcina acetivorans* DNA polymerase (Mac), human DNA polymerase delta catalytic p125 subunit (hPOLD), *Saccharomyces cerevisiae* DNA polymerase delta catalytic subunit (ScePOLD), *Pyrobaculum islandicum* DNA polymerase (Pis), *Sulfolobus solfataricus* DNA polymerase (Sso), *Pseudomonas aeruginosa* DNA polymerase II (Pae), *Escherichia coli* DNA polymerase II (Eco), Bacteriophage (*Escherichia*) phage RB69 DNA polymerase (RB69), Bacteriophage (*Escherichia* phage) T4 DNA polymerase (T4), or Bacteriophage (*Bacillus* phage) Phi29 DNA polymerase (Phi29), respectively.

In accordance with some embodiments of the present invention, the amino acid corresponding to position 354 of SEQ ID NO:1 is any amino acid other than D; for example, said amino acid can be substituted with N, Q, S, T, Y, A, C, G, I, L, M, F, P, W, V, R, H, K or E. The amino acid corresponding to position 355 of SEQ ID NO:1 is any amino acid other than I; for example, said amino acid can be substituted with N, Q, S, T, Y, A, C, G, L, M, F, P, W, R, H, K, D or E. The amino acid corresponding to position 356 of SEQ ID NO:1 is any amino acid other than E; for example, said amino acid can be substituted with N, Q, S, T, Y, A, C, G, I, L, M, F, P, W, V, R, H, K or D. The amino acid corresponding to position 715 of SEQ ID NO: 1 is any amino acid other than L or M; for example, said amino acid can be substituted with N, Q, S, T, Y, A, C, G, I, F, P, W, V, R, H, K, D or E. The amino acid corresponding to position 716 of SEQ ID NO:1 is any amino acid other than Y; for example, said amino acid can be substituted with N, Q, S, T, A, C, G, I, L, M, F, P, W, V, R, H, K, D or E. The amino acid of corresponding to position 717 of SEQ ID NO:1 is any amino acid other than P; for example, said amino acid can be substituted with N, Q, S, T, Y, A, C, G, I, L, M, F, W, V, R, H, K, D or E. In a preferred embodiment of the present invention, the amino acid corresponding to position 854 of SEQ ID NO:1 is any amino acid other than A; for example, said amino acid can be substituted with N, Q, S, T, Y, C, G, I, L, M, F, P, W, V, R, H, K, D or E.

In accordance with some embodiments of the present invention, the B-family DNA polymerase variant is derived from *Thermococcus kodakarensis* DNA polymerase (Kod1) having a wild-type amino acid sequence of SEQ ID NO:3; and wherein: D141 of SEQ ID NO:3 corresponding to position 354 of SEQ ID NO:1 is substituted with A; E143 of SEQ ID NO:3 corresponding to position 356 of SEQ ID NO:1 is substituted with A; L408 of SEQ ID NO:3 corresponding to position 715 of SEQ ID NO:1 is substituted with A, F, I, M, Q, S, H or Y, preferably A, Q or Y, more preferably Y; Y409 of SEQ ID NO:3 corresponding to position 716 of SEQ ID NO:1 is substituted with A, C, D, F, G, H or I, preferably A; and P410 of SEQ ID NO:3 corresponding to position 717 of SEQ ID NO:1 is substituted with A, C, F, G, S or T, preferably F or G, more preferably G. In certain embodiments, A485 of SEQ ID NO:3 corresponding to position 854 of SEQ ID NO: 1 is substituted with C, D, E, F, or L, preferably E or L, more preferably L.

In accordance with some embodiments of the present invention, the B-family DNA polymerase variant is derived from *Thermococcus* sp. (strain 9° N-7) DNA polymerase (9° N) having a wild-type amino acid sequence of SEQ ID NO:4; and wherein: D141 of SEQ ID NO:4 corresponding to position 354 of SEQ ID NO:1 is substituted with A; E143 of SEQ ID NO:4 corresponding to position 356 of SEQ ID NO:1 is substituted with A; L408 of SEQ ID NO:4 corresponding to position 715 of SEQ ID NO:1 is substituted with A, F, I, M, Q, S, H or Y, preferably A, Q or Y, more preferably Y; Y409 of SEQ ID NO:4 corresponding to position 716 of SEQ ID NO:1 is substituted with A, C, D, F, G, H or I, preferably A; and P410 of SEQ ID NO:4 corresponding to position 717 of SEQ ID NO: 1 is substituted with A, C, F, G, or S or T, preferably F or G, more preferably G. In certain embodiments, A485 of SEQ ID NO:4 corresponding to position 854 of SEQ ID NO:1 is substituted with C, D, E, F, or L, preferably E or L, more preferably L.

In accordance with some embodiments of the present invention, the B-family DNA polymerase variant is derived from *Pyrococcus furiosus* DNA polymerase (Pfu) having a wild-type amino acid sequence of SEQ ID NO:5; and wherein: D141 of SEQ ID NO:5 corresponding to position 354 of SEQ ID NO:1 is substituted with A; E143 of SEQ ID NO:5 corresponding to position 356 of SEQ ID NO:1 is substituted with A; L409 of SEQ ID NO:5 corresponding to position 715 of SEQ ID NO: 1 is substituted with A, F, I, M, Q, S, H or Y, preferably A, Q or Y, more preferably Y; Y410 of SEQ ID NO:5 corresponding to position 716 of SEQ ID NO:1 is substituted with A, C, D, F, G, H or I, preferably A; and P411 of SEQ ID NO:5 corresponding to position 717 of SEQ ID NO:1 is substituted with A, C, G, F, S or T, preferably F or G, more preferably G. In certain embodiments, A486 of SEQ ID NO:5 corresponding to position 854 of SEQ ID NO:1 is substituted with C, D, E, F, or L, preferably E or L, more preferably L.

In accordance with some embodiments of the present invention, the B-family DNA polymerase variant is derived from *Thermococcus litoralis* DNA polymerase (Vent) having a wild-type amino acid sequence of SEQ ID NO:6; and wherein: D141 of SEQ ID NO:6 corresponding to position 354 of SEQ ID NO:1 is substituted with A; E143 of SEQ ID NO:6 corresponding to position 356 of SEQ ID NO: 1 is substituted with A; L411 of SEQ ID NO:6 corresponding to position 715 of SEQ ID NO:1 is substituted with A, F, I, M, Q, S, H or Y, preferably A, Q or Y, more preferably Y; Y412 of SEQ ID NO:6 corresponding to position 716 of SEQ ID NO:1 is substituted with A, C, D, F, G, H or I, preferably A; and P413 of SEQ ID NO:6 corresponding to position 717 of SEQ ID NO:1 is substituted with A, C, F, G, S or T, preferably F or G, more preferably G. In certain embodiments, A488 of SEQ ID NO:6 corresponding to position 854 of SEQ ID NO:1 is substituted with C, D, E, F, or L, preferably E or L, more preferably L.

In accordance with some embodiments of the present invention, the B-family DNA polymerase variant is derived from *Methanosarcina acetivorans* DNA polymerase (Mac) having a wild-type amino acid sequence of SEQ ID NO:8; and wherein: D198 of SEQ ID NO:8 corresponding to position 354 of SEQ ID NO: 1 is substituted with A; E200 of SEQ ID NO:8 corresponding to position 356 of SEQ ID NO:1 is substituted with A; L485 of SEQ ID NO:8 corresponding to position 715 of SEQ ID NO:1 is substituted with A, F, I, M, Q, S, H or Y, preferably A, Q or Y, more preferably Y; Y486 of SEQ ID NO:8 corresponding to position 716 of SEQ ID NO: 1 is substituted with A, C, D, F, G, H or I, preferably A; and P487 of SEQ ID NO:8 corresponding to position 717 of SEQ ID NO:1 is substituted with A, C, F, G, S or T, preferably F or G, more preferably G. In certain embodiments, A565 of SEQ ID NO:8 corresponding to position 854 of SEQ ID NO:1 is substituted with C, D, E, F, or L, preferably E or L, more preferably L.

In accordance with some embodiments of the present invention, the B-family DNA polymerase variant is derived from *Pyrobaculum islandicum* DNA polymerase (Pis) having a wild-type amino acid sequence of SEQ ID NO:11; and wherein: D171 of SEQ ID NO:11 corresponding to position 354 of SEQ ID NO:1 is substituted with A; E173 of SEQ ID NO:11 corresponding to position 356 of SEQ ID NO:1 is substituted with A; M426 of SEQ ID NO:11 corresponding to position 715 of SEQ ID NO:1 is substituted with A, F, I, Q, S, H or Y, preferably A, Q or Y, more preferably Y; Y427 of SEQ ID NO:11 corresponding to position 716 of SEQ ID NO: 1 is substituted with A, C, D, F, G, H or I, preferably A; and P428 of SEQ ID NO: 11 corresponding to position 717 of SEQ ID NO:1 is substituted with A, C, F, G, S or T, preferably F or G, more preferably G. In certain embodiments, A508 of SEQ ID NO:11 corresponding to position 854 of SEQ ID NO:1 is substituted with C, D, E, F, or L, preferably E or L, more preferably L.

In accordance with some embodiments of the present invention, the B-family DNA polymerase variant is derived from *Sulfolobus solfataricus* DNA polymerase (Sso) having a wild-type amino acid sequence of SEQ ID NO: 12; and wherein: D231 of SEQ ID NO:12 corresponding to position 354 of SEQ ID NO:1 is substituted with A; E233 of SEQ ID NO:12 corresponding to position 356 of SEQ ID NO:1 is substituted with A; L518 of SEQ ID NO:12 corresponding to position 715 of SEQ ID NO:1 is substituted with A, F, I, M, Q, S, H or Y, preferably A, Q or Y, more preferably Y; Y519 of SEQ ID NO:12 corresponding to position 716 of SEQ ID NO:1 is substituted with A, C, D, F, G, H or I, preferably A; an P520 of SEQ ID NO: 12 corresponding to position 717 of SEQ ID NO:1 is substituted with A, C, F, G, S or T, preferably F or G, more preferably G. In certain embodiments, A601 of SEQ ID NO: 12 corresponding to position 854 of SEQ ID NO:1 is substituted with C, D, E, F, or L, preferably E or L, more preferably L.

Mutating Polymerases

Various types of mutagenesis techniques are optionally used in the present disclosure, e.g., to modify polymerases to produce the variants of the subject application, or using random or semi-random mutational approaches. In general, any available mutagenesis procedure can be used for making polymerase mutants. Such mutagenesis procedures optionally include selection of mutant nucleic acids and polypeptides for one or more activity of interest. Procedures that can be used include, but are not limited to: the site-directed point mutagenesis, random point mutagenesis, in vitro or in vivo homologous recombination (DNA shuffling and combinatorial overlap PCR), mutagenesis using uracil containing templates, oligonucleotide-directed mutagenesis, phosphorothioate-modified DNA mutagenesis, mutagenesis using gapped duplex DNA, point mismatch repair, mutagenesis using repair-deficient host strains, restriction-selection and restriction-purification, deletion mutagenesis, mutagenesis by total gene synthesis, degenerate PCR, double-strand break repair, and many others known to skilled person.

Nucleic Acids Encoding the DNA Polymerase Variant

Nucleic acids encoding the DNA polymerase variant of disclosed herein are also a feature of embodiments presented herein. A particular amino acid can be encoded by multiple codons, and certain translation systems (e.g., prokaryotic or eukaryotic cells) often exhibit codon bias, e.g., different organisms often prefer one of the several synonymous codons that encode the same amino acid. As such, nucleic acids presented herein are optionally "codon optimized," meaning that the nucleic acids are synthesized to include codons that are preferred by the particular translation system being employed to express the polymerase. For example, when it is desirable to express the polymerase in a bacterial cell (or even a particular strain of bacteria), the nucleic acid can be synthesized to include codons most frequently found in the genome of that bacterial cell, for efficient expression of the polymerase. A similar strategy can be employed when it is desirable to express the polymerase in a eukaryotic cell, e.g., the nucleic acid can include codons preferred by that eukaryotic cell.

The nucleic acid molecules described herein may also, advantageously, be included in a suitable expression vector to express the polymerase proteins encoded therefrom in a suitable host. Incorporation of cloned DNA into a suitable expression vector for subsequent transformation of said cell and subsequent selection of the transformed cells is well known to those skilled in the art. Such an expression vector includes a vector having a nucleic acid according to the embodiments presented herein operably linked to regulatory sequences, such as promoter regions, that are capable of effecting expression of said DNA fragments. Such vectors may be transformed into a suitable host cell to provide for the expression of the B-family DNA polymerase variants according to the embodiments presented herein.

The nucleic acid molecule may encode a mature protein or a protein having a prosequence, including that encoding a leader sequence on the preprotein which is then cleaved by the host cell to form a mature protein. The vectors may be, for example, plasmid, virus or phage vectors provided with an origin of replication, and optionally a promoter for the expression of said nucleotide and optionally a regulator of the promoter. The vectors may contain one or more selectable markers, such as, for example, an antibiotic resistance gene.

Compositions Including the B-Family DNA Polymerase Variant

The present disclosure also provides compositions that include the B-family DNA polymerase variant described herein. The composition can include other components in addition to the B-family DNA polymerase variant. For example, the composition can include a buffer, a nucleotide solution, or a combination thereof. The nucleotide solution can include nucleotides, such as nucleotides that are labelled, synthetic, modified, or a combination thereof. In one embodiment, a composition includes target nucleic acids, such as a library of target nucleic acids.

Kit for Performing SBS Reaction

The present invention further provides a kit for performing a sequencing-by-synthesis reaction, comprising: at least one B-family DNA polymerase variant as described above, a primer, a polynucleotide template, and nucleotide analogues under conditions suitable for incorporation into the primer, thereby determining the templating nucleobase complementary to the incorporated nucleotide at the primer terminus. Optionally, other reagents such as buffers and solutions required for the B-family DNA polymerase variant and nucleotide solution are also included. Instructions for use of the assembled or packaged components are also typically included.

In certain embodiments, the nucleotide solution includes labelled nucleotides. In certain embodiments, the nucleotides are synthetic nucleotides. In certain embodiments, the nucleotides are chemically modified nucleotides. In certain embodiments, a modified nucleotide has an altered chemical group at the 3' sugar hydroxyl such that the substituent is larger in size than the naturally occurring 3' hydroxyl group. In certain embodiments, the modified nucleotides include a modified nucleotide or nucleoside molecule that includes a purine or pyrimidine base and a ribose or deoxyribose sugar moiety having a removable 3'-blocking group covalently attached thereto. In certain embodiments, the modified nucleotides are fluorescently labelled to allow direct detection. In certain embodiments, the modified nucleotides include a nucleotide or nucleoside having a base attached to a detectable label via a cleavable linker. In certain embodiments, the detectable label includes a fluorescent label.

Method of Use

The present invention further provides a method for incorporating nucleotide analogues into DNA comprising allowing the following components to interact: (i) B-family DNA polymerase variant according to any of the above embodiments, (ii) a DNA template; and (iii) a nucleotide solution. In certain embodiments, the DNA template comprises a clustered array on a glass or silicon wafer. Thus, a multiplexing, parallel nucleic acid synthesis and sequencing can be performed to determine the sequences of various nucleic acids. The PolB variant driven and array-based sequencing-by-synthesis method can increase the throughput of DNA sequencing and drive down the overall costs of DNA sequencing.

In certain embodiments, the PolB variants described herein can be used to incorporate the nucleotide conjugates or analogue covalently linked with an enzyme, an antibody, a chemical group, such as a biotin, a desthiobiotin, or a fluorophore on the base, phosphate moiety, or pentose sugar of nucleotide, to the 3'-terminus of the primer or nucleic acids initiator in a template-dependent synthesis manner, respectively.

The incorporation of these nucleotide conjugates or analogues into the nucleic acids by PolB variants during the nucleic acid synthesis concurrently add the desired component, such as an enzyme, an antibody, or a chemical group to the newly synthesized nucleic acids in a sequence-dependent manner. Common components used to label or generate nucleic acid probes and conjugates are known in the art, which include, but are not limited to, nucleotide analogues, modified linkers, such as a biotin, a thiol, an azidoor an amine group, fluorophores, enzymes, and antibodies.

Alternatively, in other embodiments, the post-synthetic modifications of nucleic acids can be achieved by covalently or non-covalently coupling with an enzyme, an antibody, a chemical group, or a fluorophore via a modified linker on the base, phosphate moiety, or pentose sugar of synthetic nucleotide. As a result, the desired component can be covalently or non-covalently associated with the specific base, which is added to the 3'-terminus of newly synthesized polynucleotides. The base-specific conjugate can be used as a reporter to determine the sequence of nucleic acid template.

Still, in some embodiments, the PolB variants described herein can be used in the sequencing-by-synthesis method to incorporate the 3'-modified reversible dye-terminator (RDT) nucleotide, which bears a cleavable chemical substitution at the 3'-hydroxyl group (3'-OH) on the nucleotide sugar moiety and a removable fluorophore molecule on the nucleotide base with a distinct fluorescent spectrum. The template-directed synthesis and individual RDT-nucleotide incorporation by the PolB variants can be used as a fluorescent readout for A, T, C, or G base, respectively, to determine the sequence of associated nucleic acids template.

EXAMPLES

In this section, the contents of the present invention will be described in detail through the following examples. These examples are for illustration only, and those skilled in the art can easily think of various modifications and changes. As such, various embodiments of the present invention will be described in detail below, while the invention is not limited to said various embodiments listed in this specification.

Example 1

Figure 2:
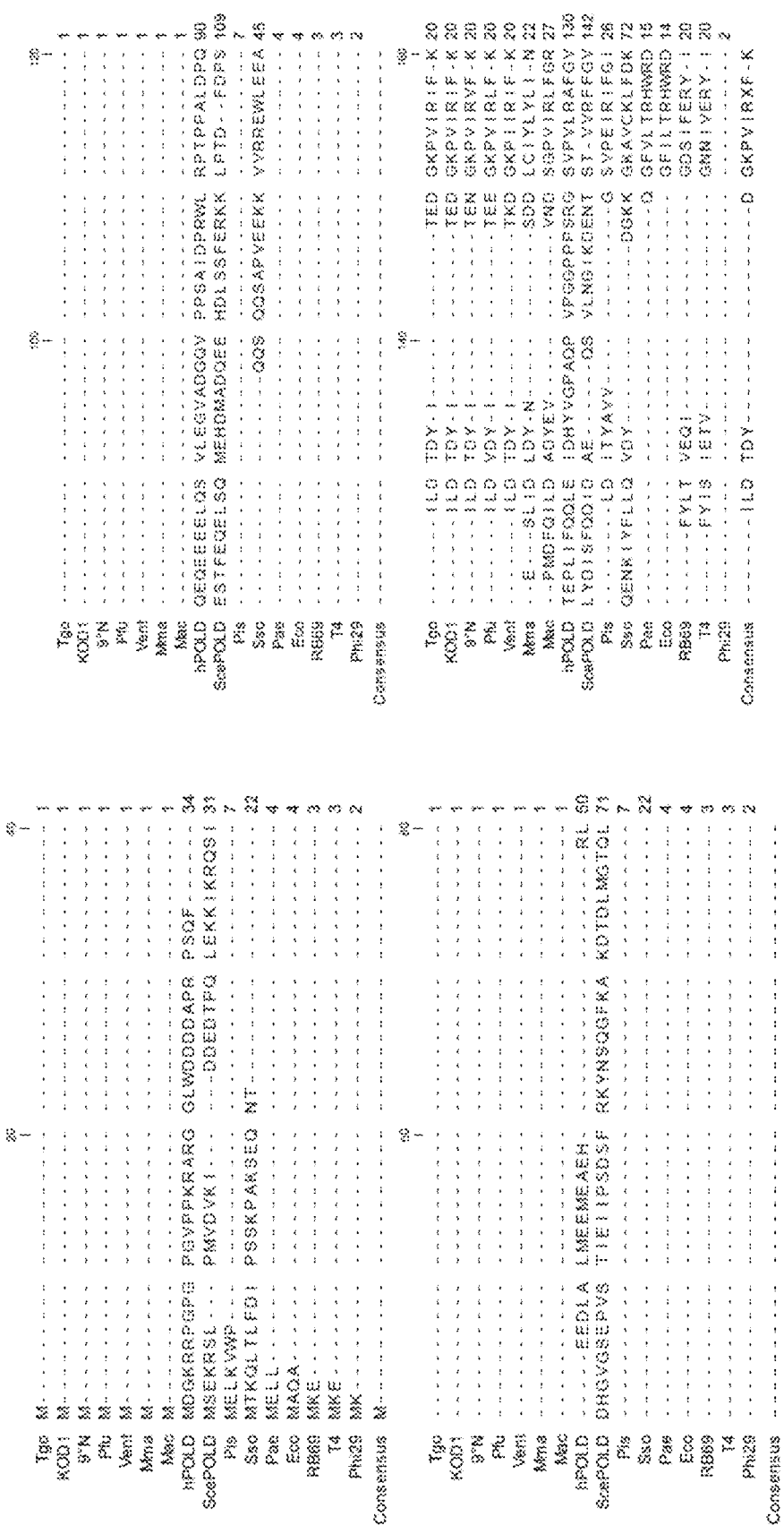
FIG. 2 shows an amino acid sequence alignment of various wild-type B-family DNA polymerases (PolB) related to the present invention and their consensus sequence.
Figure 2:
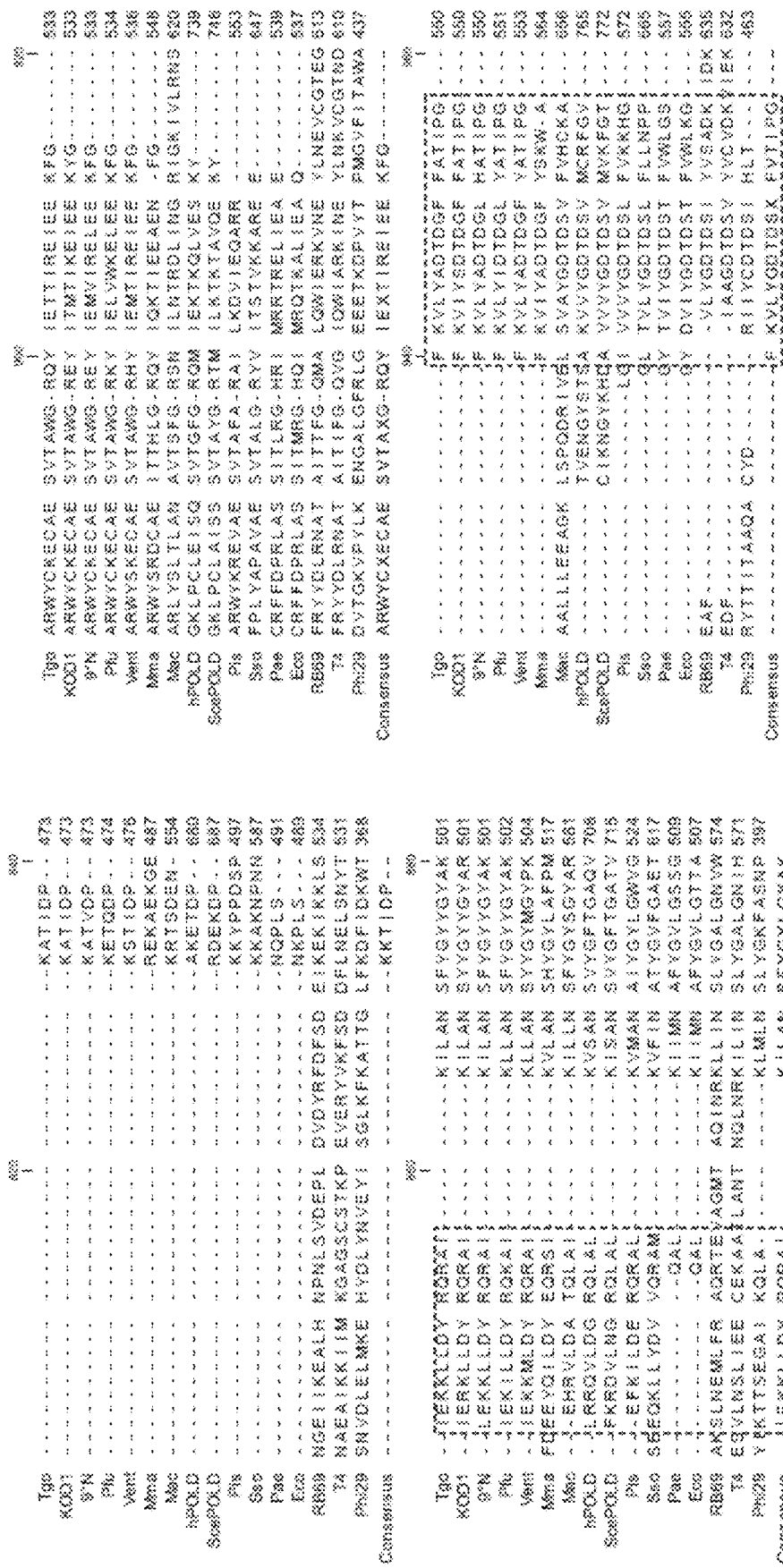
Figure 2:
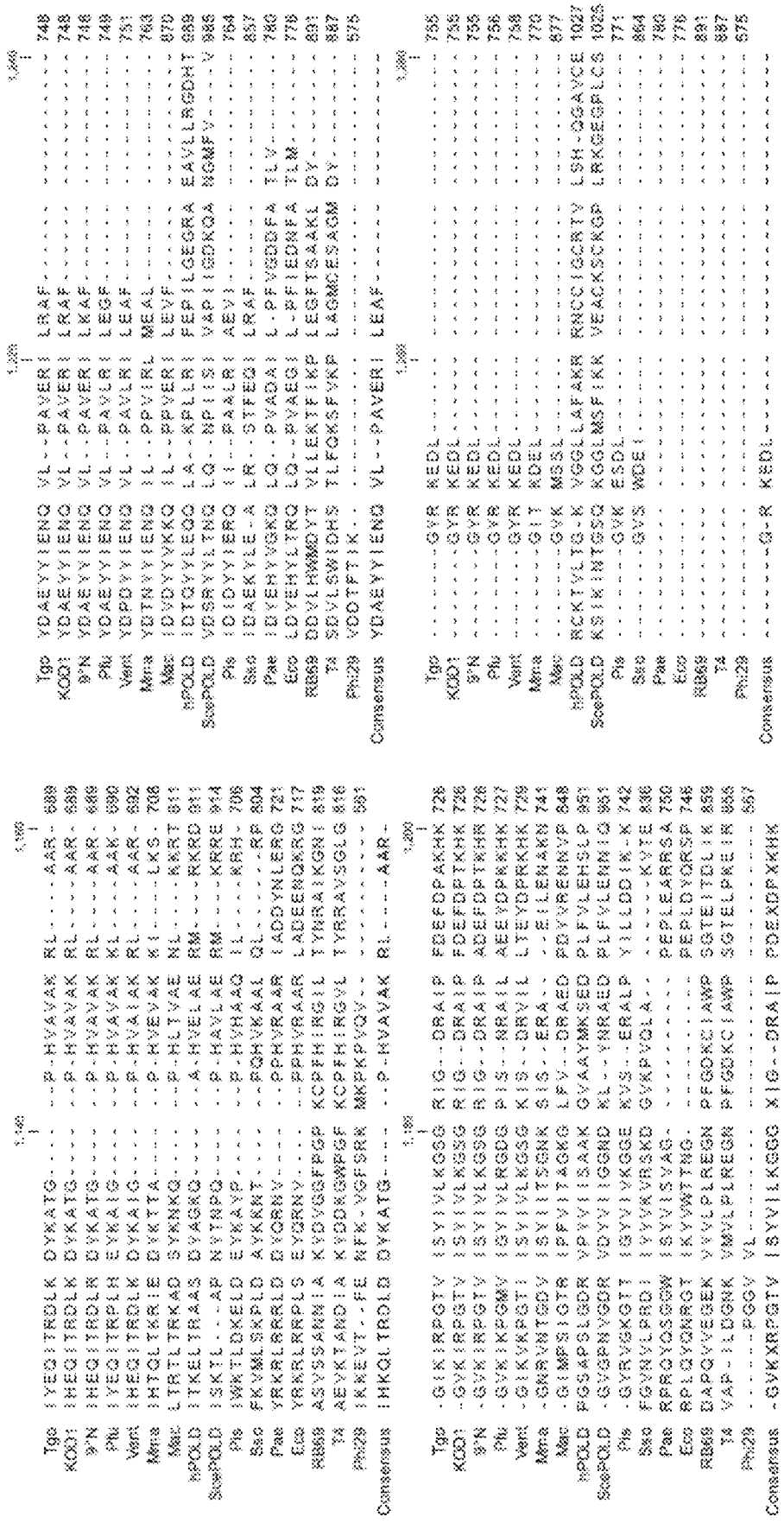

Protein Sequence Alignment of Various B-Family DNA Polymerases and Determination of Consensus Sequences and Variants FIG. 2 shows the amino acid sequence alignment of 16 wild-type B-family DNA polymerases (PolB) and the outcome of aligned consensus sequence is listed in the bottom (SEQ ID NO:1). The 16 wild-type B-family DNA polymerases being aligned are *Thermococcus gorgonarius* DNA polymerase (Tgo, SEQ ID NO:2), *Thermococcus kodakarensis* DNA polymerase (Kod1, SEQ ID NO:3), *Thermococcus* sp. (strain 9° N-7) DNA polymerase (9° N, SEQ ID NO:4), *Pyrococcus furiosus* DNA polymerase (Pfu, SEQ ID NO:5), *Thermococcus litoralis* DNA polymerase (Vent, SEQ ID NO:6), *Methanococcus maripaludis* DNA polymerase (Mma, SEQ ID NO:7), *Methanosarcina acetivorans* DNA polymerase (Mac, SEQ ID NO:8), human DNA polymerase delta catalytic p125 subunit (hPOLD, SEQ ID NO:9), *Saccharomyces cerevisiae* DNA polymerase delta catalytic subunit (ScePOLD, SEQ ID NO:10), *Pyrobaculum islandicum* DNA polymerase, (Pis, SEQ ID NO:11) *Sulfolobus solfataricus* DNA polymerase (Sso, SEQ ID NO:12), *Pseudomonas aeruginosa* DNA polymerase II (Pae, SEQ ID NO:13), *Escherichia coli* DNA polymerase II (Eco, SEQ ID NO:14), Bacteriophage RB69 DNA polymerase (RB69, SEQ ID NO:15), Bacteriophage T4 DNA polymerase (T4, SEQ ID NO:16), and Bacteriophage Phi29 DNA polymerase (Phi29, SEQ ID NO:17).

As shown in FIG. 2, various regions of wild-type PolBs are highly conserved while other regions are more variable. Those of skill in the art will immediately recognize and understand that mutations in addition to those specifically identified and discussed herein may be also made in the variable regions of wild-type PolBs without altering, or without substantially altering, the polymerase activity of the mutated enzyme. Likewise, conservative mutations at conserved residues/positions of PolB may be made without altering, or substantially altering, the polymerase activity of the mutated enzyme. Enzyme engineering based on comparative structure analysis with other functionally related enzymes or homologs is a common and useful technique in the molecular biology field that allows a person of skill to reasonably predict the effect of a given mutation on the catalytic activity of the enzyme. Using the structural data and known physical properties of amino acids, those of skill in the art can mutate enzymes, such as the DNA polymerases encompassed by the present invention, without altering, or without substantially altering, the essential, intrinsic characteristics of the enzymes.

Besides, the motif Exo I, motif Exo II, motif Exo III, motif A, motif B, and motif C regions corresponding respectively to positions 349 to 364, 450 to 476, 590 to 608, 706 to 730, 843 to 855, and 940 to 956 of the consensus sequence of SEQ ID NO:1 are marked in FIG. 2. More specifically, the polymerase variant in the present invention is based on substitution mutations at one or more residues correspondingly residing in said motifs.

Example 2

Creating B-Family DNA Polymerase Variants

Gene synthesis approach and mutagenesis technique are adapted to create exemplary PolB variants according to the properties of conserved/consensus amino acids in the conserved and semi-conserved regions of selective PolBs, which are disclosed herein. For instance, the site-directed mutagenesis approach, which is well-known approach to those skilled in the art, is conducted to change the amino acid residues in the conserved motif Exo I, motif Exo II, motif Exo III, motif A, motif B, and motif C regions of an exemplary wild-type PolB, respectively.

In some embodiments, the procedure for obtaining DNA polymerase variants is generally divided into three steps: Step 1: Gene synthesis of DNA polymerase and its exonuclease-deficient (Exo) mutant, Step 2: Construction of DNA polymerase variant in the desired region, and Step 3: Expression and purification of DNA polymerase and its variants. As described in more detail below, the techniques used in said procedure are well-known to those skilled in the art.

In Step 1, the codon-optimized gene fragment encoding the wild-type, intron-free DNA polymerase is synthesized by Genomics BioSci & Tech Co. (New Taipei City, Taiwan). The 3' to 5' exonuclease-deficient DNA polymerase (designated as Exo⁻) is also provided by the same vendor. By "Exo⁻" as used herein, it means that wild-type PolBs has combinatory mutations at the positions corresponding to D354 of SEQ ID NO: 1, which is substituted with an Alanine (D354A) residue, and E356 of SEQ ID NO: 1, which is also substituted with an Alanine residue (E356A), respectively.

In Step 2, the synthetic wild-type and 3' to 5' exonuclease-deficient DNA polymerase gene are respectively subcloned into the pET28b vector using the NdeI and NotI sites. The sequences of recombinant plasmids are confirmed by DNA sequencing. To create the polymerase variant at the desired motif region of the PolB protein backbone⁻, the site-directed mutagenesis, is conducted. Briefly, the site-directed mutagenesis PCR was performed with the recombinant plasmids using the Q5 Site-directed Mutagenesis Kit from New England Biolabs (Ipswich, MA) to introduce the amino acid substitution. The products are first analyzed by 1% agarose gel to confirm the amplicon size and the rest of PCR reaction mixture is then treated with DpnI at 37° C. for an hour. The mixture is further incubated at 70° C. for 10 mins to inactivate the DpnI function. The DpnI-treated PCR reaction mixture is then purified by the Qiagen's QIAquick PCR Purification Kit (Whatman, MA). The purified DNA fragment is treated with the mixture of T4 PNK and T4 DNA ligase. The re-circularized PCR-amplified DNA is transformed back into the E. coli cells. The plasmid DNA was later extracted from the E. coli cells using the Qiagen Plasmid Mini Kit (Whatman, MA). The mutagenic sequences of the polymerase variants at the desired motif region, or regions, are confirmed by DNA sequencing.

In Step 3, E. coli Acella cells harboring the plasmid DNA carrying specific polymerase variant gene are grown in 2 L of LB medium supplemented with 0.5% glucose and 50 µg/ml carbenicillin at 37° C. When the cell density reaches an absorbance value at $OD_{600nm}$ around 0.6~0.8, an 1 mM of isopropyl β-D-1-thiogalactopyranoside (IPTG) is added to induce protein expression. Cells are grown for additional 4 hours at 37° C. and then harvested by centrifugation at 4° C. for 10 min at 7,000×g. Cell pellets are resuspended with buffer A [50 mM Tris-HCl (pH 7.5), 300 mM NaCl, 0.5 mM EDTA, 1 mM DTT, 5% (v/v) glycerol] containing 1 mM benzamidine hydrochloride. Cell lysis is achieved by incubation with 50 mg lysozyme on ice for 1 hour followed by sonication. The cell lysate is clarified by centrifugation at 18,000×g for 25 min at 4° C. The clarified crude cell extract is incubated at 70° C. for 30 minutes and then cooled down at 4° C. The heat-treated cell extract is further clarified by centrifugation at 18,000×g for 25 minutes at 4° C. After centrifugation, the supernatant is diluted with buffer A without NaCl and loaded onto a HiTrap Heparin column (Cytiva Life Sciences, Marlborough, MA, USA) pre-equilibrated in buffer A in the ÄKTA pure chromatography system (Cytiva Life Sciences, Marlborough, MA, USA). The protein is eluted with the linear 100 mM to 1 M NaCl gradient using the buffer B [50 mM Tris-HCl (pH 8.0), 1 M NaCl, 0.5 mM EDTA, 1 mM DTT, 5% (v/v) glycerol]. Column fractions are analyzed by 10% SDS-PAGE. Fractions containing desired protein are pooled and dialyzed against the storage buffer [50 mM Tris-HCl (pH 7.5), 250 mM NaCl, 0.5 mM EDTA, 1 mM DTT, 5% (v/v) glycerol] at 4° C. overnight. The dialyzed protein fraction pool containing the target protein is concentrated using an Amicon filter unit (MW cut-off 50,000). The concentrated protein pool is aliquoted and stored at −20° C. Each mutant polymerase variant was purified with the same procedures as described above. The final protein concentration is determined by the Bradford reaction (Bradford, 1976) using the Bio-Rad Protein Assay (Hercules, CA) with bovine serum albumin as a standard.

Example 3

Template-Dependent DNA Synthesis Assay

The PolB variants provided herein are tested for DNA sequencing-by-synthesis (SBS) approach. To further evaluate the activities (incorporation of nucleotide analogues) of the PolB variants, modified nucleotides and duplex primer/template (P/T)-DNA are used herein.

Figure 3:
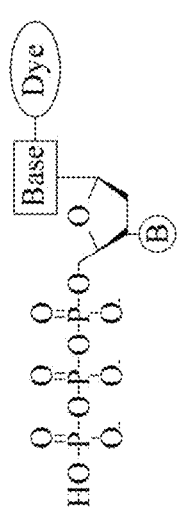
FIG. 3 depicts a general structure of a dye-labelled nucleotide analogue with a removable 3'-blocking moiety.
Figure 4:
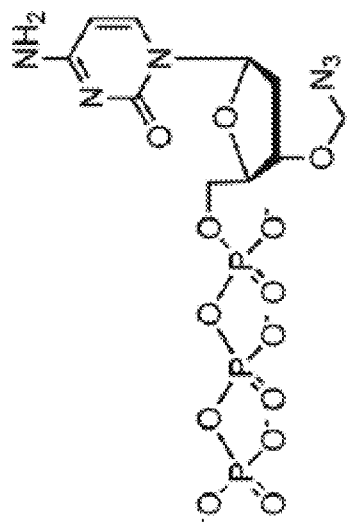
FIG. 4 depicts the structures of 3'-O—$N_3$-dNTP.
Figure 4:
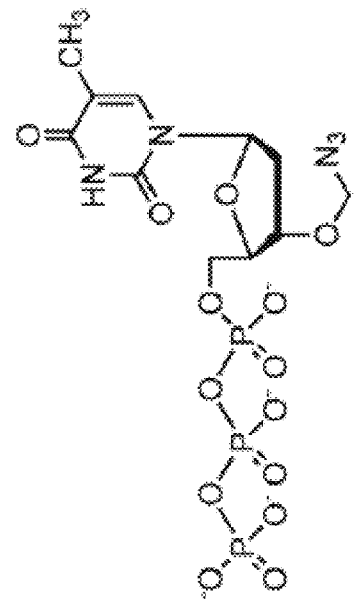
Figure 4:
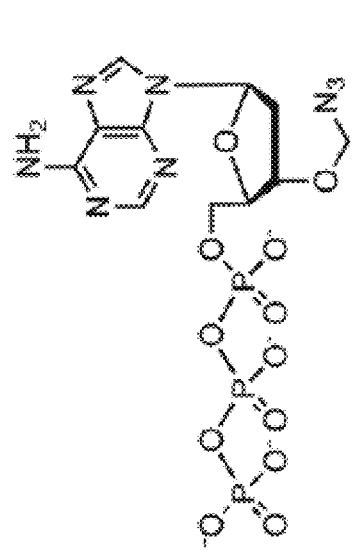
Figure 4:
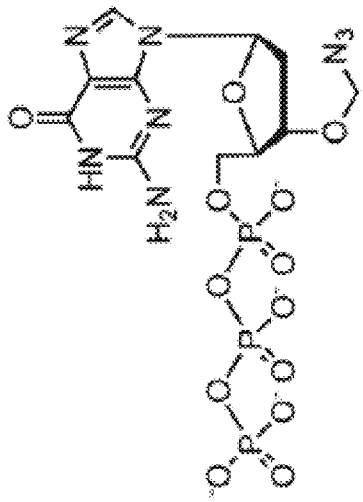
Figure 5A:
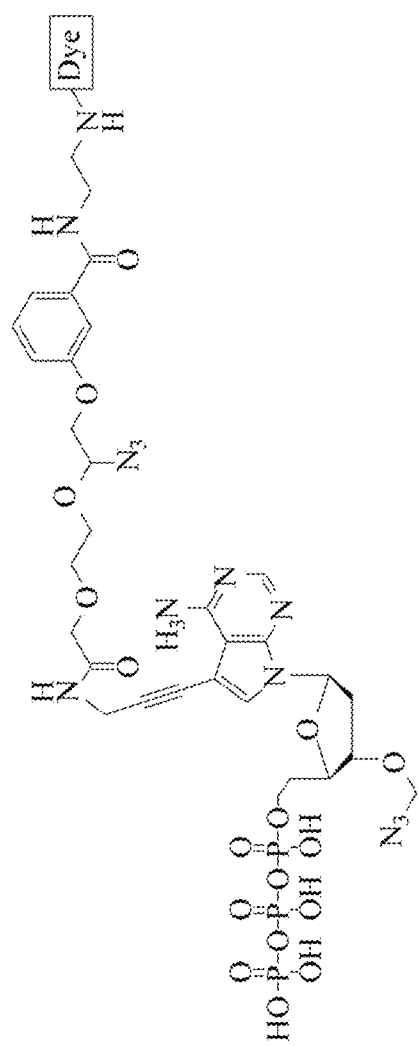
FIG. 5A to 5D, respectively, depict the structures of $N_3$-dATP-linker-Atto532, $N_3$-dCTP-linker-Atto700, $N_3$-dGTP-linker-Cy5 and $N_3$-dTTP-linker-ROX.

In Example 3, the modified nucleotides are nucleotide analogues with a removable blocking moiety (FIG. 3); more specifically, the removable blocking moiety is a 3'-O-azidomethyl group. More specifically, the modified nucleotides are 3'-O-azidomethyl-dNTP including 3'-O-azidomethyl-dATP, 3'-O-azidomethyl-dCTP, 3'-O-azidomethyl-dGTP, 3'-O-azidomethyl-dTTP (as shown in FIG. 4). Furthermore, said modified nucleotides are linked with various forms of dyes, such as $N_3$-dATP-linker-Atto532 (FIG. 5A), $N_3$-dCTP-linker-Atto700 (FIG. 5B), $N_3$-dGTP-linker-Cy5 (FIG. 5C) and $N_3$-dTTP-linker-ROX (FIG. 5D).

In Example 3, the following synthetic oligonucleotides were used as a duplex primer and template (P/T)-DNA to determine the template-dependent DNA synthesis activity of PolB variants:

```
Cy5-38-mer primer:
                                        (SEQ ID NO: 18)
5'-GCTTGCACAAGTTCGTTCAATGATACGGCGACCACCGA-3';
```

The oligonucleotide is labeled with a fluorescent Cyanine5 (Cy5) dye at the 5'-end. The corresponding 45-mer template:

```
                                        (SEQ ID NO: 19)
5'-CGTTCCNTCGGTGGTCGCCGTATCATT

GAACGAACTTGTGCAAGC-3';
wherein the letter "N" represents
either A, T, C, or G.

FAM-38-mer primer:
                                        (SEQ ID NO: 20)
5'-GCTTGCACAAGTTCGTTCAATGATACGGCGACCACCGA-3'

FAM-19-mer primer:
                                        (SEQ ID NO: 21)
5'-GCTTGCACAGGGCCTCGAC-3'
```

Example 4

Activity of Exonuclease-Deficient PolB Variant on Incorporating the 3'-Modified Nucleotides In this example, the activities of exonuclease-deficient PolB variants (Kod1, Pfu, Vent, Mac, Sso) on incorporating 3'-modified nucleotides are compared to that of Pol812; more specifically, said 3'-modified nucleotides are 3'-O-azidomethyl nucleotides. As a polymerase of reference, Pol812, a commercial variant of 9° N polymerase is used.

In procedure, the duplex primer-template (P/T) DNA was formed by annealing the FAM-labeled 19-mer primer with the complementary 29-mer DNA template at a molar ratio of 1:1.5 in the 1×TE buffer [10 mM Tris-HCl (pH 8.0) and 1 mM EDTA] containing 100 mM NaCl. The DNA annealing reaction was performed in the Bio-Rad Thermal Cycler (Hercules, CA) by first heating up the sample mixture to 98° C. for 3 minute and then gradually cooling it down (5° C./30 seconds) to 4° C.

The template-dependent DNA synthesis assay was performed in the reaction mixture (10 μl) containing a 50 nM of duplex P/T-DNA substrate and 200 nM of the polymerase in the ThermoPol buffer [20 mM Tris-HCl (pH 8.8), 10 mM $(NH_4)_2SO_4$, 10 mM KCl, 2 mM $MgSO_4$, and 0.1% Triton X-100]. The DNA synthesis reaction was initiated by adding 10 μM of 3'-O-azidomethyl-dATP. The reaction mixtures were incubated at 55° C. The reactions were terminated after 2 minutes incubation by adding an equal volume (10 μl) of 2× quench solution [95% deionized formamide and 25 mM EDTA]. The sample mixtures were denatured at 95° C. for 10 min and analyzed by 20% polyacrylamide gel electrophoresis containing 8M urea (Urea-PAGE). The DNA synthesis reaction products were then visualized by imaging the gel on the Amersham Typhoon Laser Scanner (Cytiva Life Sciences, Marlborough, MA, USA).

Figure 6:
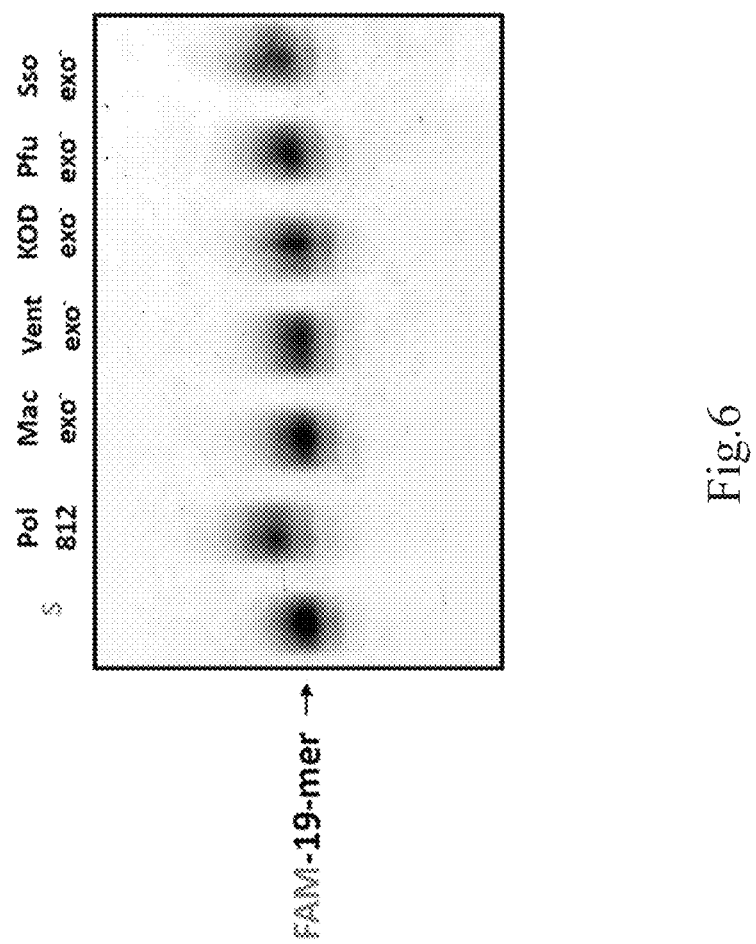
FIG. 6 shows the result of the reaction described in Example 4.

The result of the reaction described above is shown in FIG. 6. In FIG. 6, "S" stands for "duplex P/T-DNA substrate", and the activity of nucleotide incorporation can be inferred from the extent to which the samples shift upward. As such, the result has indicated that none of the nucleotide-incorporation activity of the exemplary PolBs with exonuclease deficiency is comparable to that of Pol812 enzyme. In view of this, it can be concluded that the exonuclease deficiency is not sufficient to endow the PolB enzymes with the activity of incorporating the 3'-O-azidomethyl-dNTP.

Example 5

Activity of Exemplary PolB Variants on Incorporating the 3'-Modified Nucleotides In this example, the exonuclease-deficient PolB (Kod1, Pfu, Vent, Mac, Sso, and 9° N) variants are further substituted with different amino acids in varied regions, and the activity on incorporating 3'-O-azidomethyl-dATP thereof are then evaluated. The procedure applied for evaluating said incorporation is the same with that described above.

The results of the activity performance in correspondence to the PolB variants with varied amino acid forms of substitutions are shown in Table. 1. In Table. 1, "+" stands for "the duplex P/T-DNA substrate is extended with one base"; "+/−" stands for "less than 10% of the duplex P/T-DNA substrate is extended"; and "−" stands for "the duplex P/T-DNA substrate without the nucleotide incorporation". Based on Table. 1, it can be inferred that only when combined with additional amino acid substitutions (either only in Motif A or in both Motifs A and B), the exonuclease-deficient PolB variants can incorporate 3'-O-azidomethyl-dATP. Besides, according to M04 in the Table. 1, the PolB variant cannot incorporate 3'-O-azidomethyl-dATP when it is equally substituted in Motif A region as Pol812; However, said PolB variant exhibits the activity of incorporating the 3'-O-azidomethyl-dNTP with amino acid substitutions of L485Y+Y486A+P487G.

TABLE 1

| Wild-type Enzymes | Variant No. | Modification Substitutions | Activity |
|---|---|---|---|
| Pfu | P01 | Exo⁻ | − |
|  | P02 | Exo⁻ + L409Y + Y410A + P411G | + |
|  | P03 | Exo⁻ + L409Y + Y410A + P411G + A486L | + |
| Kod1 | K01 | Exo⁻ | − |
|  | K02 | Exo⁻ + L408Y + Y409A + P410G | + |
|  | K03 | Exo⁻ + L408Y + Y409A + P410G + A485L | + |
| Vent | V01 | Exo⁻ | − |
|  | V02 | Exo⁻ + L411Y + Y412A + P413G | + |
|  | V03 | Exo⁻ + L411Y + Y412A + P413G + A488L | + |
|  | V04 | Exo⁻ + L411Y + Y412A + P413P + A488L | + |
| Mac | M01 | Exo⁻ | − |
|  | M02 | Exo⁻ + L485Y + Y486A + P487G | + |
|  | M03 | Exo⁻ + L485A + Y486A + P487I + A565L | + |
|  | M04 | Exo⁻ + L485A + Y486A + P487I | − |
| Sso | S01 | Exo⁻ | − |
|  | S02 | Exo⁻ + L518Y + Y519A + P520G | + |
|  | S03 | Exo⁻ + L518Y + Y519A + P520G + A601L | + |
|  | S04 | Exo⁻ + L518A + Y519A + P520I + A601L | + |
| 9° N | N01 | Exo⁻ + M129A + C223S | − |
|  | Pol812 | Exo⁻ + L408A + Y409A + P410I + A485V + M129A + C223S | + |
|  | N02 | Exo⁻ + L408Y + Y409A + P410G + A485V + M129A + C223S | + |
| Pis | I01 | Exo⁻ + M426Y + Y427A + P428G + A508L | + |
|  | I02 | Exo⁻ + M426Y + Y427A + P428P + A508L | + |

Example 6

Efficiency and Fidelity of Exemplary PolB Variants on Incorporating Modified Nucleotides In this section, the efficiency and fidelity of exemplary PolB variants introduced above on incorporating 3'-O-azidomethyl nucleotides are compared to that of Pol812. As representatives of the exemplary PolB variants, variant V03 (Vent with Exo⁻+L411Y+Y412A+P413G+A488L) and M03 (Mac with Exo⁻+L485Y+Y486A+P487G+A565L) are evaluated herein.

In the experimental procedure, the duplex primer-template (P/T) DNA was formed by annealing the FAM-labeled 19-mer primer with the complementary 29-mer DNA template at a molar ratio of 1:1.5 in the 1×TE buffer [10 mM Tris-HCl (pH 8.0) and 1 mM EDTA] containing 100 mM NaCl. The DNA annealing reaction was performed in the Bio-Rad Thermal Cycler (Hercules, CA) by first heating up the sample mixture to 98° C. for 3 minute and then gradually cooling it down (5° C./30 seconds) to 4° C.

The template-dependent DNA synthesis assay was performed in the reaction mixture (10 μl) containing a 50 nM of duplex P/T-DNA substrate and 200 nM of the polymerase in the ThermoPol buffer [20 mM Tris-HCl (pH 8.8), 10 mM (NH$_4$)$_2$SO$_4$, 10 mM KCl, 2 mM MgSO$_4$, and 0.1% Triton X-100]. The DNA synthesis reaction was initiated by adding 10 µM of 3'-O-azidomethyl-dATP. The reaction mixtures were incubated at 55° C. The reactions were terminated after 0.5, 1, 2 and 5 minutes, respectively, incubation by adding an equal volume (10 µl) of 2× quench solution [95% formamide and 25 mM EDTA]. The sample mixtures were denatured at 95° C. for 10 min and analyzed by 20% polyacrylamide gel electrophoresis containing 8M urea (Urea-PAGE). The DNA synthesis reaction products were then visualized by imaging the gel on the Amersham Typhoon Laser Scanner (Cytiva Life Sciences, Marlborough, MA, USA).

Figure 7:
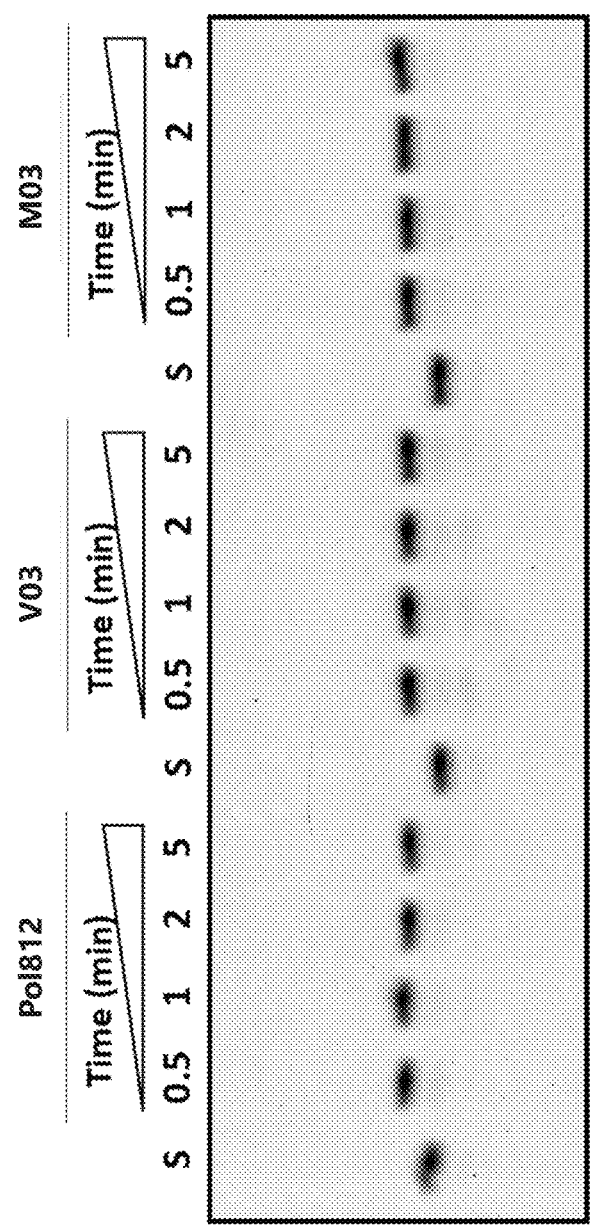
FIG. 7 shows the result of the reaction described in Example 6.

The result of the reaction described above is shown in FIG. 7. In FIG. 7, "S" stands for "duplex P/T-DNA substrate", and the activity of incorporation can be inferred from the extent to which the samples shift upward. As such, the result has indicated that the efficiency and fidelity of both V03 and M03 on incorporating 3'-O-azidomethyl-dATP are comparable to that of Pol812. The other data (not shown) obtained using 3'-O-azidomethyl-dTTP, 3'-O-azidomethyl-dCTP, and 3'-O-azidomethyl-dGTP, respectively, are all consistent with the result above. In view of this, it can be inferred that the combination of specific amino acid substitutions in Motif A and/or Motif B endow PolB variants with improved efficiency and fidelity of incorporating the 3'-O—N$_3$ nucleotides.

Example 7

Activity of Exemplary PolB Variants on Incorporating the Reversible Dye Terminator Nucleotides In this example, the activities of exemplary PolB variants on incorporating the reversible dye-terminator nucleotides (Cy5-N$_3$-dGTP) are compared to that of Pol812. As representatives of the exemplary PolB variants, exonuclease-deficient PolB variants (Kod1 with Exo$^-$, Pfu with Exo$^-$, Vent with Exo$^-$), variant P03 (Pfu with Exo$^-$+L409Y+Y410A+P411G+A486L), variant K03 (Kod1 with Exo$^-$+L408Y+Y409A+P410G+A485L), variant V04 (Vent with Exo$^-$+L411Y+Y412A+P413P+A488L) and variant V03 (Vent with Exo$^-$+L411Y+Y412A+P413G+A488L) are evaluated herein.

In the experimental procedure, the duplex primer-template (P/T) DNA was formed by annealing the FAM-labeled 38-mer primer with the complementary 45-mer DNA template at a molar ratio of 1:1.5 in the 1×TE buffer [10 mM Tris-HCl (pH 8.0) and 1 mM EDTA] containing 100 mM NaCl. The DNA annealing reaction was performed in the Bio-Rad Thermal Cycler (Hercules, CA) by first heating up the sample mixture to 98° C. for 3 minute and then gradually cooling it down (5° C./30 seconds) to 4° C.

The template-dependent DNA synthesis assay was performed in the reaction mixture (10 µl) containing a 50 nM of duplex P/T-DNA substrate and 200 nM of the polymerase in the ThermoPol buffer [20 mM Tris-HCl (pH 8.8), 10 mM (NH$_4$)$_2$SO$_4$, 10 mM KCl, 2 mM MgSO$_4$, and 0.1% Triton X-100]. The DNA synthesis reaction was initiated by adding 10 µM of Cy5-N$_3$-dGTP. The reaction mixtures were incubated at 55° C. The reactions were terminated at 5 minutes incubation by adding an equal volume (10 µl) of 2× quench solution [95% formamide and 25 mM EDTA]. The sample mixtures were denatured at 95° C. for 10 min and analyzed by 20% polyacrylamide gel electrophoresis containing 8M urea (Urea-PAGE). The DNA synthesis reaction products were then visualized by imaging the gel on the Amersham Typhoon Laser Scanner (Cytiva Life Sciences, Marlborough, MA, USA).

Figure 8:
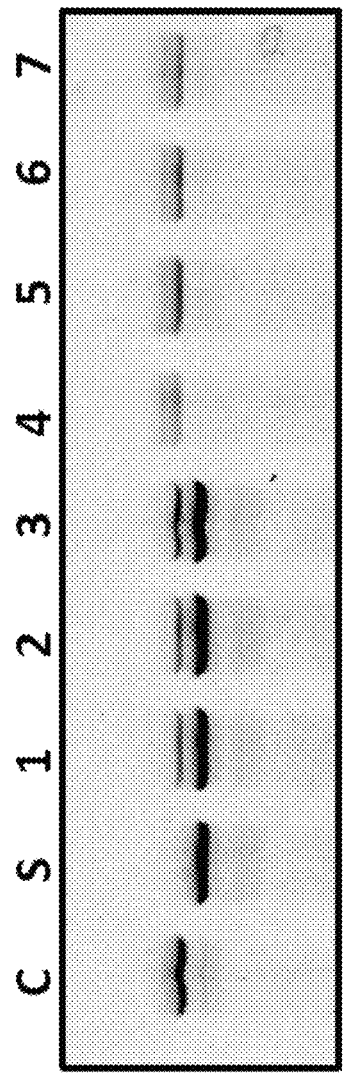
FIG. 8 shows the result of the reaction described in Example 7.

The result of the reaction described above is shown in FIG. 8. In FIG. 8, "C" stands for "Control (Pol812)"; "S" stands for "duplex P/T-DNA substrate", "1" stands for "Pfu with Exo"; "2" stands for "Kod1 with Exo"; "3" stands for "Vent with Exo"; "4" stands for "P03"; "5" stands for "K03"; "6" stands for "V04"; and "7" stands for "V03". The result shown in FIG. 8 has indicated that the activity of the exonuclease-deficient PolB variants (Kod1 with Exo$^-$, Pfu with Exo$^-$, Vent with Exo$^-$) are not comparable with Pol812, while variants with combined substitutions can all exhibit improved performances and are comparable to that of Pol812. In view of this, it can be inferred that the combination of specific amino acid substitutions in Motif A and/or Motif B endow PolB variants with improved activity of incorporating the reversible dye-terminator nucleotides (Cy5-N$_3$-dGTP).

Example 8

Activity of Exemplary PolB Variants on Incorporating Reversible Dye-Terminator Nucleotides In this example, the activities of other exemplary PolB variants on incorporating another reversible dye-terminator nucleotides (Cy5-N$_3$-dGTP) are compared to that of Pol812. As representatives of the exemplary PolB variants, variant I01 (Pis with Exo$^-$+M426Y+Y427A+P428G+A508L) and variant I02 (Pis with Exo$^-$+M426Y+Y427A+P428P+A508L) are evaluated herein.

In the experimental procedure, the duplex primer-template (P/T) DNA was formed by annealing the FAM-labeled 38-mer primer with the complementary 45-mer DNA template at a molar ratio of 1:1.5 in the 1×TE buffer [10 mM Tris-HCl (pH 8.0) and 1 mM EDTA] containing 100 mM NaCl. The DNA annealing reaction was performed in the Bio-Rad Thermal Cycler (Hercules, CA) by first heating up the sample mixture to 98° C. for 3 minute and then gradually cooling it down (5° C./30 seconds) to 4° C.

The template-dependent DNA synthesis assay was performed in the reaction mixture (10 µl) containing a 50 nM of duplex P/T-DNA substrate and 200 nM of the polymerase in the ThermoPol buffer [20 mM Tris-HCl (pH 8.8), 10 mM (NH$_4$)$_2$SO$_4$, 10 mM KCl, 2 mM MgSO$_4$, and 0.1% Triton X-100]. The DNA synthesis reaction was initiated by adding 10 UM of Cy5-N$_3$-dGTP. The reaction mixtures were incubated at 55° C. The reactions were terminated at 5 minutes incubation by adding an equal volume (10 µl) of 2× quench solution [95% formamide and 25 mM EDTA]. The sample mixtures were denatured at 95° C. for 10 min and analyzed by 20% polyacrylamide gel electrophoresis containing 8M urea (Urea-PAGE). The DNA synthesis reaction products were then visualized by imaging the gel on the Amersham Typhoon Laser Scanner (Cytiva Life Sciences, Marlborough, MA, USA).

Figure 9:
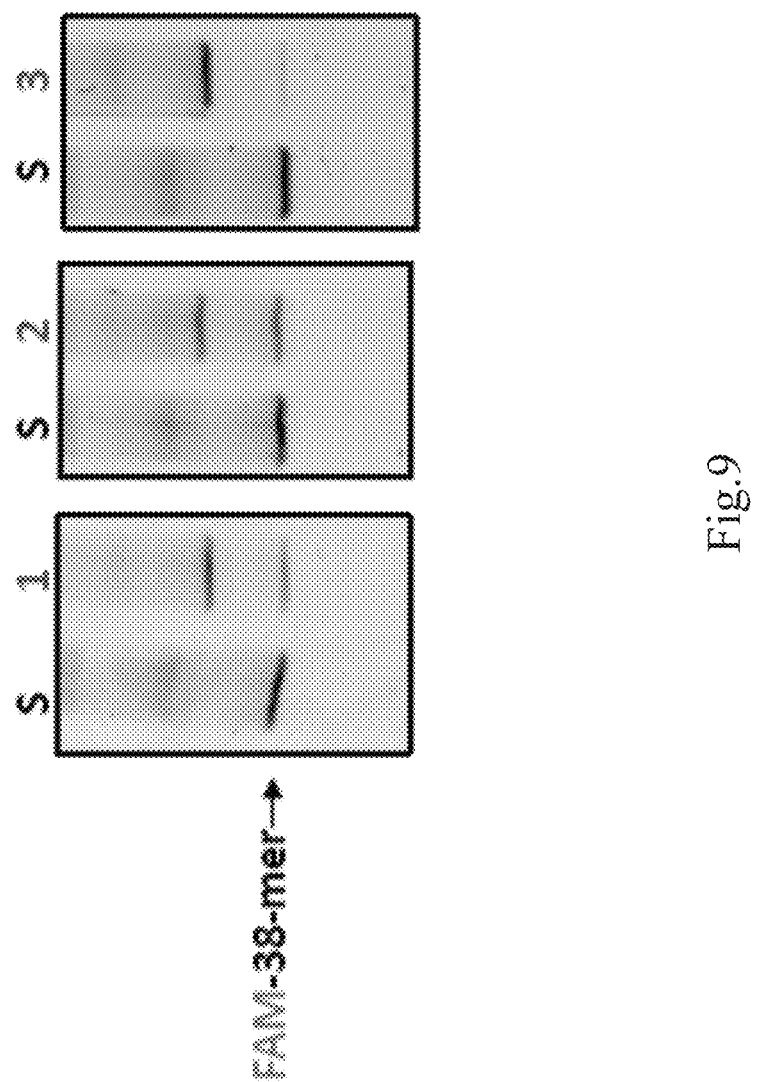
FIG. 9 shows the result of the reaction described in Example 8.

The result of the reaction described above is shown in FIG. 9. In FIG. 9, "S" stands for "duplex P/T-DNA substrate", "1" stands for "Pol812"; "2" stands for "I01"; and "3" stands for "I02". The result shown in FIG. 9 has indicated that variants with combined Motif A and Motif B substitutions can exhibit improved performances that are comparable to that of Pol812, and the activity of I02 is even better than that of Pol812. In view of this, it can be inferred that the combination of specific amino acid substitutions in Motif A and/or Motif B may endow PolB variants with improved activity of incorporating the reversible dye-terminator nucleotides (Cy5-N$_3$-dGTP).

Example 9

Figure 5B:
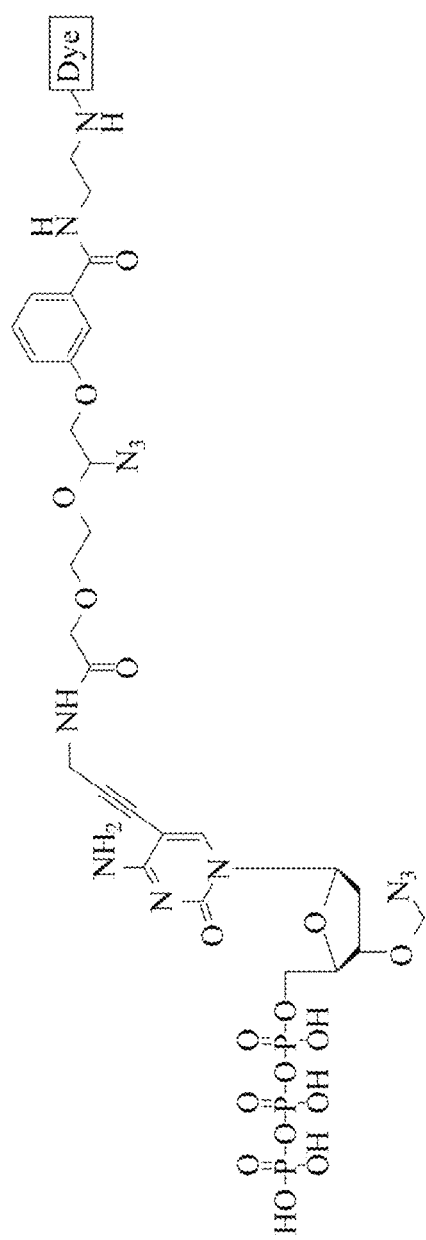
Figure 5C:
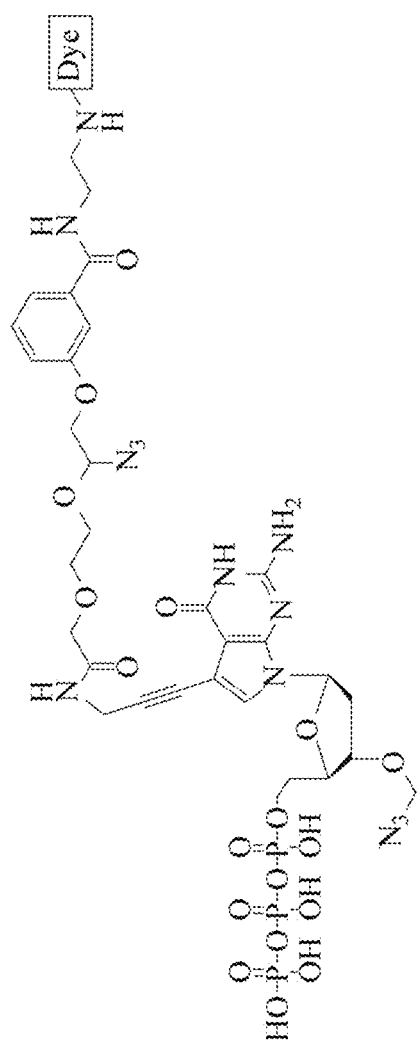
Figure 5D:
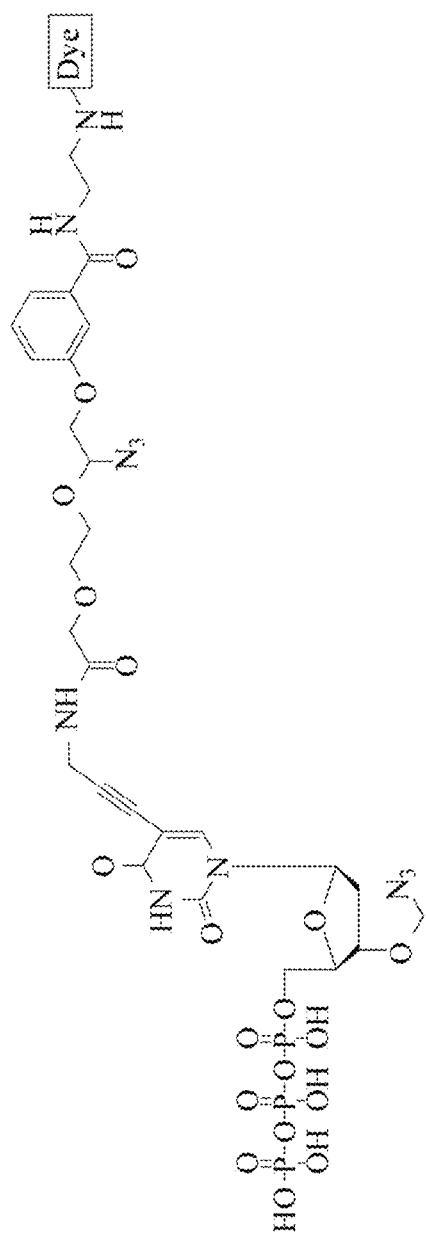

Activity of Exemplary PolB Variants on Incorporating the Reversible Dye-Terminator Nucleotide In this example, the activities of various exemplary PolB variants on incorporating the reversible dye-terminator nucleotides (N$_3$-dNTP-Linker-Dye) are evaluated. The representatives of the exemplary PolB variants examined herein are as follows:

- variant 1: Pol812 (strain 9° N);
- variant 2: 9° N with Exo$^-$+L408Y+Y409A+P410G+A485V;
- variant 3: 9° N with Exo$^-$+L408Y+Y409A+P410G+A485L;
- variant 4: Vent with Exo$^-$+L411Y+Y412A+P413G+A488L;
- variant 5: Vent with Exo$^-$+L411Y+Y412A+P413G+A488L+K480M;
- variant 6: Pfu with Exo$^-$+L409Y+Y410A+P411G+A486L;
- variant 7: Pfu with Exo$^-$+L409Y+Y410A+P411G+A486L+I478M;

The PolB variants described above are examined with the N$_3$-dTTP-Linker-ROX (structure thereof is shown in FIG. 5D), N$_3$-dCTP-Linker-Atto700 (structure thereof is shown in FIG. 5B)

In the experimental procedure, the duplex primer-template (P/T) DNA was formed by annealing the FAM-labeled 38-mer primer/Cy5-labeled 38-mer primer with the complementary 45-mer DNA template at a molar ratio of 1:1.5 in the 1×TE buffer [10 mM Tris-HCl (pH 8.0) and 1 mM EDTA] containing 100 mM NaCl. The DNA annealing reaction was performed in the Bio-Rad Thermal Cycler (Hercules, CA) by first heating up the sample mixture to 98° C. for 3 minute and then gradually cooling it down (5° C./30 seconds) to 4° C.

The template-dependent DNA synthesis assay was performed in the reaction mixture (10 µl) containing a 50 nM of duplex P/T-DNA substrate and 200 nM of the polymerase in the ThermoPol buffer [20 mM Tris-HCl (pH 8.8), 10 mM (NH$_4$)$_2$SO$_4$, 10 mM KCl, 2 mM MgSO$_4$, and 0.1% Triton X-100]. The DNA synthesis reaction was initiated by adding 10 µM of N$_3$-dTTP-Linker-ROX/N$_3$-dCTP-Linker-Atto700. The reaction mixtures were incubated at 55° C. The reactions were terminated at 5 minutes incubation by adding an equal volume (10 µl) of 2× quench solution [95% formamide and 25 mM EDTA]. The sample mixtures were denatured at 95° C. for 10 min and analyzed by 20% polyacrylamide gel electrophoresis containing 8M urea (Urea-PAGE). The DNA synthesis reaction products were then visualized by imaging the gel on the Amersham Typhoon Laser Scanner (Cytiva Life Sciences, Marlborough, MA, USA).

Figure 10:
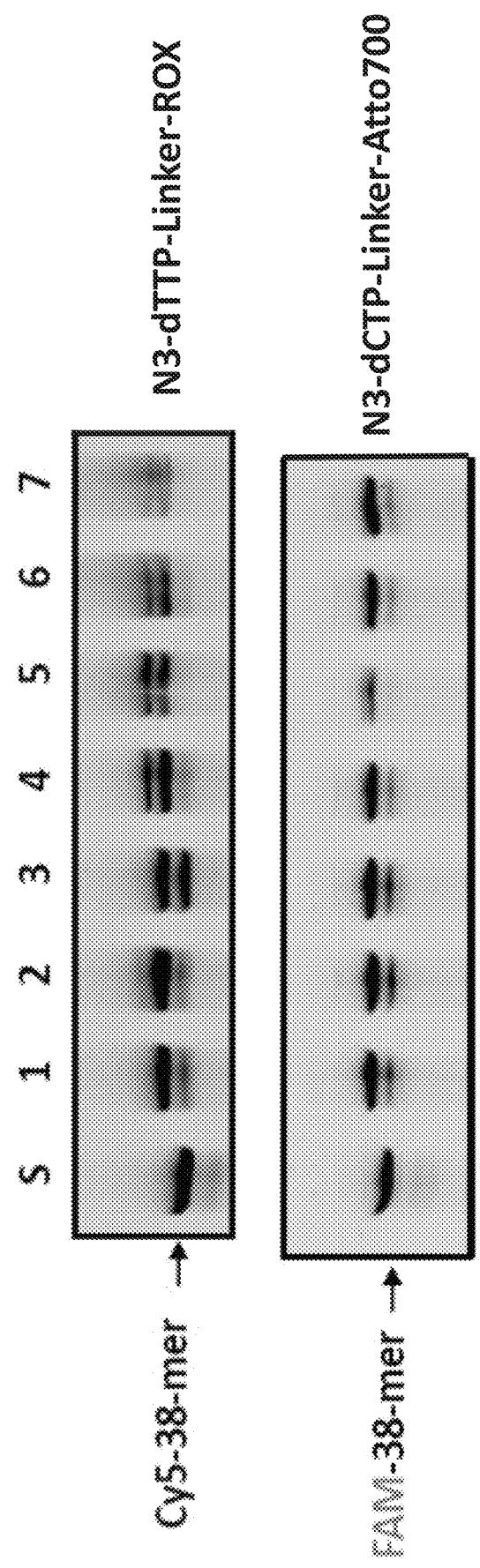
FIG. 10 shows the result of the reaction described in Example 9.

The result of the reaction described above is shown in FIG. 10. In FIG. 10, "S" stands for "duplex P/T-DNA substrate", "1" to "7" stand for "variant1" to "variant7". In view of the result shown in FIG. 10, the PolB variants from strain 9° N with "YAG" substitution in the Motif A combined with the A485 substitutions without M129A and C223S can exhibit comparable performances on incorporating the N$_3$-dNTP-Linker-Dye with that of Pol812, which comprises "AAI" substitution in the Motif A with A485, M129A and C223S substitutions. Besides, the result shown in FIG. 10 has indicated that such combination of specific substitutions in the Motif A and/or Motif B may endow PolB variants from different strains with improved activity of incorporating the N$_3$-dTTP-Linker-ROX or N$_3$-dCTP-Linker-Atto700 as well. Besides, the other data (not shown) obtained through using FAM-labeled 38-mer primer/N$_3$-dGTP-Linker-Cy5 and Cy5-labeled 38-mer primer/N$_3$-dATP-Linker-Atto532 are both consistent with the result above.

In summary, the B-family DNA polymerase variants provided herein can exhibit improved incorporation of nucleotide analogues for synthesizing polynucleotides and sequencing the associated nucleic acid template. The specific embodiments of the present invention have been disclosed, but it is not intended to limit the present invention. Those with ordinary knowledge in the technical field to which the present invention belongs are capable of understanding. And in the case of deviating from the principle and spirit of the present invention, various changes and modifications can be made to it, so the scope of protection of the present invention should be based on those defined in the scope of the accompanying patent application.

What is claimed is:

1. A B-family DNA polymerase variant modified from a wild-type B-family DNA polymerase having an amino acid sequence selected from the group consisting of SEQ ID NOs: 2, 3, 4, 5, 6, 7, 8, 9, 10, 11, 12, 13, 14, 15, 16 and 17, wherein the amino acid L at position 408 of SEQ ID NO: 2, 3, or 4 is substituted with F, I, M, Q, S, H or Y;

the amino acid L at position 409 of SEQ ID NO: 5 is substituted with F, I, M, Q, S, H or Y;
the amino acid L at position 411 of SEQ ID NO: 6 is substituted with F, I, M, Q, S, H or Y;
the amino acid M at position 417 of SEQ ID NO: 7 is substituted with F, I, M, Q, S, H or Y;
the amino acid L at position 485 of SEQ ID NO: 8 is substituted with F, I, M, Q, S, H or Y;
the amino acid L at position 606 of SEQ ID NO: 9 is substituted with F, I, M, Q, S, H or Y;
the amino acid L at position 612 of SEQ ID NO: 10 is substituted with F, I, M, Q, S, H or Y;
the amino acid M at position 426 of SEQ ID NO: 11 is substituted with F, I, M, Q, S, H or Y;
the amino acid L at position 518 of SEQ ID NO: 12 is substituted with F, I, M, Q, S, H or Y;
the amino acid L at position 425 of SEQ ID NO: 13 is substituted with F, I, M, Q, S, H or Y;
the amino acid L at position 423 of SEQ ID NO: 14 is substituted with F, I, M, Q, S, H or Y;
the amino acid F at position 415 of SEQ ID NO: 15 is substituted with F, I, M, Q, S, H or Y;
the amino acid F at position 412 of SEQ ID NO: 16 is substituted with F, I, M, Q, S, H or Y; or
the amino acid F at position 253 of SEQ ID NO: 17 is substituted with F, I, M, Q, S, H or Y.

2. The B-family DNA polymerase variant of claim 1, wherein the B-family DNA polymerase variant is modified from a wild-type B-family DNA polymerase having an amino acid sequence selected from the group consisting of SEQ ID NO: 3, 4, 5, 6, 8, 11, and 12.

3. The B-family DNA polymerase variant of claim 2, wherein the wild-type B-family DNA polymerase is *Thermococcus gorgonarius* DNA polymerase (Tgo), *Thermococcus kodakarensis* DNA polymerase (Kod1), *Thermococcus* sp. (strain 9° N-7) DNA polymerase (9° N), *Pyrococcus furiosus* DNA polymerase (Pfu), *Thermococcus litoralis* DNA polymerase (Vent), *Methanococcus maripaludis* DNA polymerase (Mma), *Methanosarcina acetivorans* DNA polymerase (Mac), human DNA polymerase delta catalytic p125 subunit (hPOLD), *Saccharomyces cerevisiae* DNA polymerase delta catalytic subunit (ScePOLD), *Pyrobaculum islandicum* DNA polymerase, (Pis) *Sulfolobus solfataricus* DNA polymerase (Sso), *Pseudomonas aeruginosa* DNA polymerase II (Pae), *Escherichia coli* DNA polymerase II (Eco), Bacteriophage (*Escherichia* phage) RB69 DNA polymerase (RB69), Bacteriophage (*Escherichia* phage) T4 DNA polymerase (T4), or Bacteriophage (*Bacillus* phage) Phi29 DNA polymerase (Phi29).

4. The B-family DNA polymerase variant of claim 1, wherein the B-family DNA polymerase variant is derived from *Thermococcus kodakarensis* DNA polymerase (Kod1) having a wild-type amino acid sequence of SEQ ID NO:3; and wherein:
   i. D141 of SEQ ID NO: 3 is substituted with A;
   ii. E143 of SEQ ID NO:3 is substituted with A;
   iii. Y409 of SEQ ID NO:3 is substituted with A, C, D, F, G, H or I; and
   iv. P410 of SEQ ID NO:3 is substituted with A, C, F, G, S or T.

5. The B-family DNA polymerase variant of claim 1, wherein the B-family DNA polymerase variant is derived from *Thermococcus* sp. (strain 9° N-7) DNA polymerase (9° N) having a wild-type amino acid sequence of SEQ ID NO:4; and wherein:
   i. D141 of SEQ ID NO:4 is substituted with A;
   ii. E143 of SEQ ID NO:4 is substituted with A;
   iii. Y409 of SEQ ID NO:4 is substituted with A, C, D, F, G, H or I; and iv. P410 of SEQ ID NO:4 is substituted with A, C, F, G, S or T.

6. The B-family DNA polymerase variant of claim 1, wherein the B-family DNA polymerase variant is derived from *Pyrococcus furiosus* DNA polymerase (Pfu) having a wild-type amino acid sequence of SEQ ID NO:5; and wherein:
   i. D141 of SEQ ID NO:5 is substituted with A;
   ii. E143 of SEQ ID NO:5 is substituted with A;
   iii. Y410 of SEQ ID NO:5 is substituted with A, C, D, F, G, H or I; and
   iv. P411 of SEQ ID NO:5 is substituted with A, C, F, G, S or T.

7. The B-family DNA polymerase variant of claim 1, wherein the B-family DNA polymerase variant is derived from *Thermococcus litoralis* DNA polymerase (Vent) having a wild-type amino acid sequence of SEQ ID NO:6; and wherein:
   i. D141 of SEQ ID NO:6 is substituted with A;
   ii. E143 of SEQ ID NO:6 is substituted with A;
   iii. Y412 of SEQ ID NO:6 is substituted with A, C, D, F, G, H or I; and
   iv. P413 of SEQ ID NO:6 is substituted with A, C, F, G, S or T.

8. The B-family DNA polymerase variant of claim 1, wherein the B-family DNA polymerase variant is derived from *Methanosarcina acetivorans* DNA polymerase (Mac) having a wild-type amino acid sequence of SEQ ID NO:8; and wherein:
   i. D198 of SEQ ID NO:8 is substituted with A;
   ii. E200 of SEQ ID NO:8 is substituted with A;
   iii. Y486 of SEQ ID NO:8 is substituted with A, C, D, F, G, H or I; and
   iv. P487 of SEQ ID NO:8 is substituted with A, C, F, G, S or T.

9. The B-family DNA polymerase variant of claim 1, wherein the B-family DNA polymerase variant is derived from *Pyrobaculum islandicum* DNA polymerase (Pis) having a wild-type amino acid sequence of SEQ ID NO:11; and wherein:
   i. D171 of SEQ ID NO:11 is substituted with A;
   ii. E173 of SEQ ID NO:11 is substituted with A;
   iii. Y427 of SEQ ID NO:11 is substituted with A, C, D, F, G, H or I; and
   iv. P428 of SEQ ID NO:11 is substituted with A, C, F, G, S or T.

10. The B-family DNA polymerase variant of claim 1, wherein the B-family DNA polymerase variant is derived from *Sulfolobus solfataricus* DNA polymerase (Sso) having a wild-type amino acid sequence of SEQ ID NO:12; and wherein:
    i D231 of SEQ ID NO:12 is substituted with A;
    ii. E233 of SEQ ID NO:12 is substituted with A;
    iii. Y519 of SEQ ID NO: 12 is substituted with A, C, D, F, G, H or I; and
    iv. P520 of SEQ ID NO:12 is substituted with A, C, F, G, S or T.

11. The B-family DNA polymerase variant of claim 1, wherein the B-family DNA polymerase variant is derived from *Thermococcus kodakarensis* DNA polymerase (Kod1) having a wild-type amino acid sequence of SEQ ID NO:3; and wherein:
    i. D141 of SEQ ID NO:3 is substituted with A;
    ii. E143 of SEQ ID NO:3 is substituted with A;
    iii. Y409 of SEQ ID NO:3 is substituted with A, C, D, F, G, H or I;
    iv. P410 of SEQ ID NO:3 is substituted with A, C, F, G, S or T; and
    v. A485 of SEQ ID NO:3 is substituted with C, D, E, F, or L.

12. The B-family DNA polymerase variant of claim 1, wherein the B-family DNA polymerase variant is derived from *Thermococcus* sp. (strain 9° N-7) DNA polymerase (9° N) having a wild-type amino acid sequence of SEQ ID NO:4; and wherein:
    i. D141 of SEQ ID NO:4 is substituted with A;
    ii. E143 of SEQ ID NO:4 is substituted with A;
    iii. Y409 of SEQ ID NO:4 is substituted with A, C, D, F, G, H or I;
    iv. P410 of SEQ ID NO:4 is substituted with A, C, F, G, S or T; and
    v. A485 of SEQ ID NO:4 is substituted with C, D, E, F, or L.

13. The B-family DNA polymerase variant of claim 1, wherein the B-family DNA polymerase variant is derived from *Pyrococcus furiosus* DNA polymerase (Pfu) having a wild-type amino acid sequence of SEQ ID NO:5; and wherein:
    i. D141 of SEQ ID NO:5 is substituted with A;
    ii. E143 of SEQ ID NO:5 is substituted with A;
    iii. Y410 of SEQ ID NO:5 is substituted with A, C, D, F, G, H or I;
    iv. P411 of SEQ ID NO:5 is substituted with A, C, F, G, S or T; and
    v. A486 of SEQ ID NO:5 is substituted with C, D, E, F, or L.

14. The B-family DNA polymerase variant of claim 1, wherein the B-family DNA polymerase variant is derived from *Thermococcus litoralis* DNA polymerase (Vent) having a wild-type amino acid sequence of SEQ ID NO:6; and wherein:
    i. D141 of SEQ ID NO:6 is substituted with A;
    ii. E143 of SEQ ID NO:6 is substituted with A;
    iii. Y412 of SEQ ID NO:6 is substituted with A, C, D, F, G, H or I;
    iv. P413 of SEQ ID NO:6 is substituted with A, C, F, G, S or T; and
    v. A488 of SEQ ID NO:6 is substituted with C, D, E, F, or L.

15. The B-family DNA polymerase variant of claim 1, wherein the B-family DNA polymerase variant is derived from *Methanosarcina acetivorans* DNA polymerase (Mac) having a wild-type amino acid sequence of SEQ ID NO:8; and wherein:
    i. D198 of SEQ ID NO:8 is substituted with A;
    ii. E200 of SEQ ID NO:8 is substituted with A;
    iii. Y486 of SEQ ID NO:8 is substituted with A, C, D, F, G, H or I;
    iv. P487 of SEQ ID NO:8 is substituted with A, C, F, G, S or T; and
    v. A565 of SEQ ID NO:8 is substituted with C, D, E, F, or L.

16. The B-family DNA polymerase variant of claim 1, wherein the B-family DNA polymerase variant is derived from *Pyrobaculum islandicum* DNA polymerase (Pis) having a wild-type amino acid sequence of SEQ ID NO:11; and wherein:
    i. D171 of SEQ ID NO:11 is substituted with A;
    ii. E173 of SEQ ID NO:11 is substituted with A;
    iii. Y427 of SEQ ID NO:11 is substituted with A, C, D, F, G, H or I;
    iv. P428 of SEQ ID NO:11 is substituted with A, C, E, G, S or T; and v. A508 of SEQ ID NO:11 is substituted with C, D, E, F, or L.

17. The B-family DNA polymerase variant of claim 1, wherein the B-family DNA polymerase variant is derived from *Sulfolobus solfataricus* DNA polymerase (Sso) having a wild-type amino acid sequence of SEQ ID NO:12; and wherein:
  i. D231 of SEQ ID NO:12 is substituted with A;
  ii. E233 of SEQ ID NO:12 is substituted with A;
  iii. Y519 of SEQ ID NO:12 is substituted with A, C, D, F, G, H or I;
  iv. P520 of SEQ ID NO:12 is substituted with A, C, E, G, S or T; and
  v. A601 of SEQ ID NO:12 is substituted with C, D, E, F, or L.

18. A kit for performing a sequencing-by-synthesis reaction, comprising: a B-family DNA polymerase variant as defined in claim 1, a primer, and nucleotide analogues under conditions suitable for incorporation into the primer.

* * * * *

SEQUENCE LISTING

```
<160> NUMBER OF SEQ ID NOS: 21

<210> SEQ ID NO 1
<211> LENGTH: 1360
<212> TYPE: PRT
<213> ORGANISM: Artificial Sequence
<220> FEATURE:
<223> OTHER INFORMATION: consensus sequence
<220> FEATURE:
<221> NAME/KEY: PEPTIDE
<222> LOCATION: (1)..(1360)

<400> SEQUENCE: 1

Met Lys Glu Lys Arg Xaa Xaa Xaa Xaa Xaa Pro Xaa Val Xaa Pro Lys
1               5                   10                  15

Xaa Xaa Xaa Xaa Xaa Xaa Trp Asp Asp Xaa Asp Xaa Pro Xaa Xaa Xaa
            20                  25                  30

Xaa Xaa Ile Lys Arg Gln Ser Ile Asp His Gly Val Gly Xaa Glu Xaa
        35                  40                  45
```

```
Xaa Xaa Xaa Xaa Glu Xaa Xaa Xaa Xaa Xaa Phe Arg Lys Tyr Asn
         50              55              60

Ser Gln Gly Phe Lys Ala Lys Asp Thr Asp Leu Met Gly Thr Xaa Leu
 65              70              75              80

Xaa Xaa Xaa Xaa Glu Xaa Glu Leu Xaa Xaa Xaa Xaa Xaa Xaa Ala
             85              90              95

Asp Gln Gln Xaa Xaa Xaa Ser Ala Xaa Xaa Glu Arg Lys Lys Xaa Pro
            100             105             110

Thr Xaa Xaa Xaa Leu Asp Pro Xaa Xaa Glu Pro Xaa Ile Phe Xaa Ile
        115             120             125

Leu Asp Thr Asp Tyr Xaa Ile Xaa Pro Ala Gln Xaa Val Xaa Xaa Gly
        130             135             140

Xaa Xaa Asp Thr Glu Asp Gly Lys Pro Val Ile Arg Xaa Phe Gly Lys
145             150             155             160

Lys Glu Asn Gly Glu Phe Lys Ile Glu Tyr Asp Arg Thr Phe Glu Pro
            165             170             175

Tyr Phe Tyr Ala Leu Leu Xaa Xaa Gly Xaa Xaa Lys Asp Asp Leu Ser
            180             185             190

Ala Ile Glu Glu Val Lys Lys Ile Thr Ala Glu Arg His Xaa Arg Xaa
            195             200             205

Gly Xaa Glu Thr Xaa Val Arg Val Val Asp Ala Glu Glu Val Val Lys
        210             215             220

Lys Phe Glu Pro Leu Gly Leu Glu Xaa Xaa Arg Pro Ile Glu Val Trp
225             230             235             240

Lys Leu Tyr Phe Xaa His Pro Gln Asp Val Pro Ala Ile Arg Asp Lys
            245             250             255

Ile Arg Glu His Pro Ala Val Val Xaa Xaa Xaa Gly Xaa Xaa Asp Ile
            260             265             270

Xaa Xaa Tyr Glu Tyr Asp Ile Pro Phe Ala Lys Arg Tyr Leu Ile Asp
        275             280             285

Lys Gly Leu Ile Pro Pro Met Ser Trp Val Xaa Met Glu Gly Asp Lys
        290             295             300

Xaa Xaa Xaa Gly Arg Leu Leu Asn Xaa Xaa Ser Xaa Cys Gln Leu Glu
305             310             315             320

Xaa Xaa Xaa Xaa Xaa Ser Asp Xaa Xaa Val His Pro Xaa Xaa Xaa Xaa
            325             330             335

Arg Leu Glu Glu Leu Pro Asp Tyr Ile Pro Pro Leu Lys Val Leu Ala
            340             345             350

Phe Asp Ile Glu Thr Leu Tyr His Xaa Glu Leu Gly Ser Phe Pro Glu
        355             360             365

Pro Gly Lys Gly Xaa Arg Pro Ile Ile Ala Ile Thr His Tyr Asp Ser
        370             375             380

Ile Asp Asp Arg Phe Tyr Val Phe Asp Met Ile Ser Ser Ala Tyr Ala
385             390             395             400

Asp Glu Glu Glu Ala Arg Pro Phe Leu Xaa Xaa Val Ile Thr Trp Lys
            405             410             415

Asn Ile Asp Xaa Leu Pro Tyr Glu Ile Xaa Asp Xaa Val Asp Val Val
            420             425             430

Ser Phe Asp Thr Glu Arg Glu Met Leu Lys Arg Phe Leu Xaa Xaa Xaa
            435             440             445

Xaa Glu Lys Asp Pro Asp Val Ile Ile Gly Tyr Asn Gly Asp Asn Phe
450             455             460
```

```
Asp Xaa Pro Tyr Leu Lys Lys Arg Ala Glu Lys Leu Lys Val Xaa Xaa
465                 470                 475                 480

Xaa Gly Ile Pro Leu Xaa Leu Gly Arg Leu Ser Xaa Lys Arg Ser Ser
            485                 490                 495

Xaa Asp Gly Ser Val Phe Glu Pro Lys Ile Gln Arg Met Tyr Gly Asp
        500                 505                 510

Arg Phe Ala Val Glu Ile Cys Leu Gly Tyr Lys Gly Lys Gly Arg Ile
    515                 520                 525

His Phe Asp Leu Tyr Pro Val Ile Arg Arg Thr Ile Phe Thr Asn Tyr
530                 535                 540

Ala Phe Glu Trp Asn Leu Pro Ser Tyr Thr Leu Glu Ala Val Ala Glu
545                 550                 555                 560

Ala Leu Leu Gly Xaa Xaa Lys Glu Lys Xaa Asp Xaa Xaa Val Tyr Ala
            565                 570                 575

Glu Glu Ile Ala Xaa Ala Trp Asn Glu Xaa Gly Glu Asn Leu Glu Arg
            580                 585                 590

Leu Ala Arg Tyr Ser Xaa Glu Asp Ala Glu Leu Thr Xaa Glu Leu Gly
        595                 600                 605

Ala Lys Lys Glu Phe Leu Pro Xaa Glu Xaa Leu Ile Gln Leu Ser Arg
610                 615                 620

Val Xaa Gly Gln Pro Leu Asp Trp Asp Val Ser Arg Ser Thr Gly
625                 630                 635                 640

Asn Leu Val Glu Trp Leu Leu Leu Arg Lys Ala Tyr Glu Arg Asn Glu
            645                 650                 655

Val Ala Pro Asn Lys Pro Ser Glu Xaa Glu Xaa Ala Arg Arg Xaa Xaa
        660                 665                 670

Xaa Arg Glu Ser Ala Leu Ile Lys Xaa Xaa Xaa Tyr Pro Gly Gly Tyr
    675                 680                 685

Val Trp Leu Asn Asp Arg Phe Lys Glu Pro Xaa Gly Leu Tyr Glu
690                 695                 700

Xaa Asn Ile Val Xaa Leu Asp Phe Arg Ser Leu Tyr Pro Ser Ile Ile
705                 710                 715                 720

Xaa Thr His Asn Leu Ser Pro Asp Thr Leu Leu Asn Arg Glu Gly Cys
            725                 730                 735

Xaa Pro Tyr His Xaa Tyr Ile Xaa Asp Val Ala Pro Glu Glu Xaa Xaa
        740                 745                 750

Val Xaa Xaa Xaa Ser Gly His Xaa Phe Cys Xaa Thr Lys Asp Phe Pro
    755                 760                 765

Gly Phe Ile Pro Ser Ile Leu Ile Lys Arg Gly Asp Leu Leu Glu Glu
770                 775                 780

Arg Lys Lys Ile Lys Lys Ser Gly Gly Lys Met Xaa Ala Xaa Xaa Xaa
785                 790                 795                 800

Asn Xaa Glu Xaa Ile Lys Xaa Xaa Xaa Xaa Xaa Xaa Xaa Leu Ser Xaa
            805                 810                 815

Xaa Glu Xaa Xaa Xaa Val Xaa Xaa Xaa Xaa Xaa Phe Ser Asp Xaa Phe
    820                 825                 830

Lys Lys Thr Ile Asp Pro Asn Thr Xaa Xaa Ile Glu Lys Lys Leu Leu
835                 840                 845

Asp Tyr Arg Gln Arg Ala Ile Xaa Xaa Xaa Thr Xaa Gln Xaa Asn
        850                 855                 860

Arg Lys Ile Leu Ala Asn Ser Phe Tyr Gly Tyr Leu Gly Tyr Ala Lys
865                 870                 875                 880

Ala Arg Trp Tyr Cys Xaa Glu Cys Ala Glu Ser Val Thr Ala Xaa Gly
```

-continued

```
                885                 890                 895
Phe Arg Gln Tyr Ile Glu Xaa Thr Ile Arg Glu Ile Glu Glu Lys Phe
            900                 905                 910
Gly Lys Val Cys Gly Thr Asn Xaa Glu Ala Phe Xaa Xaa Xaa Xaa Ala
            915                 920                 925
Xaa Xaa Cys Xaa Xaa Asn Gly Tyr Xaa Xaa Gly Phe Lys Val Leu Tyr
    930                 935                 940
Gly Asp Thr Asp Ser Xaa Phe Val Thr Ile Pro Gly Xaa Ile Xaa Lys
945                 950                 955                 960
Val Gly Xaa Xaa Xaa Phe Ala Asp Ala Glu Glu Xaa Lys Lys Xaa Ile
            965                 970                 975
Leu Xaa Phe Lys Xaa Xaa Glu Phe Leu Lys Tyr Ile Asn Ala Trp Trp
            980                 985                 990
Arg Glu Xaa Xaa Xaa Tyr Met Asn Lys Leu Pro Gly Leu Leu Glu Leu
            995                 1000                1005
Glu Tyr Glu Gly Phe Tyr Lys Arg Gly Leu Phe Xaa Xaa Gly Arg
        1010                1015                1020
Gly Xaa Phe Val Gly Thr Lys Lys Arg Tyr Ala Gly Leu Ile Asp
        1025                1030                1035
Glu Met Xaa Xaa Asp Arg Phe Ala Glu Gly Lys Ile Thr Thr Lys
        1040                1045                1050
Gly Leu Glu Thr Val Arg Arg Asp Trp Ser Glu Leu Ala Lys Glu
        1055                1060                1065
Thr Gln Ala Arg Val Leu Glu Xaa Ile Leu Lys Xaa Glu Pro Glu
        1070                1075                1080
Gly Asp Val Glu Glu Ala Glu Glu Ser Val Val Xaa Tyr Val Lys
        1085                1090                1095
Glu Val Ile Glu Lys Leu Xaa Xaa Tyr Glu Val Pro Pro Xaa Ala
        1100                1105                1110
Gly Xaa Ile Glu Lys Leu Val Ile His Lys Gln Leu Thr Arg Asp
        1115                1120                1125
Leu Asp Asp Tyr Lys Ala Thr Gly Phe Pro Gly Xaa Lys Cys Pro
        1130                1135                1140
Xaa His Val Ala Val Ala Lys Arg Leu Asp Arg Ala Asn Ala Ala
        1145                1150                1155
Arg Gly Arg Gly Val Lys Xaa Arg Pro Gly Thr Val Ile Ser Tyr
        1160                1165                1170
Val Ile Leu Lys Gly Gly Gly Xaa Ile Gly Asp Xaa Asp Arg Ala
        1175                1180                1185
Ile Pro Pro Asp Glu Xaa Asp Pro Xaa Lys His Lys Tyr Asp Ala
        1190                1195                1200
Glu Tyr Tyr Ile Glu Asn Gln Val Leu Xaa Xaa Pro Ala Val Glu
        1205                1210                1215
Arg Ile Leu Glu Ala Phe Ile Gly Asp Ala Phe Ala Xaa Xaa Xaa
        1220                1225                1230
Xaa Xaa Arg Gly Asp His Xaa Xaa Xaa Xaa Xaa Xaa Thr Gly
        1235                1240                1245
Tyr Arg Lys Glu Asp Leu Xaa Xaa Phe Xaa Lys Xaa Xaa Xaa Xaa
        1250                1255                1260
Cys Xaa Xaa Cys Xaa Xaa Xaa Leu Xaa Xaa Gly Xaa Gly Xaa Xaa
        1265                1270                1275
Cys Xaa Xaa Cys Xaa Xaa Arg Tyr Gln Lys Thr Lys Gln Val Gly
        1280                1285                1290
```

```
Leu Xaa Ala Trp Xaa Xaa Leu Lys Pro Lys Gly Lys Arg Leu Trp
    1295            1300                1305

Thr Gln Cys Gln Arg Cys Xaa Gly Asn Leu His Xaa Xaa Val Xaa
    1310            1315            1320

Cys Xaa Xaa Xaa Cys Xaa Ile Phe Tyr Met Arg Xaa Lys Val
    1325            1330            1335

Xaa Lys Xaa Leu Xaa Asp Xaa Xaa Xaa Xaa Leu Xaa Xaa Phe Gly
    1340            1345            1350

Pro Pro Gly Pro Phe Xaa Phe
    1355            1360

<210> SEQ ID NO 2
<211> LENGTH: 773
<212> TYPE: PRT
<213> ORGANISM: Thermococcus gorgonarius
<220> FEATURE:
<221> NAME/KEY: PEPTIDE
<222> LOCATION: (1)..(773)

<400> SEQUENCE: 2

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Asp Tyr Asp Arg
                20                  25                  30

Asn Phe Glu Pro Tyr Ile Tyr Ala Leu Leu Lys Asp Asp Ser Ala Ile
            35                  40                  45

Glu Asp Val Lys Lys Ile Thr Ala Glu Arg His Gly Thr Thr Val Arg
50                  55                  60

Val Val Arg Ala Glu Lys Val Lys Lys Phe Leu Gly Arg Pro Ile
65                  70                  75                  80

Glu Val Trp Lys Leu Tyr Phe Thr His Pro Gln Asp Val Pro Ala Ile
                85                  90                  95

Arg Asp Lys Ile Lys Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Met Leu Ala Phe Asp Ile Glu Thr
130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Asp Val Val Ser Thr Glu Lys Glu Met Ile Lys
            180                 185                 190

Arg Phe Leu Lys Val Val Lys Glu Lys Asp Pro Asp Val Leu Ile Thr
        195                 200                 205

Tyr Asn Gly Asp Asn Phe Asp Phe Ala Tyr Leu Lys Lys Arg Ser Glu
210                 215                 220

Lys Leu Gly Val Lys Phe Ile Leu Gly Arg Glu Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Ile Phe Gly Gln Pro Lys Glu
```

```
                275                 280                 285
Lys Val Tyr Ala Glu Glu Ile Ala Gln Ala Trp Glu Thr Gly Glu Gly
    290                 295                 300
Leu Glu Arg Val Ala Arg Tyr Ser Met Glu Asp Ala Lys Val Thr Tyr
305                 310                 315                 320
Glu Leu Gly Lys Glu Phe Phe Pro Met Glu Ala Gln Leu Ser Arg Leu
                325                 330                 335
Val Gly Gln Ser Leu Trp Asp Val Ser Arg Ser Thr Gly Asn Leu
                340                 345                 350
Val Glu Trp Phe Leu Leu Arg Lys Ala Tyr Glu Arg Asn Glu Leu Ala
                355                 360                 365
Pro Asn Lys Pro Asp Glu Arg Glu Leu Ala Arg Arg Glu Ser Tyr
    370                 375                 380
Ala Gly Gly Tyr Val Lys Glu Pro Glu Arg Gly Leu Trp Glu Asn Ile
385                 390                 395                 400
Val Tyr Leu Asp Phe Arg Ser Leu Tyr Pro Ser Ile Ile Ile Thr His
                    405                 410                 415
Asn Val Ser Pro Asp Thr Leu Asn Arg Glu Gly Cys Glu Glu Tyr Asp
                420                 425                 430
Val Ala Pro Gln Val Gly His Lys Phe Cys Lys Asp Phe Pro Gly Phe
                435                 440                 445
Ile Pro Ser Leu Leu Gly Asp Leu Leu Glu Glu Arg Gln Lys Val Lys
    450                 455                 460
Lys Lys Met Lys Ala Thr Ile Asp Pro Ile Glu Lys Lys Leu Leu Asp
465                 470                 475                 480
Tyr Arg Gln Arg Ala Ile Lys Ile Leu Ala Asn Ser Phe Tyr Gly Tyr
                    485                 490                 495
Tyr Gly Tyr Ala Lys Ala Arg Trp Tyr Cys Lys Glu Cys Ala Glu Ser
                500                 505                 510
Val Thr Ala Trp Gly Arg Gln Tyr Ile Glu Thr Thr Ile Arg Glu Ile
                515                 520                 525
Glu Glu Lys Phe Gly Phe Lys Val Leu Tyr Ala Asp Thr Asp Gly Phe
                530                 535                 540
Phe Ala Thr Ile Pro Gly Ala Asp Ala Glu Thr Val Lys Lys Lys Ala
545                 550                 555                 560
Lys Glu Phe Leu Asp Tyr Ile Asn Ala Lys Leu Pro Gly Leu Leu Glu
                    565                 570                 575
Leu Glu Tyr Glu Gly Phe Tyr Lys Arg Gly Phe Phe Val Thr Lys Lys
                580                 585                 590
Lys Tyr Ala Val Ile Asp Glu Glu Asp Lys Ile Thr Thr Arg Gly Leu
                595                 600                 605
Glu Ile Val Arg Arg Asp Trp Ser Glu Ile Ala Lys Glu Thr Gln Ala
    610                 615                 620
Arg Val Leu Glu Ala Ile Leu Lys His Gly Asp Val Glu Glu Ala Val
625                 630                 635                 640
Arg Ile Val Lys Glu Val Thr Glu Lys Leu Ser Lys Tyr Glu Val Pro
                    645                 650                 655
Pro Glu Lys Leu Val Ile Tyr Glu Gln Ile Thr Arg Asp Leu Lys Asp
                660                 665                 670
Tyr Lys Ala Thr Gly Pro His Val Ala Val Ala Lys Arg Leu Ala Ala
                675                 680                 685
Arg Gly Ile Lys Ile Arg Pro Gly Thr Val Ile Ser Tyr Ile Val Leu
    690                 695                 700
```

```
Lys Gly Ser Gly Arg Ile Gly Asp Arg Ala Ile Pro Phe Asp Glu Phe
705                 710                 715                 720

Asp Pro Ala Lys His Lys Tyr Asp Ala Glu Tyr Tyr Ile Glu Asn Gln
            725                 730                 735

Val Leu Pro Ala Val Glu Arg Ile Leu Arg Ala Phe Gly Tyr Arg Lys
        740                 745                 750

Glu Asp Leu Arg Tyr Gln Lys Thr Arg Gln Val Gly Leu Gly Ala Trp
    755                 760                 765

Leu Lys Pro Lys Thr
    770
```

<210> SEQ ID NO 3
<211> LENGTH: 774
<212> TYPE: PRT
<213> ORGANISM: Thermococcus kodakarensis
<220> FEATURE:
<221> NAME/KEY: PEPTIDE
<222> LOCATION: (1)..(774)

<400> SEQUENCE: 3

```
Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Glu Tyr Asp Arg
                20                  25                  30

Thr Phe Glu Pro Tyr Phe Tyr Ala Leu Leu Lys Asp Asp Ser Ala Ile
            35                  40                  45

Glu Glu Val Lys Lys Ile Thr Ala Glu Arg His Gly Thr Val Val Thr
    50                  55                  60

Val Lys Arg Val Glu Lys Val Gln Lys Lys Phe Leu Gly Arg Pro Val
65                  70                  75                  80

Glu Val Trp Lys Leu Tyr Phe Thr His Pro Gln Asp Val Pro Ala Ile
                85                  90                  95

Arg Asp Lys Ile Arg Glu His Pro Ala Val Ile Asp Ile Tyr Glu Tyr
            100                 105                 110

Asp Ile Pro Phe Ala Lys Arg Tyr Leu Ile Asp Lys Gly Leu Val Pro
        115                 120                 125

Met Glu Gly Asp Glu Glu Leu Lys Met Leu Ala Phe Asp Ile Glu Thr
130                 135                 140

Leu Tyr Glu Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Val
                165                 170                 175

Asp Leu Pro Tyr Val Asp Val Val Ser Thr Glu Arg Glu Met Ile Lys
            180                 185                 190

Arg Phe Leu Arg Val Val Lys Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Lys Leu Gly Ile Asn Phe Ala Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Gln Pro Lys Glu
```

```
              275                 280                 285
Lys Val Tyr Ala Glu Glu Ile Thr Thr Ala Trp Glu Thr Gly Glu Asn
        290                 295                 300

Leu Glu Arg Val Ala Arg Tyr Ser Met Glu Asp Ala Lys Val Thr Tyr
305                 310                 315                 320

Glu Leu Gly Lys Glu Phe Leu Pro Met Glu Ala Gln Leu Ser Arg Leu
                    325                 330                 335

Ile Gly Gln Ser Leu Trp Asp Val Ser Arg Ser Thr Gly Asn Leu
                340                 345                 350

Val Glu Trp Phe Leu Leu Arg Lys Ala Tyr Glu Arg Asn Glu Leu Ala
            355                 360                 365

Pro Asn Lys Pro Asp Glu Lys Glu Leu Ala Arg Arg Gln Ser Tyr
        370                 375                 380

Glu Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Lys Glu Tyr Asp
                420                 425                 430

Val Ala Pro Gln Val Gly His Arg Phe Cys Lys Asp Phe Pro Gly Phe
            435                 440                 445

Ile Pro Ser Leu Leu Gly Asp Leu Leu Glu Glu Arg Gln Lys Ile Lys
        450                 455                 460

Lys Lys Met Lys Ala Thr Ile Asp Pro Ile Glu Arg Lys Leu Leu Asp
465                 470                 475                 480

Tyr Arg Gln Arg Ala Ile Lys Ile Leu Ala Asn Ser Tyr Tyr Gly Tyr
                485                 490                 495

Tyr Gly Tyr Ala Arg Ala Arg Trp Tyr Cys Lys Glu Cys Ala Glu Ser
                500                 505                 510

Val Thr Ala Trp Gly Arg Glu Tyr Ile Thr Met Thr Ile Lys Glu Ile
            515                 520                 525

Glu Glu Lys Tyr Gly Phe Lys Val Ile Tyr Ser Asp Thr Asp Gly Phe
        530                 535                 540

Phe Ala Thr Ile Pro Gly Ala Asp Ala Glu Thr Val Lys Lys Lys Ala
545                 550                 555                 560

Met Glu Phe Leu Lys Tyr Ile Asn Ala Lys Leu Pro Gly Ala Leu Glu
                565                 570                 575

Leu Glu Tyr Glu Gly Phe Tyr Glu Arg Gly Phe Phe Val Thr Lys Lys
                580                 585                 590

Lys Tyr Ala Val Ile Asp Glu Glu Gly Lys Ile Thr Thr Arg Gly Leu
            595                 600                 605

Glu Ile Val Arg Arg Asp Trp Ser Glu Ile Ala Lys Glu Thr Gln Ala
        610                 615                 620

Arg Val Leu Glu Ala Leu Leu Lys Asp Gly Asp Val Glu Lys Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Lys Asp
                660                 665                 670

Tyr Lys Ala Thr Gly Pro His Val Ala Val Ala Lys Arg Leu Ala Ala
            675                 680                 685

Arg Gly Val Lys Ile Arg Pro Gly Thr Val Ile Ser Tyr Ile Val Leu
        690                 695                 700
```

Lys Gly Ser Gly Arg Ile Gly Asp Arg Ala Ile Pro Phe Asp Glu Phe
705                710                715                720

Asp Pro Thr Lys His Lys Tyr Asp Ala Glu Tyr Tyr Ile Glu Asn Gln
              725                730                735

Val Leu Pro Ala Val Glu Arg Ile Leu Arg Ala Phe Gly Tyr Arg Lys
          740                745                750

Glu Asp Leu Arg Tyr Gln Lys Thr Arg Gln Val Gly Leu Ser Ala Trp
      755                760                765

Leu Lys Pro Lys Gly Thr
  770

<210> SEQ ID NO 4
<211> LENGTH: 775
<212> TYPE: PRT
<213> ORGANISM: Thermococcus sp. 9XN-7
<220> FEATURE:
<221> NAME/KEY: PEPTIDE
<222> LOCATION: (1)..(775)

<400> SEQUENCE: 4

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Asp Val Lys Lys Val Thr Ala Lys Arg His Gly Thr Val Val Lys
    50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Thr Met Leu Ala Phe Asp Ile Glu Thr
130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Val Ser Thr Glu Lys Glu Met Ile Lys
            180                 185                 190

Arg Phe Leu Arg Val Val Arg Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Glu Leu Gly Ile Lys Phe Thr Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu

```
                275                 280                 285
Lys Val Tyr Ala Glu Glu Ile Ala Gln Ala Trp Glu Ser Gly Glu Gly
290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Lys Arg Asn Glu Leu Ala
        355                 360                 365

Pro Asn Lys Pro Asp Glu Arg Glu Leu Ala Arg Arg Gly Gly Tyr
    370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Leu Tyr Pro Ser Ile Ile Thr His
                405                 410                 415

Asn Val Ser Pro Asp Thr Leu Asn Arg Glu Gly Cys Lys Glu Tyr Asp
                420                 425                 430

Val Ala Pro Glu Val Gly His Lys Phe Cys Lys Asp Phe Pro Gly Phe
            435                 440                 445

Ile Pro Ser Leu Leu Gly Asp Leu Leu Glu Glu Arg Gln Lys Ile Lys
        450                 455                 460

Arg Lys Met Lys Ala Thr Val Asp Pro Leu Glu Lys Lys Leu Leu Asp
465                 470                 475                 480

Tyr Arg Gln Arg Ala Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
                500                 505                 510

Val Thr Ala Trp Gly Arg Glu Tyr Ile Glu Met Val Ile Arg Glu Leu
            515                 520                 525

Glu Glu Lys Phe Gly Phe Lys Val Leu Tyr Ala Asp Thr Asp Gly Leu
        530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
                580                 585                 590

Lys Tyr Ala Val Ile Asp Glu Glu Gly Lys Ile Thr Thr Arg Gly Leu
            595                 600                 605

Glu Ile Val Arg Arg Asp Trp Ser Glu Ile Ala Lys Glu Thr Gln Ala
        610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Arg Asp
                660                 665                 670

Tyr Lys Ala Thr Gly Pro His Val Ala Val Ala Lys Arg Leu Ala Ala
            675                 680                 685

Arg Gly Val Lys Ile Arg Pro Gly Thr Val Ile Ser Tyr Ile Val Leu
        690                 695                 700
```

```
Lys Gly Ser Gly Arg Ile Gly Asp Arg Ala Ile Pro Ala Asp Glu Phe
705                 710                 715                 720

Asp Pro Thr Lys His Arg Tyr Asp Ala Glu Tyr Tyr Ile Glu Asn Gln
                725                 730                 735

Val Leu Pro Ala Val Glu Arg Ile Leu Lys Ala Phe Gly Tyr Arg Lys
            740                 745                 750

Glu Asp Leu Arg Tyr Gln Lys Thr Lys Gln Val Gly Leu Gly Ala Trp
        755                 760                 765

Leu Lys Val Lys Gly Lys Lys
        770             775
```

<210> SEQ ID NO 5
<211> LENGTH: 775
<212> TYPE: PRT
<213> ORGANISM: Pyrococcus furiosus
<220> FEATURE:
<221> NAME/KEY: PEPTIDE
<222> LOCATION: (1)..(775)

<400> SEQUENCE: 5

```
Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Val Pro Thr Ile
                85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Glu Leu Lys Ile Leu Ala Phe Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Val Ser Ser Glu Arg Glu Met Ile Lys
            180                 185                 190

Arg Phe Leu Arg Ile Ile Arg Glu Lys Asp Pro Asp Ile Ile Val Thr
        195                 200                 205

Tyr Asn Gly Asp Ser Phe Asp Phe Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
```

```
              275                 280                 285
Lys Val Tyr Ala Asp Glu Ile Ala Lys Ala Trp Glu Ser Gly Glu Asn
290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Phe Leu Leu Arg Lys Ala Tyr Glu Arg Asn Glu Val Ala
        355                 360                 365

Pro Asn Lys Pro Ser Glu Glu Tyr Gln Arg Arg Leu Arg Glu Ser
370                 375                 380

Tyr Thr Gly Gly Phe Val Lys Glu Pro Glu Lys Gly Leu Trp Glu Asn
385                 390                 395                 400

Ile Val Tyr Leu Asp Phe Arg Ala Leu Tyr Pro Ser Ile Ile Ile Thr
                405                 410                 415

His Asn Val Ser Pro Asp Thr Leu Asn Leu Glu Gly Cys Lys Asn Tyr
            420                 425                 430

Asp Ile Ala Pro Gln Val Gly His Lys Phe Cys Lys Asp Ile Pro Gly
        435                 440                 445

Phe Ile Pro Ser Leu Leu Gly His Leu Leu Glu Glu Arg Gln Lys Ile
450                 455                 460

Lys Thr Lys Met Lys Glu Thr Gln Asp Pro Ile Glu Lys Ile Leu Leu
465                 470                 475                 480

Asp Tyr Arg Gln Lys Ala Ile Lys Leu Leu Ala Asn Ser Phe Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Lys Tyr Ile Glu Leu Val Trp Lys Glu
        515                 520                 525

Leu Glu Glu Lys Phe Gly Phe Lys Val Leu Tyr Ile Asp Thr Asp Gly
530                 535                 540

Leu Tyr Ala Thr Ile Pro Gly Gly Glu Ser Glu Glu Ile Lys Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Arg Tyr Ala Val Ile Asp Glu Glu Gly Lys Val Ile Thr Arg Gly
        595                 600                 605

Leu Glu Ile Val Arg Arg Asp Trp Ser Glu Ile Ala Lys Glu Thr Gln
610                 615                 620

Ala Arg Val Leu Glu Thr Ile Leu Lys His Gly Asp Val Glu Glu Ala
625                 630                 635                 640

Val Arg Ile Val Lys Glu Val Ile Gln Lys Leu Ala Asn Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Lys Leu Ala
        675                 680                 685

Ala Lys Gly Val Lys Ile Lys Pro Gly Met Val Ile Gly Tyr Ile Val
690                 695                 700
```

Leu Arg Gly Asp Gly Pro Ile Ser Asn Arg Ala Ile Leu Ala Glu Glu
705                 710                 715                 720

Tyr Asp Pro Lys Lys His Lys Tyr Asp Ala Glu Tyr Tyr Ile Glu Asn
            725                 730                 735

Gln Val Leu Pro Ala Val Leu Arg Ile Leu Glu Gly Phe Gly Tyr Arg
                740                 745                 750

Lys Glu Asp Leu Arg Tyr Gln Lys Thr Arg Gln Val Gly Leu Thr Ser
            755                 760                 765

Trp Leu Asn Ile Lys Lys Ser
770                 775

<210> SEQ ID NO 6
<211> LENGTH: 774
<212> TYPE: PRT
<213> ORGANISM: Thermococcus litoralis
<220> FEATURE:
<221> NAME/KEY: PEPTIDE
<222> LOCATION: (1)..(774)

<400> SEQUENCE: 6

Met Ile Leu Asp Thr Asp Tyr Ile Thr Lys Asp Gly Lys Pro Ile Ile
1               5                   10                  15

Arg Ile Phe Lys Lys Glu Asn Gly Glu Phe Lys Ile Glu Leu Asp Pro
                20                  25                  30

His Phe Gln Pro Tyr Ile Tyr Ala Leu Leu Lys Asp Asp Ser Ala Ile
            35                  40                  45

Glu Glu Ile Lys Ala Ile Lys Gly Glu Arg His Gly Lys Thr Val Arg
50                  55                  60

Val Leu Asp Ala Val Lys Val Arg Lys Lys Phe Leu Gly Arg Glu Val
65                  70                  75                  80

Glu Val Trp Lys Leu Ile Phe Glu His Pro Gln Asp Val Pro Ala Met
                85                  90                  95

Arg Gly Lys Ile Arg Glu His Pro Ala Val Val Asp Ile Tyr Glu Tyr
                100                 105                 110

Asp Ile Pro Phe Ala Lys Arg Tyr Leu Ile Asp Lys Gly Leu Ile Pro
            115                 120                 125

Met Glu Gly Asp Glu Glu Leu Lys Leu Leu Ala Phe Asp Ile Glu Thr
130                 135                 140

Phe Tyr His Glu Gly Asp Glu Phe Gly Lys Gly Glu Ile Ile Met Ile
145                 150                 155                 160

Ser Tyr Ala Asp Glu Glu Glu Ala Arg Val Ile Thr Trp Lys Asn Ile
                165                 170                 175

Asp Leu Pro Tyr Val Asp Val Val Ser Asn Glu Arg Glu Met Ile Lys
            180                 185                 190

Arg Phe Val Gln Val Val Lys Glu Lys Asp Pro Asp Val Ile Ile Thr
            195                 200                 205

Tyr Asn Gly Asp Asn Phe Asp Leu Pro Tyr Leu Ile Lys Arg Ala Glu
210                 215                 220

Lys Leu Gly Val Arg Leu Val Leu Gly Arg Asp Lys Glu His Pro Glu
225                 230                 235                 240

Pro Lys Ile Gln Arg Met Gly Asp Ser Phe Ala Val Glu Ile Lys Gly
                245                 250                 255

Arg Ile His Phe Asp Leu Phe Pro Val Val Arg Arg Thr Ile Asn Leu
                260                 265                 270

Pro Thr Tyr Thr Leu Glu Ala Val Tyr Glu Ala Val Leu Gly Lys Thr

-continued

```
                275                 280                 285
Lys Ser Lys Leu Gly Ala Glu Glu Ile Ala Ala Ile Trp Glu Thr Glu
290                 295                 300
Glu Ser Met Lys Lys Leu Ala Gln Tyr Ser Met Glu Asp Ala Arg Ala
305                 310                 315                 320
Thr Tyr Glu Leu Gly Lys Glu Phe Phe Pro Met Glu Ala Glu Leu Ala
                325                 330                 335
Lys Leu Ile Gly Gln Ser Val Trp Asp Val Ser Arg Ser Ser Thr Gly
                340                 345                 350
Asn Leu Val Glu Trp Tyr Leu Leu Arg Val Ala Tyr Ala Arg Asn Glu
                355                 360                 365
Leu Ala Pro Asn Lys Pro Asp Glu Glu Tyr Lys Arg Arg Leu Arg
370                 375                 380
Thr Thr Tyr Leu Gly Gly Tyr Val Lys Glu Pro Glu Lys Gly Leu Trp
385                 390                 395                 400
Glu Asn Ile Ile Tyr Leu Asp Phe Arg Ser Leu Tyr Pro Ser Ile Ile
                405                 410                 415
Val Thr His Asn Val Ser Pro Asp Thr Leu Glu Lys Glu Gly Cys Lys
                420                 425                 430
Asn Tyr Asp Val Ala Pro Ile Val Gly Tyr Arg Phe Cys Lys Asp Phe
                435                 440                 445
Pro Gly Phe Ile Pro Ser Ile Leu Gly Asp Leu Ile Ala Met Arg Gln
                450                 455                 460
Asp Ile Lys Lys Met Lys Ser Thr Ile Asp Pro Ile Glu Lys Lys
465                 470                 475                 480
Met Leu Asp Tyr Arg Gln Arg Ala Ile Lys Leu Leu Ala Asn Ser Tyr
                485                 490                 495
Tyr Gly Tyr Met Gly Tyr Pro Lys Ala Arg Trp Tyr Ser Lys Glu Cys
                500                 505                 510
Ala Glu Ser Val Thr Ala Trp Gly Arg His Tyr Ile Glu Met Thr Ile
                515                 520                 525
Arg Glu Ile Glu Glu Lys Phe Gly Phe Lys Val Leu Tyr Ala Asp Thr
                530                 535                 540
Asp Gly Phe Tyr Ala Thr Ile Pro Gly Glu Lys Pro Glu Leu Ile Lys
545                 550                 555                 560
Lys Lys Ala Lys Glu Phe Leu Asn Tyr Ile Asn Ser Lys Leu Pro Gly
                565                 570                 575
Leu Leu Glu Leu Glu Tyr Glu Gly Phe Tyr Leu Arg Gly Phe Phe Val
                580                 585                 590
Thr Lys Lys Arg Tyr Ala Val Ile Asp Glu Glu Gly Arg Ile Thr Thr
                595                 600                 605
Arg Gly Leu Glu Val Val Arg Arg Asp Trp Ser Glu Ile Ala Lys Glu
                610                 615                 620
Thr Gln Ala Lys Val Leu Glu Ala Ile Leu Lys Glu Gly Ser Val Glu
625                 630                 635                 640
Lys Ala Val Glu Val Val Arg Asp Val Glu Lys Ile Ala Lys Tyr
                645                 650                 655
Arg Val Pro Leu Glu Lys Leu Val Ile His Glu Gln Ile Thr Arg Asp
                660                 665                 670
Leu Lys Asp Tyr Lys Ala Ile Gly Pro His Val Ala Ile Ala Lys Arg
                675                 680                 685
Leu Ala Ala Arg Gly Ile Lys Val Lys Pro Gly Thr Ile Ile Ser Tyr
                690                 695                 700
```

Ile Val Leu Lys Gly Ser Gly Lys Ile Ser Asp Arg Val Ile Leu Leu
705                 710                 715                 720

Thr Glu Tyr Asp Pro Arg Lys His Lys Tyr Asp Pro Tyr Tyr Ile
            725                 730                 735

Glu Asn Gln Val Leu Pro Ala Val Leu Arg Ile Leu Glu Ala Phe Gly
            740                 745                 750

Tyr Arg Lys Glu Asp Leu Arg Tyr Gln Ser Ser Lys Gln Thr Gly Leu
        755                 760                 765

Asp Ala Trp Leu Lys Arg
        770

<210> SEQ ID NO 7
<211> LENGTH: 784
<212> TYPE: PRT
<213> ORGANISM: Methanococcus maripaludis
<220> FEATURE:
<221> NAME/KEY: PEPTIDE
<222> LOCATION: (1)..(784)

<400> SEQUENCE: 7

Met Glu Ser Leu Ile Asp Leu Asp Tyr Asn Ser Asp Asp Leu Cys Ile
1               5                   10                  15

Tyr Leu Tyr Leu Ile Asn Ser Ile Ile Lys Glu Lys Asp Phe Lys Pro
            20                  25                  30

Tyr Phe Tyr Val Asn Ser Thr Asp Lys Glu Gln Ile Leu Glu Phe Leu
        35                  40                  45

Lys Asp Tyr Glu Lys Lys His Lys Leu Asp Ser Glu Ile Ser Lys Met
50                  55                  60

Ile Glu Asn Ile Glu Thr Val Lys Lys Ile Val Phe Asp Glu Asn Tyr
65                  70                  75                  80

Gln Glu Lys Glu Leu Ser Lys Val Thr Val Lys Tyr Pro Asn Asn Val
            85                  90                  95

Lys Thr Val Arg Glu Ile Leu Met Glu Phe Glu Arg Leu Tyr Glu Tyr
            100                 105                 110

Asp Ile Pro Phe Val Arg Arg Tyr Leu Ile Asp Asn Ser Val Ile Pro
        115                 120                 125

Thr Ser Thr Trp Asp Phe Glu Asn Asn Lys Lys Ile Asp Asn Lys Ile
130                 135                 140

Pro Asp Phe Lys Thr Val Ser Phe Asp Ile Glu Val Tyr Cys Asn Lys
145                 150                 155                 160

Glu Pro Asn Pro Lys Lys Asp Pro Ile Ile Met Ala Ser Phe Ser Ser
            165                 170                 175

Lys Asp Phe Asn Thr Val Val Ser Thr Lys Lys Phe Asp His Glu Lys
            180                 185                 190

Leu Glu Tyr Val Lys Asp Glu Lys Glu Leu Ile Lys Arg Ile Ile Glu
        195                 200                 205

Ile Leu Lys Glu Tyr Asp Ile Ile Tyr Thr Tyr Asn Gly Asp Asn Phe
210                 215                 220

Asp Phe Pro Tyr Leu Lys Lys Arg Ala Glu Ser Phe Gly Leu Glu Leu
225                 230                 235                 240

Lys Leu Gly Lys Asn Asp Glu Lys Ile Lys Ile Thr Lys Gly Gly Met
            245                 250                 255

Asn Ser Lys Ser Tyr Ile Pro Gly Arg Val His Ile Asp Leu Tyr Pro
            260                 265                 270

Ile Ala Arg Arg Leu Leu Asn Leu Thr Lys Tyr Arg Leu Glu Asn Val

|   |   |   | 275 |   |   |   | 280 |   |   |   | 285 |   |
|---|---|---|---|---|---|---|---|---|---|---|---|---|

Thr Glu Ala Leu Phe Asp Val Lys Lys Val Asp Val Gly His Glu Asn
290                 295                 300

Ile Pro Lys Met Trp Asp Asn Leu Asp Glu Thr Leu Val Glu Tyr Ser
305                 310                 315                 320

His Gln Asp Ala Tyr Tyr Thr Gln Arg Ile Gly Glu Gln Phe Leu Pro
                325                 330                 335

Leu Glu Ile Met Phe Ser Arg Val Val Asn Gln Ser Leu Tyr Asp Ile
                340                 345                 350

Asn Arg Met Ser Ser Ser Gln Met Val Glu Tyr Leu Leu Leu Lys Asn
                355                 360                 365

Ser Tyr Lys Met Gly Val Ile Ala Pro Asn Arg Pro Ser Gly Lys Glu
370                 375                 380

Tyr Gln Lys Arg Ile Arg Ser Ser Tyr Glu Gly Gly Tyr Val Lys Glu
385                 390                 395                 400

Pro Leu Lys Gly Ile His Glu Asp Ile Val Ser Met Asp Phe Leu Ser
                405                 410                 415

Leu Tyr Pro Ser Ile Ile Met Ser His Asn Leu Ser Pro Glu Thr Ile
                420                 425                 430

Asp Cys Thr Cys Cys Ser Asp Glu Glu Asn Gly Glu Asn Glu Glu Ile
                435                 440                 445

Leu Gly His Lys Phe Cys Lys Lys Ser Ile Gly Ile Ile Pro Lys Thr
450                 455                 460

Leu Met Asp Leu Ile Asn Arg Arg Lys Val Lys Lys Val Leu Arg
465                 470                 475                 480

Glu Lys Ala Glu Lys Gly Glu Phe Asp Glu Glu Tyr Gln Ile Leu Asp
                485                 490                 495

Tyr Glu Gln Arg Ser Ile Lys Val Leu Ala Asn Ser His Tyr Gly Tyr
                500                 505                 510

Leu Ala Phe Pro Met Ala Arg Trp Tyr Ser Arg Asp Cys Ala Glu Ile
                515                 520                 525

Thr Thr His Leu Gly Arg Gln Tyr Ile Gln Lys Thr Ile Glu Glu Ala
530                 535                 540

Glu Asn Phe Gly Phe Lys Val Ile Tyr Ala Asp Thr Asp Gly Phe Tyr
545                 550                 555                 560

Ser Lys Trp Ala Asp Asp Lys Glu Lys Leu Ser Lys Tyr Glu Leu Leu
                565                 570                 575

Glu Lys Thr Arg Glu Phe Leu Lys Asn Ile Asn Asn Thr Leu Pro Gly
                580                 585                 590

Glu Met Glu Leu Glu Phe Glu Gly Tyr Phe Lys Arg Gly Ile Phe Val
                595                 600                 605

Thr Lys Lys Lys Tyr Ala Leu Ile Asp Glu Asn Glu Lys Ile Thr Val
610                 615                 620

Lys Gly Leu Glu Val Val Arg Arg Asp Trp Ser Asn Val Ser Lys Asn
625                 630                 635                 640

Thr Gln Lys Asn Val Leu Asn Ala Leu Leu Lys Glu Gly Ser Val Glu
                645                 650                 655

Asn Ala Lys Lys Val Ile Gln Asp Thr Ile Lys Glu Leu Lys Asp Gly
                660                 665                 670

Lys Val Asn Asn Glu Asp Leu Leu Ile His Thr Gln Leu Thr Lys Arg
                675                 680                 685

Ile Glu Asp Tyr Lys Thr Thr Ala Pro His Val Glu Val Ala Lys Lys
690                 695                 700

Ile Leu Lys Ser Gly Asn Arg Val Asn Thr Gly Asp Val Ile Ser Tyr
705                 710                 715                 720

Ile Ile Thr Ser Gly Asn Lys Ser Ile Ser Glu Arg Ala Glu Ile Leu
            725                 730                 735

Glu Asn Ala Lys Asn Tyr Asp Thr Asn Tyr Tyr Ile Glu Asn Gln Ile
        740                 745                 750

Leu Pro Pro Val Ile Arg Leu Met Glu Ala Leu Gly Ile Thr Lys Asp
    755                 760                 765

Glu Leu Lys Asp Ser Lys Lys Gln Tyr Thr Leu His His Phe Leu Lys
770                 775                 780

<210> SEQ ID NO 8
<211> LENGTH: 937
<212> TYPE: PRT
<213> ORGANISM: Methanosarcina acetivorans
<220> FEATURE:
<221> NAME/KEY: PEPTIDE
<222> LOCATION: (1)..(937)

<400> SEQUENCE: 8

Met Pro Met Asp Phe Gln Ile Leu Asp Ala Asp Tyr Glu Val Val Asn
1               5                   10                  15

Asp Ser Gly Pro Val Ile Arg Leu Phe Gly Arg Gly Ala Asp Gly Lys
            20                  25                  30

Ser Val Cys Cys Phe Val Pro Asp Phe Glu Pro Tyr Phe Tyr Leu Lys
        35                  40                  45

Ala Ser Gly Asp Leu His Ala Val Ala Arg Leu Ile Lys Asp Thr Phe
    50                  55                  60

Glu Gln Val Lys Lys Val Glu Ile Val Glu Lys Phe Glu Pro Val Gly
65                  70                  75                  80

Tyr Gln Lys Thr Lys Lys Glu Met Leu Arg Val Thr Arg Leu Pro
                85                  90                  95

Lys Asp Val Pro Glu Ile Arg Asp Glu Ile Leu Lys Ile Arg Asp Val
            100                 105                 110

Leu Arg Ala Glu Gly Asp Trp Gln Val Tyr Glu Ser Asp Ile Leu Phe
        115                 120                 125

Arg Asn Arg Phe Leu Ile Asp Arg Ala Leu Gly Gly Met Val Trp Val
    130                 135                 140

Ser Ala Glu Gly Lys Pro Val Asp Pro Val Arg Tyr Leu Gly Ala Gly
145                 150                 155                 160

Ser Ala Trp Arg Ser Arg Cys Glu Asn Phe Ala Cys Asp Ser Ala Val
                165                 170                 175

Leu Ala Ser Gly Leu Lys Arg Val Glu Asn Leu Ala Ile Ala Pro Leu
            180                 185                 190

Lys Tyr Leu Ala Phe Asp Ile Glu Cys Leu Pro Leu Asp Gly Gly Met
        195                 200                 205

Pro Ser Pro Asp Val Ser Pro Ile Ile Met Ile Ser Phe Ser Phe Glu
    210                 215                 220

Pro Glu Tyr Lys Gly His Lys Thr Leu Ile Leu Leu Ala Lys Pro Ala
225                 230                 235                 240

Ala Gly Met Asp Gly Asp Val Leu Ser Cys Met Asp Glu Thr Glu Met
                245                 250                 255

Leu Asn Lys Phe Phe Glu Ile Ile Cys Glu Tyr Asp Pro Asp Ile Val
            260                 265                 270

Ala Gly Tyr Asn His Gln Asp Phe Asp Ile Pro Tyr Ile Thr Glu Arg

```
                   275                 280                 285
        Val Lys Ala Leu Val Ala Lys Gly Glu Thr Ile Asn Ser Val Val Gly
        290                 295                 300

Arg Asp Gly Ser Pro Ile Gly Tyr Arg Lys Phe Gly Leu Ile Thr Arg
        305                 310                 315                 320

Thr Glu Met Lys Gly Arg Val Val Val Asp Ala Leu Pro Leu Val Arg
                        325                 330                 335

Arg Ala Phe Ser Leu Lys Gln Tyr Thr Leu Arg Ala Val Ser Lys Glu
                    340                 345                 350

Leu Leu Ser Arg Glu Lys Leu Asp Val Pro Leu Glu Met Glu Glu
                355                 360                 365

His Trp Asn Asp Ser Gly Asp Lys Phe Arg Lys Phe Val Asp Tyr Ala
        370                 375                 380

Arg Arg Asp Ser Glu Leu Ala Leu Glu Leu Val Leu Glu Leu Arg Leu
        385                 390                 395                 400

Leu Asp Lys Tyr Ile Ala Leu Ala Gln Val Ser Gly Ser Leu Leu Gln
                        405                 410                 415

Glu Ile Val Asp Gly Gly Gln Thr Ser Met Val Glu Thr Leu Leu Leu
                    420                 425                 430

Arg Glu Phe Gly Leu Lys Asp Arg Val Ile Leu Pro Lys Pro Gly Asp
                435                 440                 445

Glu Leu Ser Ala Glu Arg Tyr Asp Met Ser Ser Asp Leu Lys Gly Gly
        450                 455                 460

Glu Val Leu Glu Pro Lys Lys Gly Leu Leu Glu Asn Val Leu Ile Leu
        465                 470                 475                 480

Asp Tyr Lys Ser Leu Tyr Pro Thr Ile Met Met Ala His Asn Leu Cys
                        485                 490                 495

Tyr Thr Thr Val Val Thr Arg Asp Arg Pro Asp Gly Lys Thr Ile Lys
                    500                 505                 510

Pro Pro Ser Gly Gly Glu Phe Val Pro Pro Glu Val Phe Arg Gly Ile
                515                 520                 525

Val Pro Ser Ile Leu Glu Asp Leu Leu Asn Lys Arg Gly Asp Thr Lys
        530                 535                 540

Lys Arg Met Lys Arg Thr Ser Asp Glu Asn Glu His Arg Val Leu Asp
        545                 550                 555                 560

Ala Thr Gln Leu Ala Ile Lys Ile Leu Leu Asn Ser Phe Tyr Gly Tyr
                        565                 570                 575

Ser Gly Tyr Ala Arg Ala Arg Leu Tyr Ser Leu Thr Leu Ala Asn Ala
                    580                 585                 590

Val Thr Ser Phe Gly Arg Ser Asn Ile Leu Asn Thr Arg Asp Leu Ile
                595                 600                 605

Asn Gly Arg Ile Gly Lys Ile Val Leu Arg Asn Ser Ala Ala Leu Leu
        610                 615                 620

Leu Glu Glu Ala Gly Lys Leu Ser Pro Gln Asp Arg Ile Val Glu Leu
        625                 630                 635                 640

Ser Val Ala Tyr Gly Asp Thr Asp Ser Val Phe Val His Cys Lys Ala
                        645                 650                 655

Lys Gly Asp Leu Ser Leu Glu Glu Val Ser Leu Val Gly Asn Arg Leu
                    660                 665                 670

Ser Glu Ile Val Ser Ala Ser Leu Pro Asp Pro Met Glu Leu Glu Phe
                675                 680                 685

Glu Ser Val Ala Lys Arg Ala Leu Leu Ile Ala Lys Lys Arg Tyr Ala
        690                 695                 700
```

```
Leu Trp Leu Phe Glu Pro Arg Asn Ser Gly Trp Glu Asn Lys Ile Lys
705                 710                 715                 720

Val Lys Gly Met Glu Thr Val Arg Arg Asp Trp Cys Glu Leu Thr Ser
                725                 730                 735

Ile Thr Leu Asn Arg Val Leu Glu Phe Val Leu Ile Glu Gly Asp Val
            740                 745                 750

Asp Lys Ala Val Glu His Val Arg Lys Val Val Ser Asp Val Arg Asn
        755                 760                 765

Leu Asp Pro Gly Lys Asp Ala Gly Ile Ile Glu Lys Leu Val Leu Thr
    770                 775                 780

Arg Thr Leu Thr Arg Lys Ala Asp Ser Tyr Lys Asn Lys Gln Pro His
785                 790                 795                 800

Leu Thr Val Ala Glu Asn Leu Lys Lys Arg Thr Gly Ile Met Pro Ser
                805                 810                 815

Ile Gly Thr Arg Ile Pro Phe Val Ile Thr Ala Gly Lys Gly Leu Phe
            820                 825                 830

Val Asp Arg Ala Glu Asp Pro Asp Tyr Val Arg Glu Asn Asn Val Pro
        835                 840                 845

Ile Asp Val Asp Tyr Tyr Val Lys Lys Gln Ile Leu Pro Pro Val Glu
    850                 855                 860

Arg Ile Leu Glu Val Phe Gly Val Lys Met Ser Ser Leu Asp Phe Asp
865                 870                 875                 880

Ala Lys Gln Lys Gly Leu Phe Asp Phe Glu Val Lys Lys Pro Glu Ala
                885                 890                 895

Lys Lys Gln Glu Lys Ser Ser Ser Gln Lys Gly Thr Asn Gly Lys Ile
            900                 905                 910

Leu Glu Lys Ala Pro Glu Glu Lys Ala Arg Tyr Ser Glu Asn Gly Arg
        915                 920                 925

Val Glu Gln Arg Ser Leu Phe Asp Phe
    930                 935

<210> SEQ ID NO 9
<211> LENGTH: 1107
<212> TYPE: PRT
<213> ORGANISM: Homo sapiens
<220> FEATURE:
<221> NAME/KEY: PEPTIDE
<222> LOCATION: (1)..(1107)

<400> SEQUENCE: 9

Met Asp Gly Lys Arg Arg Pro Gly Pro Gly Pro Gly Val Pro Pro Lys
1               5                   10                  15

Arg Ala Arg Gly Gly Leu Trp Asp Asp Asp Ala Pro Arg Pro Ser
                20                  25                  30

Gln Phe Glu Glu Asp Leu Ala Leu Met Glu Glu Met Glu Ala Glu His
            35                  40                  45

Arg Leu Gln Glu Gln Glu Glu Glu Leu Gln Ser Val Leu Glu Gly
        50                  55                  60

Val Ala Asp Gly Gln Val Pro Pro Ser Ala Ile Asp Pro Arg Trp Leu
65                  70                  75                  80

Arg Pro Thr Pro Pro Ala Leu Asp Pro Gln Thr Glu Pro Leu Ile Phe
                85                  90                  95

Gln Gln Leu Glu Ile Asp His Tyr Val Gly Pro Ala Gln Pro Val Pro
            100                 105                 110

Gly Gly Pro Pro Pro Ser Arg Gly Ser Val Pro Val Leu Arg Ala Phe
```

```
            115                 120                 125
Gly Val Thr Asp Glu Gly Phe Ser Val Cys Cys His Ile His Gly Phe
130                 135                 140
Ala Pro Tyr Phe Tyr Thr Pro Ala Pro Pro Gly Phe Gly Pro Glu His
145                 150                 155                 160
Met Gly Asp Leu Gln Arg Glu Leu Asn Leu Ala Ile Ser Arg Asp Ser
                165                 170                 175
Arg Gly Gly Arg Glu Leu Thr Gly Pro Ala Val Leu Ala Val Glu Leu
                180                 185                 190
Cys Ser Arg Glu Ser Met Phe Gly Tyr His Gly His Gly Pro Ser Pro
                195                 200                 205
Phe Leu Arg Ile Thr Val Ala Leu Pro Arg Leu Val Ala Pro Ala Arg
210                 215                 220
Arg Leu Leu Glu Gln Gly Ile Arg Val Ala Gly Leu Gly Thr Pro Ser
225                 230                 235                 240
Phe Ala Pro Tyr Glu Ala Asn Val Asp Phe Glu Ile Arg Phe Met Val
                245                 250                 255
Asp Thr Asp Ile Val Gly Cys Asn Trp Leu Glu Leu Pro Ala Gly Lys
                260                 265                 270
Tyr Ala Leu Arg Leu Lys Glu Lys Ala Thr Gln Cys Gln Leu Glu Ala
                275                 280                 285
Asp Val Leu Trp Ser Asp Val Ser His Pro Pro Glu Gly Pro Trp
290                 295                 300
Gln Arg Ile Ala Pro Leu Arg Val Leu Ser Phe Asp Ile Glu Cys Ala
305                 310                 315                 320
Gly Arg Lys Gly Ile Phe Pro Glu Pro Glu Arg Asp Pro Val Ile Gln
                325                 330                 335
Ile Cys Ser Leu Gly Leu Arg Trp Gly Glu Pro Glu Pro Phe Leu Arg
                340                 345                 350
Leu Ala Leu Thr Leu Arg Pro Cys Ala Pro Ile Leu Gly Ala Lys Val
                355                 360                 365
Gln Ser Tyr Glu Lys Glu Glu Asp Leu Leu Gln Ala Trp Ser Thr Phe
370                 375                 380
Ile Arg Ile Met Asp Pro Asp Val Ile Thr Gly Tyr Asn Ile Gln Asn
385                 390                 395                 400
Phe Asp Leu Pro Tyr Leu Ile Ser Arg Ala Gln Thr Leu Lys Val Gln
                405                 410                 415
Thr Phe Pro Phe Leu Gly Arg Val Ala Gly Leu Cys Ser Asn Ile Arg
                420                 425                 430
Asp Ser Ser Phe Gln Ser Lys Gln Thr Gly Arg Arg Asp Thr Lys Val
                435                 440                 445
Val Ser Met Val Gly Arg Val Gln Met Asp Met Leu Gln Val Leu Leu
                450                 455                 460
Arg Glu Tyr Lys Leu Arg Ser Tyr Thr Leu Asn Ala Val Ser Phe His
465                 470                 475                 480
Phe Leu Gly Glu Gln Lys Glu Asp Val Gln His Ser Ile Ile Thr Asp
                485                 490                 495
Leu Gln Asn Gly Asn Asp Gln Thr Arg Arg Leu Ala Val Tyr Cys
                500                 505                 510
Leu Lys Asp Ala Tyr Leu Pro Leu Arg Leu Leu Glu Arg Leu Met Val
                515                 520                 525
Leu Val Asn Ala Val Glu Met Ala Arg Val Thr Gly Val Pro Leu Ser
530                 535                 540
```

```
Tyr Leu Leu Ser Arg Gly Gln Gln Val Lys Val Ser Gln Leu Leu
545                 550                 555                 560

Arg Gln Ala Met His Glu Gly Leu Leu Met Pro Val Val Lys Ser Glu
                565                 570                 575

Gly Gly Glu Asp Tyr Thr Gly Ala Thr Val Ile Glu Pro Leu Lys Gly
            580                 585                 590

Tyr Tyr Asp Val Pro Ile Ala Thr Leu Asp Phe Ser Ser Leu Tyr Pro
        595                 600                 605

Ser Ile Met Met Ala His Asn Leu Cys Tyr Thr Thr Leu Leu Arg Pro
    610                 615                 620

Gly Thr Ala Gln Lys Leu Gly Leu Thr Glu Asp Gln Phe Ile Arg Thr
625                 630                 635                 640

Pro Thr Gly Asp Glu Phe Val Lys Thr Ser Val Arg Lys Gly Leu Leu
                645                 650                 655

Pro Gln Ile Leu Glu Asn Leu Leu Ser Ala Arg Lys Arg Ala Lys Ala
                660                 665                 670

Glu Leu Ala Lys Glu Thr Asp Pro Leu Arg Arg Gln Val Leu Asp Gly
            675                 680                 685

Arg Gln Leu Ala Leu Lys Val Ser Ala Asn Ser Val Tyr Gly Phe Thr
690                 695                 700

Gly Ala Gln Val Gly Lys Leu Pro Cys Leu Glu Ile Ser Gln Ser Val
705                 710                 715                 720

Thr Gly Phe Gly Arg Gln Met Ile Glu Lys Thr Lys Gln Leu Val Glu
                725                 730                 735

Ser Lys Tyr Thr Val Glu Asn Gly Tyr Ser Thr Ser Ala Lys Val Val
            740                 745                 750

Tyr Gly Asp Thr Asp Ser Val Met Cys Arg Phe Gly Val Ser Ser Val
        755                 760                 765

Ala Glu Ala Met Ala Leu Gly Arg Glu Ala Ala Asp Trp Val Ser Gly
    770                 775                 780

His Phe Pro Ser Pro Ile Arg Leu Glu Phe Glu Lys Val Tyr Phe Pro
785                 790                 795                 800

Tyr Leu Leu Ile Ser Lys Lys Arg Tyr Ala Gly Leu Leu Phe Ser Ser
                805                 810                 815

Arg Pro Asp Ala His Asp Arg Met Asp Cys Lys Gly Leu Glu Ala Val
                820                 825                 830

Arg Arg Asp Asn Cys Pro Leu Val Ala Asn Leu Val Thr Ala Ser Leu
            835                 840                 845

Arg Arg Leu Leu Ile Asp Arg Asp Pro Glu Gly Ala Val Ala His Ala
850                 855                 860

Gln Asp Val Ile Ser Asp Leu Leu Cys Asn Arg Ile Asp Ile Ser Gln
865                 870                 875                 880

Leu Val Ile Thr Lys Glu Leu Thr Arg Ala Ala Ser Asp Tyr Ala Gly
                885                 890                 895

Lys Gln Ala His Val Glu Leu Ala Glu Arg Met Arg Lys Arg Asp Pro
            900                 905                 910

Gly Ser Ala Pro Ser Leu Gly Asp Arg Val Pro Tyr Val Ile Ile Ser
        915                 920                 925

Ala Ala Lys Gly Val Ala Ala Tyr Met Lys Ser Glu Asp Pro Leu Phe
    930                 935                 940

Val Leu Glu His Ser Leu Pro Ile Asp Thr Gln Tyr Tyr Leu Glu Gln
945                 950                 955                 960
```

-continued

```
Gln Leu Ala Lys Pro Leu Leu Arg Ile Phe Glu Pro Ile Leu Gly Glu
            965                 970                 975

Gly Arg Ala Glu Ala Val Leu Leu Arg Gly Asp His Thr Arg Cys Lys
        980                 985                 990

Thr Val Leu Thr Gly Lys Val Gly Gly Leu Leu Ala Phe Ala Lys Arg
    995                 1000                1005

Arg Asn Cys Cys Ile Gly Cys Arg Thr Val Leu Ser His Gln Gly
1010                1015                1020

Ala Val Cys Glu Phe Cys Gln Pro Arg Glu Ser Glu Leu Tyr Gln
    1025                1030                1035

Lys Glu Val Ser His Leu Asn Ala Leu Glu Glu Arg Phe Ser Arg
    1040                1045                1050

Leu Trp Thr Gln Cys Gln Arg Cys Gln Gly Ser Leu His Glu Asp
    1055                1060                1065

Val Ile Cys Thr Ser Arg Asp Cys Pro Ile Phe Tyr Met Arg Lys
    1070                1075                1080

Lys Val Arg Lys Asp Leu Glu Asp Gln Glu Gln Leu Leu Arg Arg
    1085                1090                1095

Phe Gly Pro Pro Gly Pro Glu Ala Trp
    1100                1105

<210> SEQ ID NO 10
<211> LENGTH: 1097
<212> TYPE: PRT
<213> ORGANISM: Saccharomyces cerevisiae
<220> FEATURE:
<221> NAME/KEY: PEPTIDE
<222> LOCATION: (1)..(1097)

<400> SEQUENCE: 10

Met Ser Glu Lys Arg Ser Leu Pro Met Val Asp Val Lys Ile Asp Asp
1               5                   10                  15

Glu Asp Thr Pro Gln Leu Glu Lys Lys Ile Lys Arg Gln Ser Ile Asp
            20                  25                  30

His Gly Val Gly Ser Glu Pro Val Ser Thr Ile Glu Ile Ile Pro Ser
        35                  40                  45

Asp Ser Phe Arg Lys Tyr Asn Ser Gln Gly Phe Lys Ala Lys Asp Thr
    50                  55                  60

Asp Leu Met Gly Thr Gln Leu Glu Ser Thr Phe Glu Gln Glu Leu Ser
65                  70                  75                  80

Gln Met Glu His Asp Met Ala Asp Gln Glu Glu His Asp Leu Ser Ser
                85                  90                  95

Phe Glu Arg Lys Lys Leu Pro Thr Asp Phe Asp Pro Ser Leu Tyr Asp
            100                 105                 110

Ile Ser Phe Gln Gln Ile Asp Ala Glu Gln Ser Val Leu Asn Gly Ile
        115                 120                 125

Lys Asp Glu Asn Thr Ser Thr Val Val Arg Phe Phe Gly Val Thr Ser
    130                 135                 140

Glu Gly His Ser Val Leu Cys Asn Val Thr Gly Phe Lys Asn Tyr Leu
145                 150                 155                 160

Tyr Val Pro Ala Pro Asn Ser Ser Asp Ala Asn Asp Gln Glu Gln Ile
                165                 170                 175

Asn Lys Phe Val His Tyr Leu Asn Glu Thr Phe Asp His Ala Ile Asp
            180                 185                 190

Ser Ile Glu Val Val Ser Lys Gln Ser Ile Trp Gly Tyr Ser Gly Asp
        195                 200                 205
```

```
Thr Lys Leu Pro Phe Trp Lys Ile Tyr Val Thr Tyr Pro His Met Val
    210                 215                 220

Asn Lys Leu Arg Thr Ala Phe Glu Arg Gly His Leu Ser Phe Asn Ser
225                 230                 235                 240

Trp Phe Ser Asn Gly Thr Thr Thr Tyr Asp Asn Ile Ala Tyr Thr Leu
                245                 250                 255

Arg Leu Met Val Asp Cys Gly Ile Val Gly Met Ser Trp Ile Thr Leu
            260                 265                 270

Pro Lys Gly Lys Tyr Ser Met Ile Glu Pro Asn Asn Arg Val Ser Ser
        275                 280                 285

Cys Gln Leu Glu Val Ser Ile Asn Tyr Arg Asn Leu Ile Ala His Pro
    290                 295                 300

Ala Glu Gly Asp Trp Ser His Thr Ala Pro Leu Arg Ile Met Ser Phe
305                 310                 315                 320

Asp Ile Glu Cys Ala Gly Arg Ile Gly Val Phe Pro Glu Pro Glu Tyr
                325                 330                 335

Asp Pro Val Ile Gln Ile Ala Asn Val Val Ser Ile Ala Gly Ala Lys
            340                 345                 350

Lys Pro Phe Ile Arg Asn Val Phe Thr Leu Asn Thr Cys Ser Pro Ile
        355                 360                 365

Thr Gly Ser Met Ile Phe Ser His Ala Thr Glu Glu Met Leu Ser
370                 375                 380

Asn Trp Arg Asn Phe Ile Ile Lys Val Asp Pro Asp Val Ile Ile Gly
385                 390                 395                 400

Tyr Asn Thr Thr Asn Phe Asp Ile Pro Tyr Leu Leu Asn Arg Ala Lys
                405                 410                 415

Ala Leu Lys Val Asn Asp Phe Pro Tyr Phe Gly Arg Leu Lys Thr Val
            420                 425                 430

Lys Gln Glu Ile Lys Glu Ser Val Phe Ser Ser Lys Ala Tyr Gly Thr
        435                 440                 445

Arg Glu Thr Lys Asn Val Asn Ile Asp Gly Arg Leu Gln Leu Asp Leu
    450                 455                 460

Leu Gln Phe Ile Gln Arg Glu Tyr Lys Leu Arg Ser Tyr Thr Leu Asn
465                 470                 475                 480

Ala Val Ser Ala His Phe Leu Gly Glu Gln Lys Glu Asp Val His Tyr
                485                 490                 495

Ser Ile Ile Ser Asp Leu Gln Asn Gly Asp Ser Glu Thr Arg Arg Arg
            500                 505                 510

Leu Ala Val Tyr Cys Leu Lys Asp Ala Tyr Leu Pro Leu Arg Leu Met
        515                 520                 525

Glu Lys Leu Met Ala Leu Val Asn Tyr Thr Glu Met Ala Arg Val Thr
    530                 535                 540

Gly Val Pro Phe Ser Tyr Leu Leu Ala Arg Gly Gln Gln Ile Lys Val
545                 550                 555                 560

Val Ser Gln Leu Phe Arg Lys Cys Leu Glu Ile Asp Thr Val Ile Pro
                565                 570                 575

Asn Met Gln Ser Gln Ala Ser Asp Asp Gln Tyr Glu Gly Ala Thr Val
            580                 585                 590

Ile Glu Pro Ile Arg Gly Tyr Tyr Asp Val Pro Ile Ala Thr Leu Asp
        595                 600                 605

Phe Asn Ser Leu Tyr Pro Ser Ile Met Met Ala His Asn Leu Cys Tyr
610                 615                 620
```

-continued

Thr Thr Leu Cys Asn Lys Ala Thr Val Glu Arg Leu Asn Leu Lys Ile
625                 630                 635                 640

Asp Glu Asp Tyr Val Ile Thr Pro Asn Gly Asp Tyr Phe Val Thr Thr
            645                 650                 655

Lys Arg Arg Arg Gly Ile Leu Pro Ile Ile Leu Asp Glu Leu Ile Ser
        660                 665                 670

Ala Arg Lys Arg Ala Lys Lys Asp Leu Arg Asp Glu Lys Asp Pro Phe
    675                 680                 685

Lys Arg Asp Val Leu Asn Gly Arg Gln Leu Ala Leu Lys Ile Ser Ala
690                 695                 700

Asn Ser Val Tyr Gly Phe Thr Gly Ala Thr Val Gly Lys Leu Pro Cys
705                 710                 715                 720

Leu Ala Ile Ser Ser Val Thr Ala Tyr Gly Arg Thr Met Ile Leu
            725                 730                 735

Lys Thr Lys Thr Ala Val Gln Glu Lys Tyr Cys Ile Lys Asn Gly Tyr
            740                 745                 750

Lys His Asp Ala Val Val Tyr Gly Asp Thr Asp Ser Val Met Val
    755                 760                 765

Lys Phe Gly Thr Thr Asp Leu Lys Glu Ala Met Asp Leu Gly Thr Glu
770                 775                 780

Ala Ala Lys Tyr Val Ser Thr Leu Phe Lys His Pro Ile Asn Leu Glu
785                 790                 795                 800

Phe Glu Lys Ala Tyr Phe Pro Tyr Leu Leu Ile Asn Lys Lys Arg Tyr
            805                 810                 815

Ala Gly Leu Phe Trp Thr Asn Pro Asp Lys Phe Asp Lys Leu Asp Gln
        820                 825                 830

Lys Gly Leu Ala Ser Val Arg Arg Asp Ser Cys Ser Leu Val Ser Ile
        835                 840                 845

Val Met Asn Lys Val Leu Lys Lys Ile Leu Ile Glu Arg Asn Val Asp
    850                 855                 860

Gly Ala Leu Ala Phe Val Arg Glu Thr Ile Asn Asp Ile Leu His Asn
865                 870                 875                 880

Arg Val Asp Ile Ser Lys Leu Ile Ile Ser Lys Thr Leu Ala Pro Asn
            885                 890                 895

Tyr Thr Asn Pro Gln Pro His Ala Val Leu Ala Glu Arg Met Lys Arg
        900                 905                 910

Arg Glu Gly Val Gly Pro Asn Val Gly Asp Arg Val Asp Tyr Val Ile
        915                 920                 925

Ile Gly Gly Asn Asp Lys Leu Tyr Asn Arg Ala Glu Asp Pro Leu Phe
930                 935                 940

Val Leu Glu Asn Asn Ile Gln Val Asp Ser Arg Tyr Tyr Leu Thr Asn
945                 950                 955                 960

Gln Leu Gln Asn Pro Ile Ile Ser Ile Val Ala Pro Ile Ile Gly Asp
            965                 970                 975

Lys Gln Ala Asn Gly Met Phe Val Lys Ser Ile Lys Ile Asn Thr
    980                 985                 990

Gly Ser Gln Lys Gly Gly Leu Met Ser Phe Ile Lys Lys Val Glu Ala
    995                 1000                1005

Cys Lys Ser Cys Lys Gly Pro Leu Arg Lys Gly Glu Gly Pro Leu
    1010                1015                1020

Cys Ser Asn Cys Leu Ala Arg Ser Gly Glu Leu Tyr Ile Lys Ala
    1025                1030                1035

Leu Tyr Asp Val Arg Asp Leu Glu Glu Lys Tyr Ser Arg Leu Trp

-continued

```
            1040                1045                1050
Thr Gln Cys Gln Arg Cys Ala Gly Asn Leu His Ser Glu Val Leu
        1055                1060                1065

Cys Ser Asn Lys Asn Cys Asp Ile Phe Tyr Met Arg Val Lys Val
        1070                1075                1080

Lys Lys Glu Leu Gln Glu Lys Val Glu Gln Leu Ser Lys Trp
        1085                1090                1095
```

<210> SEQ ID NO 11
<211> LENGTH: 785
<212> TYPE: PRT
<213> ORGANISM: Pyrobaculum islandicum
<220> FEATURE:
<221> NAME/KEY: PEPTIDE
<222> LOCATION: (1)..(785)

<400> SEQUENCE: 11

```
Met Glu Leu Lys Val Trp Pro Leu Asp Ile Thr Tyr Ala Val Gly
1               5                   10                  15

Ser Val Pro Glu Ile Arg Ile Phe Gly Ile Leu Ser Ser Gly Glu Arg
                20                  25                  30

Val Val Leu Ile Asp Arg Ser Phe Lys Pro Tyr Phe Tyr Val Asp Cys
            35                  40                  45

Ala Val Cys Glu Pro Ala Ala Leu Lys Thr Ala Leu Ser Arg Val Ala
        50                  55                  60

Pro Ile Asp Asp Val Gln Ile Val Glu Arg Arg Phe Leu Gly Arg Ser
65                  70                  75                  80

Lys Lys Phe Leu Lys Val Ile Ala Lys Ile Pro Glu Asp Val Arg Lys
                85                  90                  95

Leu Arg Glu Ala Ala Met Ser Ile Pro Arg Val Ser Gly Val Tyr Glu
            100                 105                 110

Ala Asp Ile Arg Phe Tyr Met Arg Tyr Met Ile Asp Met Gly Val Val
        115                 120                 125

Pro Cys Ser Trp Asn Val Ala Glu Val Glu Glu Gly Gly Arg Leu Gly
    130                 135                 140

Gly Ile Pro Thr Tyr Val Ser Gln Trp Tyr Gly Ile Asp Glu Gly
145                 150                 155                 160

Phe Pro Pro Ser Leu Lys Val Met Ala Phe Asp Ile Glu Val Tyr Asn
                165                 170                 175

Glu Arg Gly Ser Pro Asp Pro Ile Arg Asp Pro Val Val Met Leu Ala
            180                 185                 190

Ile Lys Thr Asn Asp Gly His Glu Glu Val Phe Glu Ala Ser Gly Lys
        195                 200                 205

Asp Asp Arg Gly Val Val Arg Ala Phe Val Asp Phe Ile Arg Ser Tyr
    210                 215                 220

Asp Pro Asp Val Ile Val Gly Tyr Asn Ser Asn Gly Phe Asp Trp Pro
225                 230                 235                 240

Tyr Leu Val Glu Arg Ala Lys Ala Val Gly Val Pro Leu Lys Val Asp
                245                 250                 255

Arg Leu Ser Asn Pro Pro Gln Gln Ser Val Tyr Gly His Trp Ser Ile
            260                 265                 270

Val Gly Arg Ala Asn Val Asp Leu Tyr Asn Ile Val Glu Glu Phe Pro
        275                 280                 285

Glu Ile Lys Leu Lys Thr Leu Asp Arg Val Ala Glu Tyr Phe Gly Val
    290                 295                 300
```

```
Met Lys Arg Glu Glu Arg Val Leu Ile Pro Gly His Lys Ile Tyr Glu
305                 310                 315                 320

Tyr Trp Lys Asp Pro Asn Lys Arg Pro Leu Leu Lys Arg Tyr Val Leu
            325                 330                 335

Asp Asp Val Arg Ser Thr Leu Gly Leu Ala Asp Lys Leu Leu Pro Phe
            340                 345                 350

Leu Ile Gln Leu Ser Ser Val Ser Gly Leu Pro Leu Asp Gln Val Ala
        355                 360                 365

Ala Ala Ser Val Gly Asn Arg Val Glu Trp Met Leu Leu Arg Tyr Ala
    370                 375                 380

Tyr Arg Leu Gly Glu Val Ala Pro Asn Arg Glu Gln Arg Glu Tyr Glu
385                 390                 395                 400

Pro Tyr Lys Gly Ala Ile Val Leu Glu Pro Lys Pro Gly Met Tyr Glu
            405                 410                 415

Asp Val Leu Val Leu Asp Phe Ser Ser Met Tyr Pro Asn Ile Met Met
            420                 425                 430

Lys Tyr Asn Leu Ser Pro Asp Thr Tyr Leu Glu Pro Gly Glu Pro Asp
        435                 440                 445

Pro Pro Glu Gly Val Asn Val Ala Pro Glu Val Gly His Arg Phe Arg
450                 455                 460

Arg Ser Pro Pro Gly Phe Val Pro Gln Val Leu Lys Ser Leu Val Glu
465                 470                 475                 480

Leu Arg Lys Ala Val Arg Glu Glu Ala Lys Lys Tyr Pro Pro Asp Ser
            485                 490                 495

Pro Glu Phe Lys Ile Leu Asp Glu Arg Gln Arg Ala Leu Lys Val Met
            500                 505                 510

Ala Asn Ala Ile Tyr Gly Tyr Leu Gly Trp Val Gly Ala Arg Trp Tyr
    515                 520                 525

Lys Arg Glu Val Ala Glu Ser Val Thr Ala Phe Ala Arg Ala Ile Leu
530                 535                 540

Lys Asp Val Ile Glu Gln Ala Arg Arg Leu Gly Ile Val Val Val Tyr
545                 550                 555                 560

Gly Asp Thr Asp Ser Leu Phe Val Lys Lys His Gly Asp Val Asp Lys
            565                 570                 575

Leu Ile Lys Tyr Val Glu Glu Lys Tyr Gly Ile Asp Ile Lys Val Asp
            580                 585                 590

Lys Asp Tyr Ala Lys Val Leu Phe Thr Glu Ala Lys Lys Arg Tyr Ala
        595                 600                 605

Gly Leu Leu Arg Asp Gly Arg Ile Asp Ile Val Gly Phe Glu Val Val
    610                 615                 620

Arg Gly Asp Trp Ser Glu Leu Ala Lys Asp Val Gln Leu Arg Val Ile
625                 630                 635                 640

Glu Ile Ile Leu Lys Ser Arg Asp Ile Val Glu Ala Arg His Gly Val
            645                 650                 655

Ile Lys Tyr Ile Arg Glu Ile Ile Glu Arg Leu Lys Asn Tyr Lys Phe
            660                 665                 670

Asn Ile Asp Asp Leu Ile Ile Trp Lys Thr Leu Asp Lys Glu Leu Asp
        675                 680                 685

Glu Tyr Lys Ala Tyr Pro Pro His Val His Ala Ala Gln Ile Leu Lys
    690                 695                 700

Arg His Gly Tyr Arg Val Gly Lys Gly Thr Thr Ile Gly Tyr Val Ile
705                 710                 715                 720

Val Lys Gly Gly Glu Lys Val Ser Glu Arg Ala Leu Pro Tyr Ile Leu
```

```
                        725                 730                 735
Leu Asp Asp Ile Lys Lys Ile Asp Ile Asp Tyr Tyr Ile Glu Arg Gln
                740                 745                 750

Ile Ile Pro Ala Ala Leu Arg Ile Ala Glu Val Ile Gly Val Lys Glu
            755                 760                 765

Ser Asp Leu Lys Thr Gly Arg Met Glu Arg Ser Leu Leu Asp Phe Leu
    770                 775                 780

Ser
785

<210> SEQ ID NO 12
<211> LENGTH: 882
<212> TYPE: PRT
<213> ORGANISM: Sulfolobus solfataricus
<220> FEATURE:
<221> NAME/KEY: PEPTIDE
<222> LOCATION: (1)..(882)

<400> SEQUENCE: 12

Met Thr Lys Gln Leu Thr Leu Phe Asp Ile Pro Ser Ser Lys Pro Ala
1               5                   10                  15

Lys Ser Glu Gln Asn Thr Gln Gln Ser Gln Ser Ala Pro Val Glu
            20                  25                  30

Glu Lys Lys Val Val Arg Arg Glu Trp Leu Glu Glu Ala Gln Glu Asn
        35                  40                  45

Lys Ile Tyr Phe Leu Leu Gln Val Asp Tyr Asp Gly Lys Lys Gly Lys
    50                  55                  60

Ala Val Cys Lys Leu Phe Asp Lys Glu Thr Gln Lys Ile Tyr Ala Leu
65                  70                  75                  80

Tyr Asp Asn Thr Gly His Lys Pro Tyr Phe Leu Val Asp Leu Glu Pro
                85                  90                  95

Asp Lys Val Gly Lys Ile Pro Lys Ile Val Arg Asp Pro Ser Phe Asp
            100                 105                 110

His Ile Glu Thr Val Ser Lys Ile Asp Pro Tyr Thr Trp Asn Lys Phe
        115                 120                 125

Lys Leu Thr Lys Ile Val Val Arg Asp Pro Leu Ala Val Arg Arg Leu
    130                 135                 140

Arg Asn Asp Val Pro Lys Ala Tyr Glu Ala His Ile Lys Tyr Phe Asn
145                 150                 155                 160

Asn Tyr Met Tyr Asp Ile Gly Leu Ile Pro Gly Met Pro Tyr Val Val
                165                 170                 175

Lys Asn Gly Lys Leu Glu Ser Val Tyr Leu Ser Leu Asp Glu Lys Asp
            180                 185                 190

Val Glu Glu Ile Lys Lys Ala Phe Ala Asp Ser Asp Glu Met Thr Arg
        195                 200                 205

Gln Met Ala Val Asp Trp Leu Pro Ile Phe Glu Thr Glu Ile Pro Lys
    210                 215                 220

Ile Lys Arg Val Ala Ile Asp Ile Glu Val Tyr Thr Pro Val Lys Gly
225                 230                 235                 240

Arg Ile Pro Asp Ser Gln Lys Ala Glu Phe Pro Ile Ile Ser Ile Ala
                245                 250                 255

Leu Ala Gly Ser Asp Gly Leu Lys Lys Val Leu Val Leu Asn Arg Asn
            260                 265                 270

Asp Val Asn Glu Gly Ser Val Lys Leu Asp Gly Ile Ser Val Glu Arg
        275                 280                 285
```

Phe Asn Thr Glu Tyr Glu Leu Leu Gly Arg Phe Phe Asp Ile Leu Leu
    290                 295                 300

Glu Tyr Pro Ile Val Leu Thr Phe Asn Gly Asp Asp Phe Asp Leu Pro
305                 310                 315                 320

Tyr Ile Tyr Phe Arg Ala Leu Lys Leu Gly Tyr Phe Pro Glu Glu Ile
                325                 330                 335

Pro Ile Asp Val Ala Gly Lys Asp Glu Ala Lys Tyr Leu Ala Gly Leu
            340                 345                 350

His Ile Asp Leu Tyr Lys Phe Phe Asn Lys Ala Val Arg Asn Tyr
        355                 360                 365

Ala Phe Glu Gly Lys Tyr Asn Glu Tyr Asn Leu Asp Ala Val Ala Lys
370                 375                 380

Ala Leu Leu Gly Thr Ser Lys Val Lys Val Asp Thr Leu Ile Ser Phe
385                 390                 395                 400

Leu Asp Val Glu Lys Leu Ile Glu Tyr Asn Phe Arg Asp Ala Glu Ile
                405                 410                 415

Thr Leu Gln Leu Thr Thr Phe Asn Asn Asp Leu Thr Met Lys Leu Ile
            420                 425                 430

Val Leu Phe Ser Arg Ile Ser Arg Leu Gly Ile Glu Glu Leu Thr Arg
        435                 440                 445

Thr Glu Ile Ser Thr Trp Val Lys Asn Leu Tyr Tyr Trp Glu His Arg
450                 455                 460

Lys Arg Asn Trp Leu Ile Pro Leu Lys Glu Glu Ile Leu Ala Lys Ser
465                 470                 475                 480

Ser Asn Ile Arg Thr Ser Ala Leu Ile Lys Gly Lys Gly Tyr Lys Gly
                485                 490                 495

Ala Val Val Ile Asp Pro Pro Ala Gly Ile Phe Phe Asn Ile Thr Val
            500                 505                 510

Leu Asp Phe Ala Ser Leu Tyr Pro Ser Ile Ile Arg Thr Trp Asn Leu
        515                 520                 525

Ser Tyr Glu Thr Val Asp Ile Gln Gln Cys Lys Lys Pro Tyr Glu Val
530                 535                 540

Lys Asp Glu Thr Gly Glu Val Leu His Ile Val Cys Met Asp Arg Pro
545                 550                 555                 560

Gly Ile Thr Ala Val Ile Thr Gly Leu Leu Arg Asp Phe Arg Val Lys
                565                 570                 575

Ile Tyr Lys Lys Lys Ala Lys Asn Pro Asn Asn Ser Glu Glu Gln Lys
            580                 585                 590

Leu Leu Tyr Asp Val Val Gln Arg Ala Met Lys Val Phe Ile Asn Ala
        595                 600                 605

Thr Tyr Gly Val Phe Gly Ala Glu Thr Phe Pro Leu Tyr Ala Pro Ala
610                 615                 620

Val Ala Glu Ser Val Thr Ala Leu Gly Arg Tyr Val Ile Thr Ser Thr
625                 630                 635                 640

Val Lys Lys Ala Arg Glu Glu Gly Leu Thr Val Leu Tyr Gly Asp Thr
                645                 650                 655

Asp Ser Leu Phe Leu Leu Asn Pro Pro Lys Asn Ser Leu Glu Asn Ile
            660                 665                 670

Ile Lys Trp Val Lys Thr Thr Phe Asn Leu Asp Leu Glu Val Asp Lys
        675                 680                 685

Thr Tyr Lys Phe Val Ala Phe Ser Gly Leu Lys Lys Asn Tyr Phe Gly
690                 695                 700

Val Tyr Gln Asp Gly Lys Val Asp Ile Lys Gly Met Leu Val Lys Lys

-continued

```
              705                 710                 715                 720
Arg Asn Thr Pro Glu Phe Val Lys Lys Val Phe Asn Glu Val Lys Glu
                    725                 730                 735

Leu Met Ile Ser Ile Asn Ser Pro Asn Asp Val Lys Glu Ile Lys Arg
                    740                 745                 750

Lys Ile Val Asp Val Lys Gly Ser Tyr Glu Lys Leu Lys Asn Lys
                    755                 760                 765

Gly Tyr Asn Leu Asp Glu Leu Ala Phe Lys Val Met Leu Ser Lys Pro
                    770                 775                 780

Leu Asp Ala Tyr Lys Lys Asn Thr Pro Gln His Val Lys Ala Ala Leu
785                 790                 795                 800

Gln Leu Arg Pro Phe Gly Val Asn Val Leu Pro Arg Asp Ile Ile Tyr
                    805                 810                 815

Tyr Val Lys Val Arg Ser Lys Asp Gly Val Lys Pro Val Gln Leu Ala
                    820                 825                 830

Lys Val Thr Glu Ile Asp Ala Glu Lys Tyr Leu Glu Ala Leu Arg Ser
                    835                 840                 845

Thr Phe Glu Gln Ile Leu Arg Ala Phe Gly Val Ser Trp Asp Glu Ile
                    850                 855                 860

Ala Ala Thr Met Ser Ile Asp Ser Phe Phe Ser Tyr Pro Ser Lys Gly
865                 870                 875                 880

Asn Ser
```

<210> SEQ ID NO 13
<211> LENGTH: 787
<212> TYPE: PRT
<213> ORGANISM: Pseudomonas aeruginosa
<220> FEATURE:
<221> NAME/KEY: PEPTIDE
<222> LOCATION: (1)..(787)

<400> SEQUENCE: 13

```
Met Glu Leu Leu Gln Gly Phe Val Leu Thr Arg His Trp Arg Asp Thr
1               5                   10                  15

Pro Ala Gly Thr Glu Val Ala Phe Trp Leu Ala Thr Glu Gln Gly Pro
                    20                  25                  30

Arg Gln Val Arg Leu Pro Pro Gln Pro Ser Val Ala Phe Val Leu Ala
                    35                  40                  45

Glu Gln Arg Gly Arg Val Glu Ser Leu Leu Ala Gly Glu Thr Gly Ala
                    50                  55                  60

Glu Leu Arg Pro Leu Ala Leu Arg Asp Phe Gln Gln Arg Pro Val Leu
65                  70                  75                  80

Gly Leu Tyr Cys Gln Gln His Arg Gln Leu Met Asn Leu Glu Lys Arg
                    85                  90                  95

Leu Arg Gln Ala Gly Val Glu Val Phe Glu Ala Asp Ile Arg Pro Pro
                    100                 105                 110

Glu Arg Tyr Leu Met Glu Arg Phe Ile Thr Ala Pro Val Ser Leu Glu
                    115                 120                 125

Ala Ser Val Glu Ala Asp Gly Ser Leu Leu Ala Arg Arg Leu Lys Pro
                    130                 135                 140

Ala Pro Asp Tyr Arg Pro Arg Leu Arg Leu Val Ser Leu Asp Ile Glu
145                 150                 155                 160

Thr Asn Ala Arg Gly Asp Leu Tyr Ser Ile Ala Leu Glu Gly Cys Asp
                    165                 170                 175

Gln Arg Gln Val Tyr Met Leu Gly Pro Ala Asn Gly Asp Ala Ala Ala
```

```
            180                 185                 190
Val Asp Phe Arg Leu Asp Tyr Cys Asp Ser Arg Ala Gly Leu Leu Glu
            195                 200                 205
Arg Leu Asn Gln Trp Leu Ala Glu His Asp Pro Asp Ala Ile Ile Gly
            210                 215                 220
Trp Asn Leu Val Gln Phe Asp Leu Arg Val Leu His Glu His Ala Gln
225                 230                 235                 240
Arg Leu Lys Val Pro Leu Arg Leu Gly Arg Gly Gly Asp Glu Met Gly
            245                 250                 255
Trp Arg Glu His Gly Ser Arg Asn Asn His Phe Phe Ala Ala Ala Ala
            260                 265                 270
Gly Arg Leu Ile Ile Asp Gly Ile Glu Ala Leu Arg Ser Ala Thr Trp
            275                 280                 285
Ser Phe Pro Ser Phe Ser Leu Glu Asn Val Ala Arg Thr Leu Leu Gly
            290                 295                 300
Glu Gly Lys Ala Ile Asp Asn Pro Tyr Gln Arg Met Asp Glu Ile Asp
305                 310                 315                 320
Arg Met Phe Ala Glu Asp Lys Pro Ala Leu Ala His Tyr Asn Leu Lys
            325                 330                 335
Asp Cys Glu Leu Val Thr Arg Ile Phe Ala Arg Thr Glu Leu Leu Asp
            340                 345                 350
Phe Leu Leu Glu Arg Ala Thr Val Thr Gly Leu Pro Ala Asp Arg Ser
            355                 360                 365
Gly Gly Ser Val Ala Ala Phe Thr His Leu Tyr Met Pro Leu Met His
            370                 375                 380
Arg Ala Gly Phe Val Ala Pro Asn Leu Gly Glu Lys Arg Pro Glu Ala
385                 390                 395                 400
Ser Pro Gly Gly Phe Val Met Asp Ser Arg Pro Gly Leu Tyr Glu Ser
            405                 410                 415
Val Leu Val Leu Asp Tyr Lys Ser Leu Tyr Pro Ser Ile Ile Arg Thr
            420                 425                 430
Phe Leu Ile Asp Pro Val Gly Leu Val Glu Gly Leu Arg Gln Pro Asp
            435                 440                 445
Asp Glu His Ser Val Glu Gly Phe Arg Gly Ala Arg Phe Ser Arg Thr
            450                 455                 460
Arg His Cys Leu Pro Ala Ile Val Ala Arg Val Trp Glu Gly Arg Glu
465                 470                 475                 480
Ala Ala Lys Arg Glu Arg Asn Gln Pro Leu Ser Gln Ala Leu Lys Ile
            485                 490                 495
Ile Met Asn Ala Phe Tyr Gly Val Leu Gly Ser Ser Gly Cys Arg Phe
            500                 505                 510
Phe Asp Pro Arg Leu Ala Ser Ser Ile Thr Leu Arg Gly His Arg Ile
            515                 520                 525
Met Arg Arg Thr Arg Glu Leu Ile Glu Ala Glu Gly Tyr Thr Val Ile
            530                 535                 540
Tyr Gly Asp Thr Asp Ser Thr Phe Val Trp Leu Gly Ser Pro Arg Ala
545                 550                 555                 560
Glu Glu Glu Ala Ala Ile Gly Arg Ala Leu Val Ala Arg Val Asn
            565                 570                 575
Asp Trp Trp Arg Glu His Leu Lys Glu Phe Gly Leu Asp Ser Ala
            580                 585                 590
Leu Glu Leu Gln Phe Glu Thr His Tyr Arg Arg Phe Leu Met Pro Thr
            595                 600                 605
```

Val Arg Gly Ala Glu Gly Ser Lys Lys Arg Tyr Ala Gly Leu Val
610                 615                 620

Arg Arg Ala Asp Gly Gly Glu Met Val Phe Lys Gly Leu Glu Thr
625                 630                 635                 640

Val Arg Thr Asp Trp Ser Pro Leu Ala Gln Arg Phe Gln Gln Glu Leu
            645                 650                 655

Tyr Leu Arg Ile Phe Asn Arg Gln Pro Tyr Gln Asp Tyr Val Arg Asp
            660                 665                 670

Tyr Val Arg Arg Thr Leu Ala Gly Glu Leu Asp Asp Leu Leu Val Tyr
            675                 680                 685

Arg Lys Arg Leu Arg Arg Leu Asp Asp Tyr Gln Arg Asn Val Pro
690                 695                 700

Pro His Val Arg Ala Ala Arg Ile Ala Asp Asp Tyr Asn Leu Glu Arg
705                 710                 715                 720

Gly Arg Pro Arg Gln Tyr Gln Ser Gly Gly Trp Ile Ser Tyr Val Ile
            725                 730                 735

Ser Val Ala Gly Pro Glu Pro Leu Glu Ala Arg Ser Ala Ile Asp
            740                 745                 750

Tyr Glu His Tyr Val Gly Lys Gln Leu Gln Pro Val Asp Ala Ile
            755                 760                 765

Leu Pro Phe Val Gly Asp Asp Phe Ala Thr Leu Val Asp Arg Gln Met
770                 775                 780

Ala Leu Phe
785

<210> SEQ ID NO 14
<211> LENGTH: 783
<212> TYPE: PRT
<213> ORGANISM: Escherichia coli
<220> FEATURE:
<221> NAME/KEY: PEPTIDE
<222> LOCATION: (1)..(783)

<400> SEQUENCE: 14

Met Ala Gln Ala Gly Phe Ile Leu Thr Arg His Trp Arg Asp Thr Pro
1               5                   10                  15

Gln Gly Thr Glu Val Ser Phe Trp Leu Ala Thr Asp Asn Gly Pro Leu
            20                  25                  30

Gln Val Thr Leu Ala Pro Gln Glu Ser Val Ala Phe Ile Pro Ala Asp
        35                  40                  45

Gln Val Pro Arg Ala Gln His Ile Leu Gln Gly Glu Gln Gly Phe Arg
    50                  55                  60

Leu Thr Pro Leu Ala Leu Lys Asp Phe His Arg Gln Pro Val Tyr Gly
65                  70                  75                  80

Leu Tyr Cys Arg Ala His Arg Gln Leu Met Asn Tyr Glu Lys Arg Leu
            85                  90                  95

Arg Glu Gly Gly Val Thr Val Tyr Glu Ala Asp Val Arg Pro Pro Glu
        100                 105                 110

Arg Tyr Leu Met Glu Arg Phe Ile Thr Ser Pro Val Trp Val Glu Gly
    115                 120                 125

Asp Met His Asn Gly Thr Ile Val Asn Ala Arg Leu Lys Pro His Pro
130                 135                 140

Asp Tyr Arg Pro Pro Leu Lys Trp Val Ser Ile Asp Ile Glu Thr Thr
145                 150                 155                 160

Arg His Gly Glu Leu Tyr Cys Ile Gly Leu Glu Gly Cys Gly Gln Arg

-continued

```
                165                 170                 175
Ile Val Tyr Met Leu Gly Pro Glu Asn Gly Asp Ala Ser Ser Leu Asp
                180                 185                 190

Phe Glu Leu Glu Tyr Val Ala Ser Arg Pro Gln Leu Leu Glu Lys Leu
                195                 200                 205

Asn Ala Trp Phe Ala Asn Tyr Asp Pro Asp Val Ile Ile Gly Trp Asn
                210                 215                 220

Val Val Gln Phe Asp Leu Arg Met Leu Gln Lys His Ala Glu Arg Tyr
225                 230                 235                 240

Arg Leu Pro Leu Arg Leu Gly Arg Asp Asn Ser Glu Leu Glu Trp Arg
                245                 250                 255

Glu His Gly Phe Lys Asn Gly Val Phe Phe Ala Gln Ala Lys Gly Arg
                260                 265                 270

Leu Ile Ile Asp Gly Ile Glu Ala Leu Lys Ser Ala Phe Trp Asn Phe
                275                 280                 285

Ser Ser Phe Ser Leu Glu Thr Val Ala Gln Glu Leu Leu Gly Glu Gly
                290                 295                 300

Lys Ser Ile Asp Asn Pro Trp Asp Arg Met Asp Glu Ile Asp Arg Arg
305                 310                 315                 320

Phe Ala Glu Asp Lys Pro Ala Leu Ala Thr Tyr Asn Leu Lys Asp Cys
                325                 330                 335

Glu Leu Val Thr Gln Ile Phe His Lys Thr Glu Ile Met Pro Phe Leu
                340                 345                 350

Leu Glu Arg Ala Thr Val Asn Gly Leu Pro Val Asp Arg His Gly Gly
                355                 360                 365

Ser Val Ala Ala Phe Gly His Leu Tyr Phe Pro Arg Met His Arg Ala
                370                 375                 380

Gly Tyr Val Ala Pro Asn Leu Gly Glu Val Pro Pro His Ala Ser Pro
385                 390                 395                 400

Gly Gly Tyr Val Met Asp Ser Arg Pro Gly Leu Tyr Asp Ser Val Leu
                405                 410                 415

Val Leu Asp Tyr Lys Ser Leu Tyr Pro Ser Ile Ile Arg Thr Phe Leu
                420                 425                 430

Ile Asp Pro Val Gly Leu Val Glu Gly Met Ala Gln Pro Asp Pro Glu
                435                 440                 445

His Ser Thr Glu Gly Phe Leu Asp Ala Trp Phe Ser Arg Glu Lys His
                450                 455                 460

Cys Leu Pro Glu Ile Val Thr Asn Ile Trp His Gly Arg Asp Glu Ala
465                 470                 475                 480

Lys Arg Gln Gly Asn Lys Pro Leu Ser Gln Ala Leu Lys Ile Ile Met
                485                 490                 495

Asn Ala Phe Tyr Gly Val Leu Gly Thr Thr Ala Cys Arg Phe Phe Asp
                500                 505                 510

Pro Arg Leu Ala Ser Ser Ile Thr Met Arg Gly His Gln Ile Met Arg
                515                 520                 525

Gln Thr Lys Ala Leu Ile Glu Ala Gln Gly Tyr Asp Val Ile Tyr Gly
                530                 535                 540

Asp Thr Asp Ser Thr Phe Val Trp Leu Lys Gly Ala His Ser Glu Glu
545                 550                 555                 560

Glu Ala Ala Lys Ile Gly Arg Ala Leu Val Gln His Val Asn Ala Trp
                565                 570                 575

Trp Ala Glu Thr Leu Gln Lys Gln Arg Leu Thr Ser Ala Leu Glu Leu
                580                 585                 590
```

```
Glu Tyr Glu Thr His Phe Cys Arg Phe Leu Met Pro Thr Ile Arg Gly
            595                 600                 605

Ala Asp Thr Gly Ser Lys Lys Arg Tyr Ala Gly Leu Ile Gln Glu Gly
    610                 615                 620

Asp Lys Gln Arg Met Val Phe Lys Gly Leu Glu Thr Val Arg Thr Asp
625                 630                 635                 640

Trp Thr Pro Leu Ala Gln Gln Phe Gln Gln Glu Leu Tyr Leu Arg Ile
                645                 650                 655

Phe Arg Asn Glu Pro Tyr Gln Glu Tyr Val Arg Glu Thr Ile Asp Lys
                    660                 665                 670

Leu Met Ala Gly Glu Leu Asp Ala Arg Leu Val Tyr Arg Lys Arg Leu
                675                 680                 685

Arg Arg Pro Leu Ser Glu Tyr Gln Arg Asn Val Pro Pro His Val Arg
    690                 695                 700

Ala Ala Arg Leu Ala Asp Glu Glu Asn Gln Lys Arg Gly Arg Pro Leu
705                 710                 715                 720

Gln Tyr Gln Asn Arg Gly Thr Ile Lys Tyr Val Trp Thr Thr Asn Gly
                    725                 730                 735

Pro Glu Pro Leu Asp Tyr Gln Arg Ser Pro Leu Asp Tyr Glu His Tyr
                740                 745                 750

Leu Thr Arg Gln Leu Gln Pro Val Ala Glu Gly Ile Leu Pro Phe Ile
                755                 760                 765

Glu Asp Asn Phe Ala Thr Leu Met Thr Gly Gln Leu Gly Leu Phe
                770                 775                 780

<210> SEQ ID NO 15
<211> LENGTH: 903
<212> TYPE: PRT
<213> ORGANISM: Bacteriophage RB69
<220> FEATURE:
<221> NAME/KEY: PEPTIDE
<222> LOCATION: (1)..(903)

<400> SEQUENCE: 15

Met Lys Glu Phe Tyr Leu Thr Val Glu Gln Ile Gly Asp Ser Ile Phe
1               5                   10                  15

Glu Arg Tyr Ile Asp Ser Asn Gly Arg Glu Arg Thr Arg Glu Val Glu
                20                  25                  30

Tyr Lys Pro Ser Leu Phe Ala His Cys Pro Glu Ser Gln Ala Thr Lys
            35                  40                  45

Tyr Phe Asp Ile Tyr Gly Lys Pro Cys Thr Arg Lys Leu Phe Ala Asn
    50                  55                  60

Met Arg Asp Ala Ser Gln Trp Ile Lys Arg Met Glu Asp Ile Gly Leu
65                  70                  75                  80

Glu Ala Leu Gly Met Asp Asp Phe Lys Leu Ala Tyr Leu Ser Asp Thr
                85                  90                  95

Tyr Asn Tyr Glu Ile Lys Tyr Asp His Thr Lys Ile Arg Val Ala Asn
            100                 105                 110

Phe Asp Ile Glu Val Thr Ser Pro Asp Gly Phe Pro Glu Pro Ser Gln
    115                 120                 125

Ala Lys His Pro Ile Asp Ala Ile Thr His Tyr Asp Ser Ile Asp Asp
    130                 135                 140

Arg Phe Tyr Val Phe Asp Leu Leu Asn Ser Pro Tyr Gly Asn Val Glu
145                 150                 155                 160

Glu Trp Ser Ile Glu Ile Ala Ala Lys Leu Gln Glu Gln Gly Gly Asp
```

```
            165                 170                 175
Glu Val Pro Ser Glu Ile Ile Asp Lys Ile Ile Tyr Met Pro Phe Asp
            180                 185                 190
Asn Glu Lys Glu Leu Leu Met Glu Tyr Leu Asn Phe Trp Gln Gln Lys
            195                 200                 205
Thr Pro Val Ile Leu Thr Gly Trp Asn Val Glu Ser Phe Asp Ile Pro
210                 215                 220
Tyr Val Tyr Asn Arg Ile Lys Asn Ile Phe Gly Glu Ser Thr Ala Lys
225                 230                 235                 240
Arg Leu Ser Pro His Arg Lys Thr Arg Val Lys Val Ile Glu Asn Met
            245                 250                 255
Tyr Gly Ser Arg Glu Ile Ile Thr Leu Phe Gly Ile Ser Val Leu Asp
            260                 265                 270
Tyr Ile Asp Leu Tyr Lys Lys Phe Ser Phe Thr Asn Gln Pro Ser Tyr
            275                 280                 285
Ser Leu Asp Tyr Ile Ser Glu Phe Glu Leu Asn Val Gly Lys Leu Lys
            290                 295                 300
Tyr Asp Gly Pro Ile Ser Lys Leu Arg Glu Ser Asn His Gln Arg Tyr
305                 310                 315                 320
Ile Ser Tyr Asn Ile Ile Asp Val Tyr Arg Val Leu Gln Ile Asp Ala
                        325                 330                 335
Lys Arg Gln Phe Ile Asn Leu Ser Leu Asp Met Gly Tyr Tyr Ala Lys
                        340                 345                 350
Ile Gln Ile Gln Ser Val Phe Ser Pro Ile Lys Thr Trp Asp Ala Ile
                        355                 360                 365
Ile Phe Asn Ser Leu Lys Glu Gln Asn Lys Val Ile Pro Gln Gly Arg
            370                 375                 380
Ser His Pro Val Gln Pro Tyr Pro Gly Ala Phe Val Lys Glu Pro Ile
385                 390                 395                 400
Pro Asn Arg Tyr Lys Tyr Val Met Ser Phe Asp Leu Thr Ser Leu Tyr
                        405                 410                 415
Pro Ser Ile Ile Arg Gln Val Asn Ile Ser Pro Glu Thr Ile Ala Gly
                        420                 425                 430
Thr Phe Lys Val Ala Pro Leu His Asp Tyr Ile Asn Ala Val Ala Glu
            435                 440                 445
Arg Pro Ser Asp Val Tyr Ser Cys Ser Pro Asn Gly Met Met Tyr Tyr
450                 455                 460
Lys Asp Arg Asp Gly Val Val Pro Thr Glu Ile Thr Lys Val Phe Asn
465                 470                 475                 480
Gln Arg Lys Glu His Lys Gly Tyr Met Leu Ala Ala Gln Arg Asn Gly
                        485                 490                 495
Glu Ile Ile Lys Glu Ala Leu His Asn Pro Asn Leu Ser Val Asp Glu
                        500                 505                 510
Pro Leu Asp Val Asp Tyr Arg Phe Asp Phe Ser Asp Glu Ile Lys Glu
            515                 520                 525
Lys Ile Lys Lys Leu Ser Ala Lys Ser Leu Asn Glu Met Leu Phe Arg
530                 535                 540
Ala Gln Arg Thr Glu Val Ala Gly Met Thr Ala Gln Ile Asn Arg Lys
545                 550                 555                 560
Leu Leu Ile Asn Ser Leu Tyr Gly Ala Leu Gly Asn Val Trp Phe Arg
            565                 570                 575
Tyr Tyr Asp Leu Arg Asn Ala Thr Ala Ile Thr Thr Phe Gly Gln Met
            580                 585                 590
```

Ala Leu Gln Trp Ile Glu Arg Lys Val Asn Glu Tyr Leu Asn Glu Val
            595                 600                 605

Cys Gly Thr Glu Gly Glu Ala Phe Val Leu Tyr Gly Asp Thr Asp Ser
    610                 615                 620

Ile Tyr Val Ser Ala Asp Lys Ile Ile Asp Lys Val Gly Glu Ser Lys
625                 630                 635                 640

Phe Arg Asp Thr Asn His Trp Val Asp Phe Leu Asp Lys Phe Ala Arg
                645                 650                 655

Glu Arg Met Glu Pro Ala Ile Asp Arg Gly Phe Arg Glu Met Cys Glu
            660                 665                 670

Tyr Met Asn Asn Lys Gln His Leu Met Phe Met Asp Arg Glu Ala Ile
            675                 680                 685

Ala Gly Pro Pro Leu Gly Ser Lys Gly Ile Gly Gly Phe Trp Thr Gly
            690                 695                 700

Lys Lys Arg Tyr Ala Leu Asn Val Trp Asp Met Glu Gly Thr Arg Tyr
705                 710                 715                 720

Ala Glu Pro Lys Leu Lys Ile Met Gly Leu Glu Thr Gln Lys Ser Ser
                725                 730                 735

Thr Pro Lys Ala Val Gln Lys Ala Leu Lys Glu Cys Ile Arg Arg Met
            740                 745                 750

Leu Gln Glu Gly Glu Glu Ser Leu Gln Glu Tyr Phe Lys Glu Phe Glu
            755                 760                 765

Lys Glu Phe Arg Gln Leu Asn Tyr Ile Ser Ile Ala Ser Val Ser Ser
770                 775                 780

Ala Asn Asn Ile Ala Lys Tyr Asp Val Gly Gly Phe Pro Gly Pro Lys
785                 790                 795                 800

Cys Pro Phe His Ile Arg Gly Ile Leu Thr Tyr Asn Arg Ala Ile Lys
                805                 810                 815

Gly Asn Ile Asp Ala Pro Gln Val Val Glu Gly Glu Lys Val Tyr Val
            820                 825                 830

Leu Pro Leu Arg Glu Gly Asn Pro Phe Gly Asp Lys Cys Ile Ala Trp
            835                 840                 845

Pro Ser Gly Thr Glu Ile Thr Asp Leu Ile Lys Asp Asp Val Leu His
            850                 855                 860

Trp Met Asp Tyr Thr Val Leu Leu Glu Lys Thr Phe Ile Lys Pro Leu
865                 870                 875                 880

Glu Gly Phe Thr Ser Ala Ala Lys Leu Asp Tyr Glu Lys Lys Ala Ser
                885                 890                 895

Leu Phe Asp Met Phe Asp Phe
            900

<210> SEQ ID NO 16
<211> LENGTH: 898
<212> TYPE: PRT
<213> ORGANISM: Bacteriophage T4
<220> FEATURE:
<221> NAME/KEY: PEPTIDE
<222> LOCATION: (1)..(898)

<400> SEQUENCE: 16

Met Lys Glu Phe Tyr Ile Ser Ile Glu Thr Val Gly Asn Asn Ile Val
1               5                   10                  15

Glu Arg Tyr Ile Asp Glu Asn Gly Lys Glu Arg Thr Arg Glu Val Glu
            20                  25                  30

Tyr Leu Pro Thr Met Phe Arg His Cys Lys Glu Glu Ser Lys Tyr Lys

```
                35                  40                  45
Asp Ile Tyr Gly Lys Asn Cys Ala Pro Gln Lys Phe Pro Ser Met Lys
 50                  55                  60

Asp Ala Arg Asp Trp Met Lys Arg Met Glu Asp Ile Gly Leu Glu Ala
 65                  70                  75                  80

Leu Gly Met Asn Asp Phe Lys Leu Ala Tyr Ile Ser Asp Thr Tyr Gly
                 85                  90                  95

Ser Glu Ile Val Tyr Asp Arg Lys Phe Val Arg Val Ala Asn Cys Asp
                100                 105                 110

Ile Glu Val Thr Gly Asp Lys Phe Pro Asp Pro Met Lys Ala Glu Tyr
                115                 120                 125

Glu Ile Asp Ala Ile Thr His Tyr Asp Ser Ile Asp Asp Arg Phe Tyr
                130                 135                 140

Val Phe Asp Leu Leu Asn Ser Met Tyr Gly Ser Val Ser Lys Trp Asp
145                 150                 155                 160

Ala Lys Leu Ala Ala Lys Leu Asp Cys Glu Gly Gly Asp Glu Val Pro
                165                 170                 175

Gln Glu Ile Leu Asp Arg Val Ile Tyr Met Pro Phe Asp Asn Glu Arg
                180                 185                 190

Asp Met Leu Met Glu Tyr Ile Asn Leu Trp Glu Gln Lys Arg Pro Ala
                195                 200                 205

Ile Phe Thr Gly Trp Asn Ile Glu Gly Phe Asp Val Pro Tyr Ile Met
210                 215                 220

Asn Arg Val Lys Met Ile Leu Gly Glu Arg Ser Met Lys Arg Phe Ser
225                 230                 235                 240

Pro Ile Gly Arg Val Lys Ser Lys Leu Ile Gln Asn Met Tyr Gly Ser
                245                 250                 255

Lys Glu Ile Tyr Ser Ile Asp Gly Val Ser Ile Leu Asp Tyr Leu Asp
                260                 265                 270

Leu Tyr Lys Lys Phe Ala Phe Thr Asn Leu Pro Ser Phe Ser Leu Glu
                275                 280                 285

Ser Val Ala Gln His Glu Thr Lys Lys Gly Lys Leu Pro Tyr Asp Gly
                290                 295                 300

Pro Ile Asn Lys Leu Arg Glu Thr Asn His Gln Arg Tyr Ile Ser Tyr
305                 310                 315                 320

Asn Ile Ile Asp Val Glu Ser Val Gln Ala Ile Asp Lys Ile Arg Gly
                325                 330                 335

Phe Ile Asp Leu Val Leu Ser Met Ser Tyr Tyr Ala Lys Met Pro Phe
                340                 345                 350

Ser Gly Val Met Ser Pro Ile Lys Thr Trp Asp Ala Ile Ile Phe Asn
                355                 360                 365

Ser Leu Lys Gly Glu His Lys Val Ile Pro Gln Gln Gly Ser His Val
                370                 375                 380

Lys Gln Ser Phe Pro Gly Ala Phe Val Phe Glu Pro Lys Pro Ile Ala
385                 390                 395                 400

Arg Arg Tyr Ile Met Ser Phe Asp Leu Thr Ser Leu Tyr Pro Ser Ile
                405                 410                 415

Ile Arg Gln Val Asn Ile Ser Pro Glu Thr Ile Arg Gly Gln Phe Lys
                420                 425                 430

Val His Pro Ile His Glu Tyr Ile Ala Gly Thr Ala Pro Lys Pro Ser
                435                 440                 445

Asp Glu Tyr Ser Cys Ser Pro Asn Gly Trp Met Tyr Asp Lys His Gln
                450                 455                 460
```

-continued

```
Glu Gly Ile Ile Pro Lys Glu Ile Ala Lys Val Phe Phe Gln Arg Lys
465                 470                 475                 480

Asp Trp Lys Lys Lys Met Phe Ala Glu Met Asn Ala Glu Ala Ile
                485                 490                 495

Lys Lys Ile Ile Met Lys Gly Ala Gly Ser Cys Ser Thr Lys Pro Glu
                500                 505                 510

Val Glu Arg Tyr Val Lys Phe Ser Asp Asp Phe Leu Asn Glu Leu Ser
                515                 520                 525

Asn Tyr Thr Glu Ser Val Leu Asn Ser Leu Ile Glu Glu Cys Glu Lys
                530                 535                 540

Ala Ala Thr Leu Ala Asn Thr Asn Gln Leu Asn Arg Lys Ile Leu Ile
545                 550                 555                 560

Asn Ser Leu Tyr Gly Ala Leu Gly Asn Ile His Phe Arg Tyr Tyr Asp
                565                 570                 575

Leu Arg Asn Ala Thr Ala Ile Thr Ile Phe Gly Gln Val Gly Ile Gln
                580                 585                 590

Trp Ile Ala Arg Lys Ile Asn Glu Tyr Leu Asn Lys Val Cys Gly Thr
                595                 600                 605

Asn Asp Glu Asp Phe Ile Ala Ala Gly Asp Thr Asp Ser Val Tyr Val
                610                 615                 620

Cys Val Asp Lys Val Ile Glu Lys Val Gly Leu Asp Arg Phe Lys Glu
625                 630                 635                 640

Gln Asn Asp Leu Val Glu Phe Met Asn Gln Phe Gly Lys Lys Lys Met
                645                 650                 655

Glu Pro Met Ile Asp Val Ala Tyr Arg Glu Leu Cys Asp Tyr Met Asn
                660                 665                 670

Asn Arg Glu His Leu Met His Met Asp Arg Glu Ala Ile Ser Cys Pro
                675                 680                 685

Pro Leu Gly Ser Lys Gly Val Gly Gly Phe Trp Lys Ala Lys Lys Arg
                690                 695                 700

Tyr Ala Leu Asn Val Tyr Asp Met Glu Asp Lys Arg Phe Ala Glu Pro
705                 710                 715                 720

His Leu Lys Ile Met Gly Met Glu Thr Gln Gln Ser Ser Thr Pro Lys
                725                 730                 735

Ala Val Gln Glu Ala Leu Glu Glu Ser Ile Arg Arg Ile Leu Gln Glu
                740                 745                 750

Gly Glu Glu Ser Val Gln Glu Tyr Tyr Lys Asn Phe Glu Lys Glu Tyr
                755                 760                 765

Arg Gln Leu Asp Tyr Lys Val Ile Ala Glu Val Lys Thr Ala Asn Asp
                770                 775                 780

Ile Ala Lys Tyr Asp Asp Lys Gly Trp Pro Gly Phe Lys Cys Pro Phe
785                 790                 795                 800

His Ile Arg Gly Val Leu Thr Tyr Arg Arg Ala Val Ser Gly Leu Gly
                805                 810                 815

Val Ala Pro Ile Leu Asp Gly Asn Lys Val Met Val Leu Pro Leu Arg
                820                 825                 830

Glu Gly Asn Pro Phe Gly Asp Lys Cys Ile Ala Trp Pro Ser Gly Thr
                835                 840                 845

Glu Leu Pro Lys Glu Ile Arg Ser Asp Val Leu Ser Trp Ile Asp His
                850                 855                 860

Ser Thr Leu Phe Gln Lys Ser Phe Val Lys Pro Leu Ala Gly Met Cys
865                 870                 875                 880
```

-continued

Glu Ser Ala Gly Met Asp Tyr Glu Glu Lys Ala Ser Leu Asp Phe Leu
                885                 890                 895

Phe Gly

<210> SEQ ID NO 17
<211> LENGTH: 575
<212> TYPE: PRT
<213> ORGANISM: Bacteriophage phi-29
<220> FEATURE:
<221> NAME/KEY: PEPTIDE
<222> LOCATION: (1)..(575)

<400> SEQUENCE: 17

Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asn Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Lys Lys Ile Ala Lys Asp Phe Lys Leu Thr Val Leu Lys Gly
    130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Lys Phe Lys
        195                 200                 205

Lys Val Phe Pro Thr Leu Ser Leu Gly Leu Asp Lys Glu Val Arg Tyr
    210                 215                 220

Ala Tyr Arg Gly Gly Phe Thr Trp Leu Asn Asp Arg Phe Lys Glu Lys
225                 230                 235                 240

Glu Ile Gly Glu Gly Met Val Phe Asp Val Asn Ser Leu Tyr Pro Ala
                245                 250                 255

Gln Met Tyr Ser Arg Leu Leu Pro Tyr Gly Glu Pro Ile Val Phe Glu
            260                 265                 270

Gly Lys Tyr Val Trp Asp Glu Asp Tyr Pro Leu His Ile Gln His Ile
        275                 280                 285

Arg Cys Glu Phe Glu Leu Lys Glu Gly Tyr Ile Pro Thr Ile Gln Ile
    290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                325                 330                 335

```
Lys Glu His Tyr Asp Leu Tyr Asn Val Glu Tyr Ile Ser Gly Leu Lys
            340                 345                 350

Phe Lys Ala Thr Thr Gly Leu Phe Lys Asp Phe Ile Asp Lys Trp Thr
        355                 360                 365

Tyr Ile Lys Thr Thr Ser Glu Gly Ala Ile Lys Gln Leu Ala Lys Leu
    370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
                405                 410                 415

Gly Glu Glu Thr Lys Asp Pro Val Tyr Thr Pro Met Gly Val Phe
            420                 425                 430

Ile Thr Ala Trp Ala Arg Tyr Thr Thr Ile Thr Ala Ala Gln Ala Cys
        435                 440                 445

Tyr Asp Arg Ile Ile Tyr Cys Asp Thr Asp Ser Ile His Leu Thr Gly
    450                 455                 460

Thr Glu Ile Pro Asp Val Ile Lys Asp Ile Val Asp Pro Lys Lys Leu
465                 470                 475                 480

Gly Tyr Trp Ala His Glu Ser Thr Phe Lys Arg Ala Lys Tyr Leu Arg
                485                 490                 495

Gln Lys Thr Tyr Ile Gln Asp Ile Tyr Met Lys Glu Val Asp Gly Lys
            500                 505                 510

Leu Val Glu Gly Ser Pro Asp Asp Tyr Thr Asp Ile Lys Phe Ser Val
        515                 520                 525

Lys Cys Ala Gly Met Thr Asp Lys Ile Lys Lys Glu Val Thr Phe Glu
    530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys
                565                 570                 575

<210> SEQ ID NO 18
<211> LENGTH: 38
<212> TYPE: DNA
<213> ORGANISM: Artificial Sequence
<220> FEATURE:
<223> OTHER INFORMATION: Cy5-38-mer primer
<220> FEATURE:
<221> NAME/KEY: primer
<222> LOCATION: (1)..(38)

<400> SEQUENCE: 18
gcttgcacaa gttcgttcaa tgatacggcg accaccga                              38

<210> SEQ ID NO 19
<211> LENGTH: 45
<212> TYPE: DNA
<213> ORGANISM: Artificial Sequence
<220> FEATURE:
<223> OTHER INFORMATION: 45-mer template
<220> FEATURE:
<221> NAME/KEY: template
<222> LOCATION: (1)..(45)
<220> FEATURE:
<221> NAME/KEY: misc_feature
<222> LOCATION: (7)..(7)
<223> OTHER INFORMATION: n is a, c, g, or t

<400> SEQUENCE: 19
cgttccntcg gtggtcgccg tatcattgaa cgaacttgtg caagc                      45
```

```
<210> SEQ ID NO 20
<211> LENGTH: 38
<212> TYPE: DNA
<213> ORGANISM: Artificial Sequence
<220> FEATURE:
<223> OTHER INFORMATION: FAM-38-mer primer
<220> FEATURE:
<221> NAME/KEY: primer
<222> LOCATION: (1)..(38)

<400> SEQUENCE: 20
gcttgcacaa gttcgttcaa tgatacggcg accaccga                              38

<210> SEQ ID NO 21
<211> LENGTH: 19
<212> TYPE: DNA
<213> ORGANISM: Artificial Sequence
<220> FEATURE:
<223> OTHER INFORMATION: FAM-19-mer primer
<220> FEATURE:
<221> NAME/KEY: primer
<222> LOCATION: (1)..(19)

<400> SEQUENCE: 21
gcttgcacag ggcctcgac                                                    19
```